United States Patent
Strickland

(10) Patent No.: US 11,206,843 B1
(45) Date of Patent: *Dec. 28, 2021

(54) MILK PRODUCT COMPOSITIONS

(71) Applicant: BIOMILQ, Inc., Durham, NC (US)

(72) Inventor: Leila Strickland, Hillsborough, NC (US)

(73) Assignee: BIOMILQ, Inc., Durham, NC (US)

(*) Notice: Subject to any disclaimer, the term of this patent is extended or adjusted under 35 U.S.C. 154(b) by 0 days.

This patent is subject to a terminal disclaimer.

(21) Appl. No.: 17/301,216

(22) Filed: Mar. 29, 2021

Related U.S. Application Data

(60) Provisional application No. 63/200,480, filed on Mar. 9, 2021, provisional application No. 63/030,149, filed on May 26, 2020.

(51) Int. Cl.
*C12N 5/071* (2010.01)
*A23C 9/20* (2006.01)
*C12N 5/078* (2010.01)

(52) U.S. Cl.
CPC .............. *A23C 9/203* (2013.01); *A23C 9/206* (2013.01); *C12N 5/0631* (2013.01); *C12N 5/0634* (2013.01); *C12N 2501/315* (2013.01); *C12N 2502/095* (2013.01); *C12N 2502/11* (2013.01); *C12N 2513/00* (2013.01)

(58) Field of Classification Search
CPC ............ C12N 5/0631; C12N 2502/095; C12N 2502/11; C12N 2513/00; C12N 2501/315
See application file for complete search history.

(56) References Cited

U.S. PATENT DOCUMENTS

| | | |
|---|---|---|
| 6,358,920 B1 | 3/2002 | Blaschuk et al. |
| 2013/0344490 A1 | 12/2013 | Kim |
| 2015/0079584 A1 | 3/2015 | Gevaert et al. |
| 2017/0267970 A1 | 9/2017 | Gupta et al. |
| 2018/0066220 A1 | 3/2018 | Nath et al. |
| 2019/0211296 A1 | 7/2019 | Allbritton |
| 2021/0207090 A1 | 7/2021 | Strickland |

FOREIGN PATENT DOCUMENTS

| | | |
|---|---|---|
| EP | 0911389 A2 | 4/1999 |
| WO | WO-20210142241 A1 | 7/2021 |

OTHER PUBLICATIONS

Watson. Immunological Functions of the Mammary Gland and Its Secretion-Comparative Review. Aust. J. Biol. Sci., 1980, 33, 403-22 (Year: 1980).*

Gourdou et al. Development of a Constitutively Active Mutant Form of the Prolactin Receptor, a Member of the Cytokine Receptor Family. Molecular Endocrinology. 1996. vol. 10, No. 1, p. 45-56 (Year: 1996).*

Shennan et al. Transport of Milk Constituents by the Mammary Gland. Physiological Reviews vol. 80, No. 3, Jul. 2000 (Year: 2000).*

Arèvalo Turrubiarte, M., et al., Phenotypic and functional characterization of two bovine mammary epithelial cell lines in 2D and 3D models, Am J Physiol, 310: C348-C356, (2016).

Blatchford D.R., et al., Milk Secretion in Cultured Mammary Epithelial Cells, In: Kitagawa, Y., et al. (eds), Animal Cell Technology: Basic & Applied Aspects, Springer, Dordrecht, 10: 141-145 (1999).

Chen, G., et al., Isolation, culture, and differentiation of mammary epithelial stem/progenitor cells from fresh or ex vivo cultured human breast tissue, Curr Protoc Cell Biol, 82(1): e65 (2019).

Cho, et al., Constructions of a 3D mammary duct based on spatial localization of the extracellular matrix, NPG Asia Mat, 10:970-981 (2018).

Co-Pending U.S. Appl. No. 17/247,672, filed Dec. 18, 2020.

Morada, M., et al., Continuous culture of Cryptosporidium parvum using hollow fiber technology, Int J for Parasitol, 46 (1): 21-29 (2016).

Sharfstein, S.T., et al., Functional Differentiation and Primary Metabolism of Mouse Mammary Epithelial Cells in Extended-Batch and Hollow-Fiber Culture, Biotechnol and Bioeng, 40(6): 672-680 (1992).

U.S. Appl. No. 17/247,672 Office Action dated Apr. 5, 2021.

Yonemura, S., Differential sensitivity of epithelial cells to extracellular matrix in polarity establishment, PLOS One, 9 (11): e112922 (2014).

Gourdou, I., et al., Expression by transgenesis of a constitutively active mutant form of the prolactin receptor induces premature abnormal development of the mouse mammary gland and lactation failure, Biol Reprod, 70(3): 718-728 (2004).

Kozlowski, M., et al., Differences in growth and transcriptomic profile of bovine mammary epithelial monolayer and three-dimensional cell cultures, J Physiol Pharmacol, 60(Suppl 1): 5-14 (2009).

O'Brien, L.E., et al., Rac1 orientates epithelial apical polarity through effects on basolateral laminin assembly, Nat Cell Biol, 3(9): 831-838 (2001).

PCT/US2020/066209 International Search Report and Written Opinion dated Apr. 22, 2021.

Yang, N.S., et al., Growth of human mammary epithelial cells on collagen gel surfaces, Cancer Res, 41(10): 4093-4100 (1983).

* cited by examiner

*Primary Examiner* — Taeyoon Kim
(74) *Attorney, Agent, or Firm* — Goodwin Procter LLP

(57) ABSTRACT

Disclosed herein are milk compositions that comprise protein, lipid, and oligosaccharide components at concentrations that mimic and/or are substantially similar to human breast milk as produced by a lactating female. The milk compositions include one or more milk components produced in vitro and/or ex vivo from cultured mammary cells.

13 Claims, 7 Drawing Sheets
Specification includes a Sequence Listing.

MILK PRODUCT COMPOSITIONS

CROSS-REFERENCE

This application claims the benefit of priority from U.S. Provisional Application No. 63/030,149 filed on May 26, 2020, and U.S. Provisional Application No. 63/200,480 filed on Mar. 9, 2021, the contents of each are incorporated herein by reference in their entireties.

SEQUENCE LISTING

The instant application contains a Sequence Listing which has been submitted in ASCII format and is hereby incorporated by reference in its entirety. Said ASCII copy, created on Apr. 26, 2021, is named BMQ_001_SL.txt and is 29,417 bytes in size.

FIELD

This disclosure relates to milk product compositions that comprise protein, lipid, and oligosaccharide components and component concentrations that mimic human breast milk as produced by a lactating female, which milk compositions are produced in vitro and/or ex vivo from cultured mammary cells.

BACKGROUND

Milk is a staple of the human diet, both during infancy and throughout life. The American Academy of Pediatrics and World Health Organization recommend that infants be exclusively breastfed for the first 6 months of life, and consumption of dairy beyond infancy is a mainstay of human nutrition, representing a 700 billion dollar industry worldwide. However, lactation is a physiologically demanding and metabolically intensive process that can present biological and practical challenges for breastfeeding mothers, and milk production is associated with environmental, social, and animal welfare impacts in agricultural contexts.

The possibility of using mammalian cell culture to produce food has gained increasing interest in recent years, with the development of several successful prototypes of meat and sea food products from cultured muscle and fat cells (Stephens et al. 2018 Trends Food Sci Technol. 78:155-166). Additionally, efforts are underway to commercialize the production of egg and milk proteins using microbial expression systems. However, this fermentation-based process relies on the genetically engineered expression and purification of individual components and is unable to reproduce the full molecular profile of milk or dairy.

SUMMARY OF THE DISCLOSURE

The present disclosure relates to milk compositions that comprise protein, lipid, and oligosaccharide components and component concentrations that mimic and/or are substantially similar to human breast milk as produced by a lactating female and are produced in vitro and/or ex vivo from cultured mammary cells.

Thus, one aspect of the disclosure relates to milk products comprising specified concentrations or amounts by weight of protein components, lipid components human milk oligosaccharide components and lactose, wherein at least one of the protein components, lipid components, HMOs, and lactose is produced by cultured human mammary epithelial cells. In an embodiment, disclosed herein are methods of producing an isolated cultured milk product from mammary cells, the method comprising: (a) culturing a cell construct in a bioreactor under conditions which produce the cultured milk product, said cell construct comprising: (i) a three-dimensional scaffold having an exterior surface, an interior surface defining an interior cavity, and a plurality of pores extending from the interior surface to the exterior surface; (ii) a matrix material disposed on the exterior surface of the three-dimensional scaffold; (iv) a plurality of plasma cells disposed on the matrix material; and (v) a confluent monolayer of polarized mammary cells disposed on the plurality of plasma cells, wherein the mammary cells are selected from the group consisting of: mammary epithelial cells, mammary myoepithelial cells, mammary progenitor cells, wherein the polarized mammary cells comprise an apical surface and a basal surface; and (b) isolating the cultured milk product. In some embodiments, the cultured milk product comprises secretory IgA (sIgA).

In some embodiments, the bioreactor comprises an apical compartment that is substantially isolated from the internal cavity of the cell construct. In some embodiments, the basal surface of the mammary cells is in fluidic contact with the culture media. In some embodiments, the apical compartment is in fluidic contact with the apical surface of the mammary cells. In some embodiments, the cultured milk product is secreted from the apical surface of the mammary cells into the apical compartment. In some embodiments, the culture media substantially does not contact the cultured milk product. In some embodiments, total cell density of mammary cells within the bioreactor is at least $10^{11}$. In some embodiments, total surface area of mammary cells within the bioreactor is at least 1.5 $m^2$. In some embodiments, the matrix material comprises one or more extracellular matrix proteins. In some embodiments, total cell density of plasma cells in the bioreactor is about 200 to 500 plasma cells per $mm^2$. In some embodiments, the culturing is carried out at a temperature of about 27° C. to about 39° C. In some embodiments, the culturing is carried out at an atmospheric concentration of $CO^2$ of about 4% to about 6%.

In certain embodiments, described herein are cell constructs, comprising: (a) a three dimensional scaffold having an exterior surface, an interior surface defining an interior cavity/basal chamber, and a plurality of pores extending from the interior surface to the exterior surface; (b) a matrix material disposed on the exterior surface of the three-dimensional scaffold; (c) a culture media disposed within the interior cavity/basal chamber and in fluidic contact with the internal surface; and (d) a plurality of plasma cells disposed on the matrix material; and (e) an at least 70% confluent monolayer of polarized mammary cells disposed on the plurality of plasma cells, wherein the mammary cells are selected from the group consisting of: mammary epithelial cells, mammary myoepithelial cells, and mammary progenitor cells. In some embodiments, the polarized mammary cells comprise an apical surface and a basal surface. In some embodiments, the basal surface of the mammary cells is in fluidic contact with the culture media.

In some embodiments, at least 70%, at least 80%, at least 90%, at least 95%, at least 99%, or 100% of the mammary cells are polarized in the same orientation. In some embodiments, the monolayer of polarized mammary cells is at least 70% confluent, at least 80% confluent, at least 90% confluent, at least 95% confluent, at least 99% confluent, or 100% confluent. In some embodiments, the mammary cells comprise a constitutively active prolactin receptor protein. In some embodiments, the culture medium comprises a carbon source, a chemical buffering system, one or more essential amino acids, one or more vitamins and/or cofactors, and one or more inorganic salts. In some embodiments, the culture medium further comprises prolactin. In some embodiments, the matrix material comprises one or more extracellular matrix proteins. In some embodiments, the three-dimensional scaffold comprises a natural polymer, a biocompatible synthetic polymer, a synthetic peptide, a composite derived from any of the preceding, or any combination thereof. In some embodiments, the natural polymer is collagen, chitosan, cellulose, agarose, alginate, gelatin, elastin, heparan sulfate, chondroitin sulfate, keratan sulfate, and/or hyaluronic acid. In some embodiments, the biocompatible synthetic polymer is polysulfone, polyvinylidene fluoride, polyethylene co-vinyl acetate, polyvinyl alcohol, sodium polyacrylate, an acrylate polymer, and/or polyethylene glycol.

In certain aspects, described herein is a milk product comprising: about 6-14 grams per liter (g/L) protein components; about 18-89 g/L lipid components; about 7-14 g/L human milk oligosaccharides (HMOs); and about 64-77 g/L lactose, wherein at least one of the protein components, lipid components, HMOs, and lactose is produced by cultured human mammary epithelial cells.

In some embodiments, the milk product further comprises one or more immunoglobulins. In some embodiments, the immunoglobulin is secretory IgA.

In some embodiments, the protein component comprises about 55-65% dry weight of the milk product. In some embodiments, the protein component comprises beta-casein, kappa-casein and alpha-casein. In some embodiments, the beta-casein has a concentration of about 0.5-1.5 g/L, the kappa-casein has a concentration of about 0.5-0.6 g/L, and the alpha-casein has a concentration of about 0.1-0.5 g/L in the milk product. In some embodiments, the beta-casein, kappa-casein and alpha-casein together comprise about 35-45% dry weight percent of the protein component of the milk product. In some embodiments, the beta-casein comprises greater than about 50% of total casein content.

In some embodiments, the protein component further comprises one or more of alpha-lactalbumin, lysozyme, lactoferrin, haptocorrin, butyrophilin, osteopontin, mucin MC5, mucin BrE3, and lactadherin. In some embodiments, the protein component further comprises serum albumin. In some embodiments, the alpha-lactalbumin has a concentration of about 2.7-3.3 g/L in the milk product. In some embodiments, the lysozyme has a concentration of about 0.2-0.5 g/L in the milk product. In some embodiments, the lactoferrin has a concentration of about 1.0-2.0 g/L in the milk product. In some embodiments, the haptocorrin has a concentration of about 0.07-0.7 g/L in the milk product. In some embodiments, the butyrophilin has a concentration of about 0.03-0.05 g/L in the milk product. In some embodiments, the osteopontin has a concentration of about 0.05-0.2 g/L in the milk product. In some embodiments, the mucin MC5 has a concentration of about 0.5-0.6 g/L in the milk product. In some embodiments, the mucin BrE3 has a concentration of about 0.5-0.7 g/L in the milk product. In some embodiments, the lactadherin has a concentration of about 0.06-0.07 g/L in the milk product. In some embodiments, the serum albumin has a concentration of about 0.025-3.5 g/L, or about 0.01-2 g/L, or about 0.15-1 g/L, or about 0.2-0.7 g/L. In some embodiments, the protein components are of human origin.

In some embodiments, the lipid component comprises one or more of saturated fatty acids, monounsaturated fatty acids, polyunsaturated fatty acids, cholesterol, phospholipids, plasmalogens and sphingolipids. In some embodiments, the saturated fatty acids has a concentration of about 5-34 g/L in the milk product. In some embodiments, the saturated fatty acids comprise palmitic acid, stearic acid, and lauric acid. In some embodiments, the palmitic acid comprises at least about 50% sn-2 form. In some embodiments, palmitic acid has a concentration of about 3-18 g/L in the milk product. In some embodiments, stearic acid has a concentration of about 0.7-5 g/L in the milk product. In some embodiments, lauric acid has a concentration of about 0.5-5 g/L in the milk product. In some embodiments, monounsaturated fatty acids have a concentration of about 7-46 g/L in the milk product. In some embodiments, the monounsaturated fatty acid comprises oleic acid. In some embodiments, the oleic acid comprises at least about 50% sn-1 form. In some embodiments, the oleic acid has a concentration of about 7-45 g/L in the milk product. In some embodiments, polyunsaturated fats have a concentration of about 2-20 g/L in the milk product. In some embodiments, the polyunsaturated fats comprise one or more of linoleic acid, alpha-linolenic acid, eicosadienoic acid, arachidonic acid, dihomo-gamma-linolenic acid, and docosahexadienoic acid. In some embodiments, linoleic acid has a concentration of about 2-19 g/L in the milk product. In some embodiments, the linoleic acid comprises at least about 50% sn-3 form. In some embodiments, alpha-linolenic acid has a concentration of about 0.5-0.7 g/L in the milk product. In some embodiments, eicosadienoic acid has a concentration of about 0.5-0.7 g/L in the milk product. In some embodiments, arachidonic acid has a concentration of about 0.5-0.7 g/L in the milk product. In some embodiments, dihomo-gamma-linolenic acid has a concentration of about 0.3-0.5 g/L in the milk product. In some embodiments, docosahexadienoic acid has a concentration of about 0.02-0.4 g/L in the milk product. In some embodiments, linoleic acid has a concentration of about 2-19 g/L, alpha-linolenic acid has a concentration of about 0.5-0.7 g/L, eicosadienoic acid has a concentration of about 0.5-0.7 g/L, arachidonic acid has a concentration of about 0.5-0.7 g/L, dihomo-gamma-linolenic acid has a concentration of about 0.3-0.5 g/L, and docosahexadienoic acid has a concentration of about 0.02-0.4 g/L in the milk product. In some embodiments, the milk product comprises oleic acid, palmitic acid, and linoleic acid, wherein the oleic acid comprises at least about 50% sn-1 form, the palmitic acid comprises at least about 50% sn-2 form, and the linoliec acid comprises at least about 50% sn-3 form. In some embodiments, the milk product coprises cholesterol having a concentration of about 0.09-0.15 g/L in milk product. In some embodiments, phospholipids, plasmalogens and sphingolipids together have a concentration of about 0.1-0.4 g/L in the milk product.

In some embodiments, the human milk oligosaccharide component comprises one or more neutral oligosaccharides. In some embodiments, the human milk oligosaccharide component comprises one or more acidic oligosaccharides. In some embodiments, the human milk oligosaccharide component comprises neutral oligosaccharides and/or acidic oligosaccharides. In some embodiments, the one or more neutral oligosaccharides comprise TF-LNH (trifucosyllacto-N-hexose), 2'-FL (2'-fucosyllactose), DF-LNHII (difucosyl-lacto-N-hexaose), LNFP I (lacto-N-fucopentaose I), LND-FHI (lacto-N-difucosylhexaose I), LNT (lacto-N-tetraose), LNnT (lacto-N-neotetraose), DF-L (Difucosyllactose), and 3-FL (3-fucosyllactose).

In some embodiments, the one or more acidic oligosaccharides comprise 6'-SL (6'-sialyllactose), DS-LNT (di-sialyllacto-N-tetraose), FS-LNnH I (fucosyl-sialyl-lacto-N-neohexaose I), LST c (sialyl-lacto-N-tetraose c), and 3'-SL (3'-sialyllactose). In some embodiments, the one or more neutral oligosaccharides comprises TF-LNH (trifucosyl-lacto-N-hexose), which oligosaccharide has a concentration of about 1-4 g/L in the milk product. In some embodiments, the one or more neutral oligosaccharides comprises 2'-FL (2'-fucosyllactose), which oligosaccharide has a concentration of about 1-4 g/L in the milk product. In some embodiments, the one or more neutral oligosaccharides comprises DF-LNHII (difucosyllacto-N-hexaose), which oligosaccharide has a concentration of about 1-4 g/L in the milk product. In some embodiments, the one or more neutral oligosaccharides comprises LNFP I (lacto-N-fucopentaose I), which oligosaccharide has a concentration of about 0.5-2 g/L in the milk product. In some embodiments, the one or more neutral oligosaccharides comprises LNDFHI (lacto-N-difucosyl-hexaose I), which oligosaccharide has a concentration of about 0.2-2 g/L in the milk product.

In some embodiments, the one or more neutral oligosaccharides comprises LNT (lacto-N-tetraose), which oligosaccharide has a concentration of about 0.3-1.5 g/L in the milk product. In some embodiments, the one or more neutral oligosaccharides comprises LNnT (lacto-N-neotetraose), which oligosaccharide has a concentration of about 0.5-1.5 g/L in the milk product. In some embodiments, the one or more neutral oligosaccharides comprises DF-L (Difucosyl-lactose), which oligosaccharide has a concentration of about 0.1-1 g/L in the milk product. In some embodiments, the one or more neutral oligosaccharides comprises 3-FL (3-fuco-syllactose), which oligosaccharide has a concentration of about 0.2-1.5 g/L in the milk product. In some embodiments, the one or more acidic oligosaccharides comprises 6'-SL (6'-sialyllactose), which oligosaccharide has a concentration of about 0.2-1.2 g/L in the milk product. In some embodiments, the one or more acidic oligosaccharides comprises DS-LNT (disialyllacto-N-tetraose), which oligosaccharide has a concentration of about 0.05-1 g/L in the milk product. In some embodiments, the one or more acidic oligosaccharides comprises FS-LNnH I (fucosyl-sialyl-lacto-N-neo-hexaose I), which oligosaccharide comprises about 0.05-0.7 g/L in the milk product. In some embodiments, the one or more acidic oligosaccharides comprises LST c (sialyl-lacto-N-tetraose c), which oligosaccharide has a concentration of about 0.05-0.7 g/L in the milk product. In some embodiments, the one or more acidic oligosaccharides comprises 3'-SL (3'-sialyllactose), which oligosaccharide has a concentration of about 0.1-0.3 g/L in the milk product.

In some embodiments, the one or more neutral oligosaccharides comprise TF-LNH (trifucosyllacto-N-hexose), 2'-FL (2'-fucosyllactose), DF-LNH II (difucosyllacto-N-hexaose), LNFP I (lacto-N-fucopentaose I), LNDFHI (lacto-N-difucosylhexaose I), LNT (lacto-N-tetraose), LNnT (lacto-N-neotetraose), DF-L (Difucosyllactose), and 3-FL (3-fucosyllactose) and wherein the one or more acidic oligosaccharides comprises 6'-SL (6'-sialyllactose), DS-LNT (disialyllacto-N-tetraose), FS-LNnH I (fucosyl-sialyl-lacto-N-neohexaose I), LST c (sialyl-lacto-N-tetraose c), and 3'-SL (3'-sialyllactose). In some embodiments, the milk product comprises about 1-4 g/L TF-LNH (trifucosyl-lacto-N-hexose), about 1-4 g/L 2'-FL (2'-fucosyllactose), about 1-4 g/L DF-LNH II (difucosyllacto-N-hexaose), about 0.5-2 g/L LNFP I (lacto-N-fucopentaose I), about 0.22 g/L LNDFH I (lacto-N-difucosylhexaose I), about 0.3-1.5 g/L LNT (lacto-N-tetraose), about 0.5-1.5 g/L LNnT (lacto-N-neotetraose), about 0.1-1 g/L DF-L (Difucosyllactose), about 0.2-1.5 g/L 3-FL (3-fucosyllactose), about 0.2-1.2 g/L 6'-SL (6'-sialyllactose), about 0.05-1 g/L DS-LNT (disialyl-lacto-N-tetraose), about 0.05-0.7 g/L FS-LNnH I (fucosyl-sialyl-lacto-N-neohexaose I), about 0.05-0.7 g/L LST c (sialyl-lacto-N-tetraose c), and about 0.1-0.3 g/L 3'-SL (3'-sialyllactose). In some embodiments, the neutral oligosaccharides content comprises at least about 2-fold, or about 3-fold, or about 4-fold, or about 5-fold, or about 6-fold, or about 7-fold, or about 8-fold, or about 9-fold, or about 10-fold, or about 11-fold, or about 12-fold, or about 13-fold, or about 14-fold, or about 15-fold more by weight than acidic oligosaccharide content.

In certain aspects, described herein are milk products comprising: about 6-14 grams per liter (g/L) protein components; about 18-89 g/L lipid components; about 7-14 g/L human milk oligosaccharides (HMOs); and about 64-77 g/L lactose, wherein the protein components comprise beta-casein, kappa-casein, and alpha-casein, alpha-lactalbumin, lysozyme, lactoferrin, haptocorrin, butyrophilin, osteopontin, mucin MC5, mucin BrE3, and lactadherin, wherein the lipid components comprise palmitic acid, stearic acid and lauric acid, oleic acid, linoleic acid, alpha-linolenic acid, eicosadienoic acid, arachidonic acid, dihomo-gamma-linolenic acid, docosahexadienoic acid, cholesterol, phospholipids, plasmalogens and sphingolipids, wherein the human milk oligosaccharides comprise TF-LNH (trifucosyllacto-N-hexose), 2'-FL (2'-fucosyllactose), DF-LNHII (difucosyl-lacto-N-hexaose), LNFP I (lacto-N-fucopentaose I), LNDFHI (lacto-N-difucosylhexaose I), LNT (lacto-N-tetraose), LNnT (lacto-N-neotetraose), DF-L (Difucosyllactose), and 3-FL (3-fucosyllactose), 6'-SL (6'-sialyllactose), DS-LNT (disialyllacto-N-tetraose), FS-LNnH I (fucosyl-sialyl-lacto-N-neohexaose I), LST c (sialyl-lacto-N-tetraose c), and 3'-SL (3'-sialyllactose), and wherein at least one of the protein components, lipid components, HMOs, and lactose is produced by cultured human mammary epithelial cells.

In some embodiments, the milk product comprises about 0.5-1.5 g/L beta-casein, about 0.5-0.6 g/L kappa-casein, about 0.1-0.5 g/L alpha-casein, about 2.7-3.3 g/L alpha-lactalbumin, about 0.2-0.5 g/L lysozyme, about 1.0-2.0 g/L lactoferrin, about 0.07-0.7 g/L haptocorrin, about 0.03-0.05 g/L butyrophilin, about 0.05-0.2 g/L osteopontin, about 0.5-0.6 g/L mucin MC5, about 0.5-0.7 g/L mucin BrE3, about 0.06-0.07 g/L lactadherin, about 2-19 g/L linoleic acid, about 0.5-0.7 g/L alpha-linolenic acid, about 0.5-0.7 g/L eicosadienoic acid, about 0.5-0.7 g/L arachidonic acid, about 0.3-0.5 g/L dihomo-gamma-linolenic acid, about 0.02-0.4 g/L docosahexadienoic acid, about 0.09-0.15 g/L cholesterol, about 0.1-0.4 g/L phospholipids, plasmalogens, and sphingolipids combined, about 1-4 g/L TF-LNH (trifucosyl-lacto-N-hexose), about 1-4 g/L 2'-FL (2'-fucosyllactose), about 1-4 g/L DF-LNHII (difucosyllacto-N-hexaose), about 0.5-2 g/L LNFP I (lacto-N-fucopentaose I), about 0.2-2 g/L LNDFHI (lacto-N-difucosylhexaose I), about 0.3-1.5 g/L LNT (lacto-N-tetraose), about 0.5-1.5 g/L LNnT (lacto-N-neotetraose), about 0.1-1 g/L DF-L (Difucosyllactose), about 0.2-1.5 g/L 3-FL (3-fucosyllactose), about 0.2-1.2 g/L 6'-SL (6'-sialyllactose), about 0.05-1 g/L DS-LNT (disialyl-lacto-N-tetraose), about 0.05-0.7 g/L FS-LNnH I (fucosyl-sialyl-lacto-N-neohexaose I), about 0.05-0.7 g/L LST c (sialyl-lacto-N-tetraose c), and about 0.1-0.3 g/L 3'-SL (3'-sialyllactose).

In certain aspects, described herein are milk products comprising: about 3-15 percent protein by weight; about 9-92 percent lipid by weight; about 4-15 percent by weight human milk oligosaccharides (HMOs); and about 33-80 percent by weight lactose, wherein at least one of the protein, lipid, HMOs, and lactose is produced by cultured human mammary epithelial cells. In some embodiments, the milk product further comprises serum albumin. In some embodiments, the milk product comprises about 0.025-3.5 g/L, or about 0.01-2 g/L, or about 0.15-1 g/L, or about 0.3-0.7 g/L serum albumin.

In some embodiments, the milk product further comprises one or more immunoglobulins. In some embodiments, the immunoglobulins comprise one or more of IgA, IgG and IgM. In some embodiments, the IgA comprises one or more of IgA2 (secretory) and IgA1 (non-secretory). In some embodiments, the milk product comprises about 0.2-1.0 g/L secretory IgA. In some embodiments, the milk product comprises about 0.15-1.6 g/L total IgA. In some embodiments, the milk product comprises about 0.03-0.3 g/L IgG. In some embodiments, the milk product comprises about 0.01-0.1 g/L IgM. In some embodiments, the milk product comprises about 0.2-2 percent by weight immunoglobulins.

In some embodiments, the protein components, lipid components, HMOs, and lactose are isolated from cultured mammary epithelial cells. In some embodiments, the cultured mammary epithelial cells comprise one or more immortalized mammary cell lines. In some embodiments, the cultured mammary epithelial cells are derived from one or more primary mammary tissue samples. In some embodiments, the one or more primary mammary tissue samples is derived from a surgical explant of mammary gland tissue. In some embodiments, the one or more primary mammary tissue samples comprises alveolar and/or luminal tissue or cells collected from the alveolar structure of the mammary gland. In some embodiments, the one or more primary mammary tissue samples is derived from a needle aspiration of mammary gland tissue. In some embodiments, the primary mammary tissue further comprises one or more myoepithelial cells. In some embodiments, the primary mammary tissue further comprises one or more stem cells. In some embodiments, the primary mammary tissue further comprises one or more immune cells. In some embodiments, the immune cells comprise B cells. In some embodiments, the immune cells comprise plasma cells.

In some embodiments, the milk product is isolated from cultured mammary epithelial cells from one or more specific persons. In some embodiments, the milk product isolated from cultured mammary epithelial cells from a specific donor is provided only to that donor or persons authorized by that donor. In some embodiments, the cultured mammary epithelial cells are co-cultured with one or more plasma cells lines. In some embodiments, the cultured mammary epithelial cells are co-cultured with one or more myoepithelial cell lines. In some embodiments, the cultured mammary epithelial cells are co-cultured with one or more stem cell lines.

In some embodiments, the milk product comprises at least about 80%, or at least about 85%, or at least about 90%, or at least about 95%, or at least about 97%, or at least about 98%, or at least about 99%, of the overall macromolecular composition of human breast milk. In some embodiments, non-protein nitrogen content comprises at least about 10%, or at least about 15%, or at least about 20%, or at least about 25%, or at least about 30% of total nitrogen content.

In certain aspects, described herein are frozen milk products, comprising a milk product described herein that has been frozen. In some embodiments, the milk product has been lyophilized. In certain aspects, described herein is a containerized milk product, comprising a milk product described herein that is packaged into a container. In certain aspects, described herein is a containerized frozen milk product, comprising the frozen milk product that is packaged into a container. In certain aspects, described herein is a containerized lyophilized milk product, comprising the lyophilized milk product that is packaged into a container.

In certain aspects, described herein are extracted milk products, comprising one or more components extracted from a milk product described herein. In some embodiments, the one or more components extracted from the collected milk product are lyophilized or concentrated to produce a lyophilized or a concentrated extracted milk product component. In some embodiments, the one or more components extracted from the collected milk product are concentrated by membrane filtration or reverse osmosis. In some embodiments, the one or more extracted components from the collected milk product comprise milk protein, lipid, carbohydrate, vitamin, and minerals.

In certain aspects, described herein are containerized extracted milk products, comprising the extracted milk product described herein that is packaged in a container. In some embodiments, the container is sterile. In some embodiments, the container is vacuum-sealed. In some embodiments, the container is a food grade container. In some embodiments, the container is a canister, a jar, a bottle, a bag, a box, or a pouch.

In some embodiments, the milk product comprises about 500-1150 kcal/L available energy content. In some embodiments, between about 40-55% of the available energy content of the milk product is from lipids. In some embodiments, the milk product comprises between about 95.8 and 195.2 g/L macromolecular content.

In certain aspects, described herein are methods of treating a patient suffering from an infectious disease, comprising: administering to the patient an effective amount of a milk product comprising: about 6-14 grams per liter (g/L) protein components; about 18-89 g/L lipid components; about 7-14 g/L human milk oligosaccharides (HMOs); and about 64-77 g/L lactose, wherein at least one of the protein components, lipid components, HMOs, and lactose. In some embodiments, the milk product further comprises one or more immunoglobulins. In some embodiments, the immunoglobulins comprise one or more of IgA, IgG and IgM. In some embodiments, the IgA comprises one or more of IgA2 (secretory) and IgA1 (non-secretory).

In some embodiments, the milk product comprises about 0.2-1.0 g/L secretory IgA. In some embodiments, milk product comprises about 0.15-1.6 g/L total IgA. In some embodiments, the milk product comprises about 0.03-0.3 g/L IgG. In some embodiments, the milk product comprises about 0.01-0.1 g/L IgM. In some embodiments, the milk product comprises about 0.2-2 percent by weight immunoglobulins. In some embodiments, the infectious disease is a gastrointestinal infection. In some embodiments, the patient is immune compromised.

In certain aspects, described herein are methods of treating an infant suffering from a gastrointestinal infection comprising administering an effective amount of a milk product comprising: about 6-14 grams per liter (g/L) protein components; about 18-89 g/L lipid components; about 7-14 g/L human milk oligosaccharides (HMOs); and about 64-77 g/L lactose, wherein at least one of the protein components, lipid components, HMOs, and lactose. In some embodiments, the milk product further comprises one or more immunoglobulins. In some embodiments, the immunoglobulins comprise one or more of IgA, IgG and IgM. In some embodiments, the IgA comprises one or more of IgA2 (secretory) and IgA1 (non-secretory). In some embodiments, the milk product comprises about 0.2-1.0 g/L secretory IgA. In some embodiments, the milk product comprises about 0.15-1.6 g/L total IgA. In some embodiments, the milk product comprises about 0.03-0.3 g/L IgG. In some embodiments, the milk product comprises about 0.01-0.1 g/L IgM.

In some embodiments, the milk product comprises about 0.2-2 percent by weight immunoglobulins.

These and other aspects of the disclosure are set forth in more detail in the description of the disclosure below.

DETAILED DESCRIPTION

Figure 1:
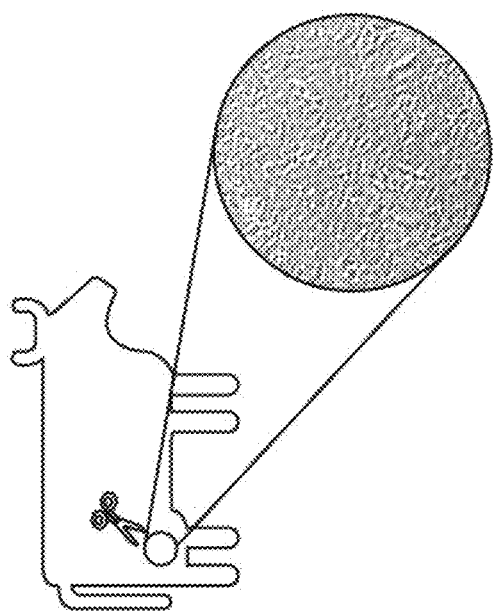
FIG. 1 shows an example of the collection of milk for nutritional use from mammary epithelial cells grown as a confluent monolayer in a compartmentalizing culture apparatus in which either fresh or recycled media is provided to the basal compartment and milk is collected from the apical compartment. TEER, transepithelial electrical resistance.
Figure 1:
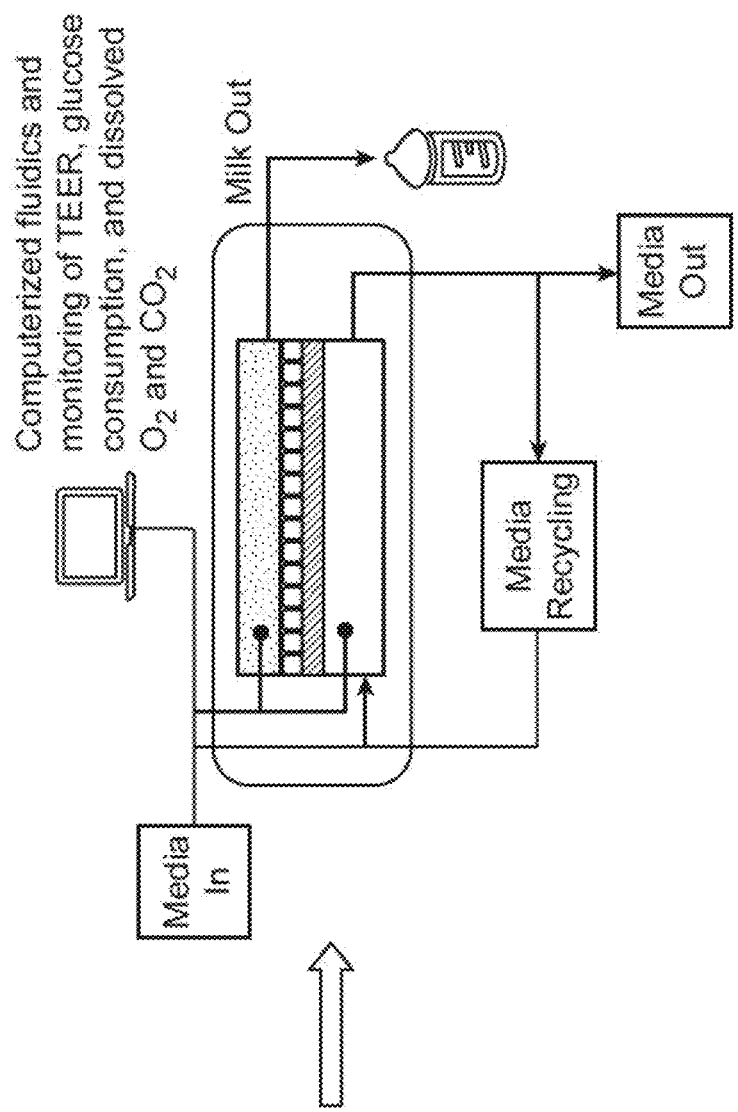

Milk is a nutrient-rich liquid food produced in the mammary glands of mammals. It is a primary source of nutrition for infant mammals (including humans who are breastfed) before they are able to digest other types of food. Milk is a complex biological matrix composed of thousands of unique molecules, with nutritional and functional properties that are ideal to support the growth and development of a mammalian infant.

Natural milk contains many macronutrients, including proteins, lipids, polysaccharides and lactose. Each species produces milk with a unique composition that reflects its distinct physiological needs (Beck K L, et al., *J Proteome Res.* 2015; 14(5):2143-2157). As milk composition is optimized for each species, breast milk is considered the gold standard for human infant nutrition and is recommended as the exclusive nutrition source for the first 6 months by the World Health Organization (Mordor Intelligence, Global dairy market (2016-2024)).

Compared with bovine milk, human milk is lower in protein but higher in fat and carbohydrate content (Ballard 0, et al., *Pediatr Clin North Am.* 2013; 60(1):49-74). Many components overlap but undergo different processing steps in humans and cows and therefore differ in their final conformations and physiological properties. For example, the positions of specific fatty acids in triglycerides differ between bovine milk and breast milk, and these differences have been shown to affect absorption (Andreas N J, et al., *Early Hum Dev.*; 91 (11):629-635). Additionally, human milk contains hundreds of unique oligosaccharides that contribute to gut maturation and immunity in the developing infant, which are lacking in bovine-based formula (Totten S M, et al., *J Proteome Res.* 2012; 1 1(12):6124-6133).

Human milk is not merely nutritional. Rather, human milk contains a variety of factors with bioactive qualities that have a profound role in infant survival and health. Early milk from mammals contains antibodies that provide protection to the newborn baby. Additional factors contributing to the disease fighting potential of natural milk include leukocytes, hormones, antimicrobial peptides, cytokines, chemokines, and other bioactive factors.

Secretory IgA (sIgA) is found in naturally-occurring breast milk. IgA is produced by plasma cells located within the breast tissue. The IgA binds to a receptor (polymeric Ig receptor) on the basal surface of mammary epithelial cells. The IgA and receptor are transported into the mammary epithelial cells where the mammary cells process the IgA by cleaving the extracellular domain of the polymeric Ig receptor bound to the IgA, leaving the soluble ectodomain of the Ig receptor (the "secretory component") bound to the IgA. The sIgA is secreted from the apical surface of the mammary epithelial cells. sIgA transferred to children via breast milk is an integral component of an infant's immune system enabling them to fight off infections. Further, sIgA is an important component of the immune systems of all humans and sIgA deficiencies are associated with increased susceptibility to illness. sIgA-based therapies offer the opportunity to prevent and treat infectious diseases at their sites of entry.

Immune cells, including CD20+ B cells, which are precursors for sIgA-secreting plasma cells, are present in normal, non-lactating mammary tissue. During lactation, immune cell homing to the mammary gland contributes to a local, mucosal immunity that helps to prevent infection within the mammary gland. Further, immune cell homing to the mammary gland enables the transfer of sIgA antibodies to an infant via breast feeding.

Unfortunately, efforts at mass production of sIgA are hampered by the fact that it is a multivalent and heavily post-translationally modified protein assembly that requires cooperation with a mucosal epithelium for processing into its bioactive form. Thus, it is difficult to manufacture sIgA for use with non-naturally occurring breast milk or as a therapeutic for humans.

These are several of the factors that contribute to the inability of infant formula to replicate the properties of breast milk. Therefore, there is a need for improved milk products for developing infants and children that more closely mimic the composition of human breast milk as produced by a lactating female.

Mammary epithelial cells (MECs) in culture have been previously demonstrated to display organization and behavior similar to that observed in vivo (Arevalo et al. 2016 *Am J Physiol Cell Physiol.* 310(5):C348-3 56; Chen et al. 2019 *Curr Protoc Cell Biol.* 82(1):e65). In Arevalo et al., specific biomarkers of MEC populations were detected in immortalized bovine mammary epithelial cells (BME-UV1) and immortalized bovine mammary alveolar cells (MAC-T) cultured on adherent 2-D plates, ultralow attachment surface 3D microplates, and 3D plates coated with Matrigel. Additionally, in Chen et al., protocols are detailed for isolation and culture of human primary mammary epithelial stem/progenitor cells from human breast tissue and subsequent generation of mammospheres using 3D organoid culture on gelatin sponges and Matrigel matrices. However, neither Arevalo nor Chen attempted to stimulate the production of milk from these MEC cultures.

In particular, when grown on an appropriate extracellular matrix and stimulated with prolactin, cultured bovine mammary epithelial cells polarize and organize into structures capable of secreting certain milk components (Blatchford et al. 1999 *Animal Cell Technology: Basic & Applied Aspects* 10:141-145). In Blatchford et al, bovine MECs polarized and formed mammospheres. Casein and butyrophilin were isolated from the cultures. However, the cells did not polarize in one uniform direction. Blatchford, et al. noted that the milk proteins were distributed in between the cells and dispersed throughout the mammospheres. Due to the lack of a uniform polarization orientation, Blatchford had to isolate the secreted proteins from the culture media.

Furthermore, in vitro two-dimensional models, such as those used in Blatchford et al. provide a low surface area-to-volume ratio (low density format). The surface area available for cell attachment limits the number of cells that can be grown The only known attempt to culture mouse mammary epithelial cells in a high-density format, such as the hollow fiber bioreactor, failed to achieve compartmentalization necessary for the production and extraction of a cultured milk product (Sharfstein et al. 1992 *Biotechnology and Bioengineering* 40:672-680). In Sharfstein et al., growth, long-term expression of functional differentiation, and metabolism of COMMA-1D (an immortalized mouse mammary epithelial cell line) was examined in two different systems: extended batch culture and hollow-fiber reactor culture. Using COMMA-1D seeded onto Costar Transwell® polycarbonate membrane cell culture inserts, Sharfstein et al. created a confluent monolayer capable of barrier formation and polarized metabolism between the apical and basal side that maintained gradients of glucose and lactate. However, using a hollow-fiber bioreactor culture, Sharfstein et al. was unable to achieve separation of basal and apical compartments. Furthermore, it was not determined if nutrient uptake was polarized in a hollow-fiber culture (Sharfstein et al. 1992). Importantly, no prior work has been able to culture mammary epithelial cells from humans or other nutritionally relevant species in a high-density, three-dimensional, compartmentalizing format.

The present disclosure is explained in greater detail below. This description is not intended to be a detailed catalog of all the different ways in which the disclosure may be implemented, or all the features that may be added to the instant disclosure. For example, features illustrated with respect to one embodiment may be incorporated into other embodiments, and features illustrated with respect to a particular embodiment may be deleted from that embodiment. Numerous variations and additions to the various embodiments suggested herein will be apparent to those skilled in the art in light of the instant disclosure, which do not depart from the instant disclosure. Hence, the following specification is intended to illustrate some particular embodiments of the disclosure, and not to exhaustively specify all permutations, combinations, and variations thereof.

Unless the context indicates otherwise, it is specifically intended that the various features of the disclosure described herein can be used in any combination. Moreover, the present disclosure also contemplates that in some embodiments of the disclosure, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Definitions

Unless otherwise defined, all technical and scientific terms used herein have the same meaning as commonly understood by one of ordinary skill in the art to which this disclosure belongs. The terminology used in the description of the disclosure herein is for the purpose of describing particular embodiments only and is not intended to be limiting of the disclosure.

The terminology used herein is for the purpose of describing particular embodiments only and is not intended to be limiting. As used herein, the singular forms "a," "an," and "the" are intended to include the plural forms as well, unless the context clearly indicates otherwise. It will be further understood that the terms "comprises" and/or "comprising," when used in this specification, specify the presence of stated features, elements, and/or components, but do not preclude the presence or addition of one or more other features, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Moreover, the present disclosure also contemplates that in some embodiments, any feature or combination of features set forth herein can be excluded or omitted.

Furthermore, the term "about," as used herein when referring to a measurable value such as an amount of a compound or agent of this disclosure, dose, time, temperature, and the like, is meant to encompass variations of ±10%, ±5%, ±1%, ±0.5%, or even ±0.1% of the specified amount.

As used herein, the transitional phrase "consisting essentially of" is to be interpreted as encompassing the recited materials or steps and those that do not materially affect the basic and novel characteristic(s) of the disclosure. Thus, the term "consisting essentially of" as used herein should not be interpreted as equivalent to "comprising."

As used herein, the compositions described in the present disclosure are referred to interchangeably as (the singular or plural forms of) "nutritional compositions substantially similar to human milk," "milk products," "milk compositions," "cultured milk products," or equivalent as made clear by the context.

As used herein, by "isolate" (or grammatical equivalents, e.g., "extract") a product, it is meant that the product is at least partially separated from at least some of the other components in the starting material.

As used herein, the term "polypeptide" encompasses both peptides and proteins, and does not require any particular amino acid length or tertiary structure unless indicated otherwise.

The term "polarized" as used herein in reference to cells and/or monolayers of cells refers to a spatial status of the cell wherein there are two distinct surfaces of the cell, e.g., an apical surface and a basal surface, which may be different. In some embodiments, the distinct surfaces of a polarized cell comprises different surface and/or transmembrane receptors and/or other structures. In some embodiments, individual polarized cells in a continuous monolayer have similarly-oriented apical surfaces and basal surfaces. In some embodiments, individual polarized cells in a continuous monolayer have communicative structures between individual cells (e.g., tight junctions) to allow cross communication between individual cells and to create separation (e.g., compartmentalization) of the apical compartment and basal compartment.

As used herein, "apical surface" means the surface of a cell that faces an external environment or toward a cavity or chamber, for example the cavity of an internal organ. With respect to mammary epithelial cells, the apical surface is the surface from which the cultured milk product is secreted.

As used herein, "basal surface" means the surface of a cell that is in contact with a surface, e.g., the matrix of a bioreactor.

As used herein, "bioreactor" means a device or system that supports a biologically active environment that enables the production of a cultured milk product described herein from mammary cells described herein.

The term "lactogenic" as used herein refers to the ability to stimulate production and/or secretion of milk. A gene or protein (e.g., prolactin) may be lactogenic, as may any other natural and/or synthetic product. In some embodiments, a lactogenic culture medium comprises prolactin, thereby stimulating production of milk by cells in contact with the culture medium.

As used herein, the term "food grade" refers to materials considered non-toxic and safe for consumption (e.g., human and/or other animal consumption), e.g., as regulated by standards set by the U.S. Food and Drug Administration.

Cell Constructs

Included herein are cell constructs for producing a cultured milk product representing the biosynthetic output of cultured mammary epithelial cells (immortalized or from primary tissue samples) and IgA producing cells, for example plasma cells. Disclosed herein, in certain embodiments, are cell constructs for producing cultured milk products comprising sIgA, the cell constructs comprising: (a) a three dimensional scaffold having an exterior surface, an interior surface defining an interior cavity/basal chamber, and a plurality of pores extending from the interior surface to the exterior surface; (b) a matrix material disposed on the exterior surface of the three-dimensional scaffold; (c) a culture media disposed within the interior cavity/basal chamber and in fluidic contact with the internal surface; (d) a population of plasma cells (PCs) disposed on the matrix material and (e) a continuous monolayer of mammary cells disposed on the population of plasma cells, the mammary cells selected from the group consisting of: (i) mammary epithelial cells, (ii) mammary myoepithelial cells, and (iii) mammary progenitor cells.

Mammary Cells

In some embodiments, the mammary cells comprise milk-producing mammary epithelial cells (MECs), contractile myoepithelial cells, and/or progenitor cells that can give rise to both mammary epithelial cells (MECs) and mammary contractile myoepithelial cells. Mammary epithelial cells (MECs) are the only cells that produce milk. In some embodiments, the mammary cells comprise mammary epithelial cells (MECs), primary mammary epithelial cells, mammary myoepithelial cells and mammary progenitor cells. In some embodiments, the mammary cells are obtained from a tissue biopsy of a mammary gland.

In some embodiments, the mammary cells are derived from breast milk-derived stem cells or breast stem cells originating from tissue biopsy of a mammary gland. The epithelial component of breast milk includes not only mature epithelial cells, but also their precursors and stem cells in culture. A subpopulation of breast milk-derived stem cells displays very high multilineage potential, resembling those typical for human embryonic stem cells (hESCs). Breast stem cells may also originate from tissue biopsy of the mammary gland, and include terminally differentiated MECs. Both breast milk-derived stem cells and breast stem cells originating from tissue biopsy of the mammary gland are multi-potent cells that can give rise to MECs or myoepithelial cells.

In some embodiments, at least 50% of the mammary cells of the cells culture are polarized. In some embodiments, at least 55% of the mammary cells of the cell culture are polarized. In some embodiments, at least 60% of the mammary cells of the cell culture are polarized. In some embodiments, at least 65% of the mammary cells of the cell culture are polarized. In some embodiments, at least 70% of the mammary cells of the cell culture are polarized. In some embodiments, at least 75% of the mammary cells of the cell culture are polarized. In some embodiments, at least 80% of the mammary cells of the cell culture are polarized. In some embodiments, at least 85% of the mammary cells of the cell culture are polarized. In some embodiments, at least 90% of the mammary cells of the cell culture are polarized. In some embodiments, at least 95% of the mammary cells of the cell culture are polarized. In some embodiments, at least 100% of the mammary cells of the cell culture are polarized. In some embodiments, substantially all of the mammary cells of the cell construct are polarized (i.e., have an apical surface and a basal surface). In some embodiments, substantially all of the mammary cells of the cell construct are polarized and substantially all of the polarized cells are oriented in the same direction. For example, in some embodiments, substantially all of the mammary cells have an apical surface and a basal surface, wherein the apical surface of substantially all of the cells is oriented in the same direction and the basal surface of substantially all of the cells is oriented in the same direction.

In some embodiments, the continuous monolayer of mammary cells has at least 70% confluence over the scaffold. In some embodiments, the continuous monolayer of mammary cells has at least about 75% confluence over the scaffold. In some embodiments, the continuous monolayer of mammary cells has at least about 80% confluence over the scaffold. In some embodiments, the continuous monolayer of mammary cells has at least about 85% confluence over the scaffold. In some embodiments, the continuous monolayer of mammary cells has at least about 90% confluence over the scaffold. In some embodiments, the continuous monolayer of mammary cells has at least about 95% confluence over the scaffold. In some embodiments, the continuous monolayer of mammary cells has at least about 99% confluence over the scaffold. In some embodiments, the continuous monolayer of mammary cells has 100% confluence over the scaffold.

Genetic Modifications to Mammary Cells

In some embodiments, the mammary cells comprise a constitutively active prolactin receptor protein. In some embodiments, the mammary cells comprise a constitutively active human prolactin receptor protein. Where the primary mammary epithelial cell or immortalized mammary epithelial cells comprise a constitutively active prolactin receptor, the culture medium does not contain prolactin.

In some embodiments, the constitutively active human prolactin receptor protein comprises a deletion of amino acids 9 through 187, wherein the numbering is based on the reference amino acid sequence of a human prolactin receptor identified as SEQ ID NO: 1.

SEQ ID NO: 1: Human prolactin receptor (GenBank accession number AAD32032.1)
MKENVASATVFTLLLFLNTCLLNGQLPPGK-PEIFKCRSPNKETFTCWWRPGTDGGLP TNYSLT-YHREGETLMHECPDYITGGPN-SCHFGKQYTSMWRTYIMMVNATNQMGSSFSDEL YVDVTYIVQPDPPLELAVEVKQPE-DRKPYLWIKWSPPTLIDLKTGWFTLLYEIRLKPE-KAAE WEIHFAGQQTEFKILSLHPGQKYLVQVRCK-PDHGYWSAWSPATFIQIPSDFTMNDTTVWIS VAVLSAVICLIIVWAVALKGYSMVTCIFPPVPGP-KIKGFDAHLLEKGKSEELLSALGCQDFPP TSDYEDLLVEYLEVDDSEDQHLMSVHSKEHP-SQGMKPTYLDPDTDSGRGSCDSPSLLSEKC EEPQANPSTFYDPEVIEKPENPETTHTWDPQCISMEG-KIPYFHAGGSKCSTWPLPQPSQHNPR SSYHNITDVCELAVGPAGAPATLLNEAGKDALKSSQ-TIKSREEGKATQQREVESFHSETDQD TPWLLPQEKTPFGSAKPLDYVEIHKVNKD-GALSLLPKQRENSGKPKKPGTPENNKEYAKVS GVMDNNILVLVPDPHAKNVACFEESAKE-APPSLEQNQAEKALANFTATSSKCRLQLGGLDY LDPACFTHSFH In some embodiments, the constitutively active human prolactin receptor protein comprising a deletion of the following amino acids: VFTLLLFLNTCLLNGQLPPGK-PEIFKCRSPNKETFTCWWRPGTDGGLPTNYSLT-YHREGETL MHECPDYITGGPN-SCHFGKQYTSMWRTYIMMVNATNQMGSSFSDELY VDVTYIVQPDPPL ELAVEVKQPE-DRKPYLWIKWSPPTLIDLKTGWFTLLYEIRLKPEKAA (e.g., amino acid positions 10 through 178 of SEQ ID NO: 1).

In some embodiments, the mammary cells comprise a loss of function mutation introduced into a circadian related gene PER2. In some embodiments, the loss of function mutation introduced into a circadian related gene PER2 promotes increased synthesis of cultured milk components. In some embodiments, the loss of function mutation in the PER2 gene comprises an 87-amino acid deletion from position 348 to 434 in PER2, wherein the numbering is based on the reference amino acid sequence of a human PER2 identified as SEQ ID NO: 2.

SEQ ID NO: 2: Human Period Circadian Protein Homolog 2 (GenBank Accession Number NM 022817)
MNGYAEFPPSPSNPTKEPVEPQP-SQVPLQEDVDMSSGSSGHETNENCSTGRDSQGSD CDDSGKJELGMLVEPPDARQSPDTFSLMMAKSEHNP STSGCSSDQSSKVDTHKEL1KTLKEL KVHLPADK-KAKGKASTLATLKYALRSVKQVKANEEYYQLL-MSSEGHPCGADVPSYTVEE MESVTSE-HIVKNADMFAVAVSLVSGKILYISDQVASIFHCKRD AFSDAKFVEFLAPHDVGVF HSFTSPYKLPLWSMCSGADSFTQEC-MEEKSFFCRVSVRKSHENEIRYHPFRMTPYLVKVRD QQGAESQLCCLLLAERVHSGYEAPRIPPEKRIFTTTH-TPNCLFQDVDERAVPLLGYLPQD LIETPVLVQLHPS-DRPLMLAIHKKILQSGGQPFDYSPIRFRARNG-EYITLDTSWSSFINP WSRKISFIIGRHKVRVGPLNEDVFAAHPCTEEKALHP-SIQELTEQIIRLLLQPVPHSGSSG YGSLGSNG-SHEHLMSQTSSSDSNGHEDSRRRRAEICKNGNKT-KNRSHYSHESGEQKKKSVT EMQTNPPAEKKAVPAMEKD-SLGVSFPEELACKNQPTCSYQQISCLDS-VIRYLESCNEAATLK RKCEFPANVPALRSSDKR-KATVSPGPHAGEAEPPSRVNSRTGVGTHLTSLALPG KAESVASL TSQCSYSS-TIVHVGDKKPQPELEMVEDAASGPESLD-CLAGPALACGLSQEKEPFKKLGLTKE VLAAHTQKE-EQSFLQKFKEIRKLSIFQSHCHYYLQERSKGQPSERTA PGLRNTSGIDSPWKK TGKNRKLKSKRVKPRDSSES-TGSGGPVSARPPLVGLNATAWSPSDTSQSS-CPAVPFPAPVPA AYSLPVFPAPGTVAAPPAP-PHASFTVPAVPVDLQHQFAVQPPPFPAPLAPVMAFM LPSYSFP SGTPNLPQAFFPSQPQFPSHPTLTSE-MASASQPEFPEGGTGAMGTTGATETAAVGADCKPGT SRDQQPKAPLTRDEPSDTQNSDALST-SSGLLNLLLNEDLCSASGSAASESLGSGSLGCDASPS GAGSSDTSHTSKYFGSIDSSENNHKAKMNTG-MEESEHFIKCVLQDPIWLLMADADSSVMM TYQLPSRNLEAVLKEDREKLKLLQKLQPRFT-ESQKQELREVHQWMQTGGLPAAIDVAECV YCEN-KEKGNICIPYEEDIPSLGLSEVSDTKEDENG-SPLNHRIEEQT In some embodiments, the loss of function mutation introduced into PER2 comprises a deletion of the following amino acids: CLFQDVDERAVPLLGYLPQDLI-ETPVLVQLHPSDRPLMLAIIKKILQSGGQPFDYSPIR-FRAR NGEYITLDTSWSSFINPWSRKISFIIGRHKV (e.g., amino acid positions 341 through 434 of SEQ ID NO:2).

In some embodiments, the mammary cells comprise a polynucleotide encoding a prolactin receptor comprising a modified intracellular signaling domain. In some embodiments, the loss of function mutation introduced into a circadian related gene PER2 promotes increased synthesis of individual cultured milk components. In some embodiments, the prolactin receptor comprises a truncation wherein position 154 of exon 10 has been spliced to the 3' sequence of exon 11. In some embodiments, the prolactin receptor comprises a sequence according to SEQ ID NO: 3.

SEQ ID NO: 3: Human Isoform 4 of Prolactin Receptor (GenBank Accession Number AF416619; Trott et al. 2003 *J. Mol. Endocrinol* 30(1):31-47)
MKENVASATVFTLLLFLNTCLLNGQLPPGK-PEIFKCRSPNKETFTCWWRPGTDGGLP TNYSLT-YHREGETLMHECPDYITGGPN-SCHFGKQYTSMWRTYIMMVNATNQMGSSFSDEL YVDVTYIVQPDPPLELAVEVKQPE- DRKPYLWIKWSPPTLIDLKTGWFTLLYEIRLKPE-KAAE WEIIIFAGQQTEFKILSLHPGQKYLVQVRCK-PDHGYWSAWSPATFIQIPSDFTMNDTTVWIS VAVLSAVICLIIVWAVALKGYSMVTCIFPPVPGP-KIKGFDAHLLEKGKSEELLSALGCQDFPP TSDYEDLLVEYLEVDDSEDQHLMSVHSKEHP-SQGDPLMLGASHYKNLKSYRPRKISSQGRL AVFTKATLTTVQ In some embodiments, the mammary cells comprise a polynucleotide encoding a modified (e.g., recombinant) effector of a prolactin protein. In some embodiments, the modified effector of the prolactin protein comprises a janus kinase-2 (JAK2) tyrosine kinase domain. In some embodiments, the modified effector comprises a JAK2 tyrosine kinase domain fused to a signal transducer and activator of transcription-5 (STAT5) tyrosine kinase domain (e.g., a polynucleotide encoding a JAK2 tyrosine kinase domain linked to the 3' end of a polynucleotide encoding the STAT5 tyrosine kinase domain). In some embodiments, the modified effector of a prolactin protein promotes increased synthesis of individual cultured milk components. In some embodiments, the modified effector has a sequence according to SEQ ID NO: 4. Bolded amino acids correspond to the JAK2 kinase domain of amino acid positions 757 through 1129 of a reference human JAK2 amino acid sequence.

SEQ ID NO: 4. STA5A Human Signal Transducer and Activator of Transcription 5A Fused at 3' End to Amino Acids 757-1129 of JAK2 Human Tyrosine-Protein Kinase MAGWIQAQQL QGDALRQMQV LYGQHFPIEV RHYLAQWIES QPWDAIDLDN PQDRAQATQL LEGLVQELQK KAEHQVGEDG FLLKIKLGHY ATQLQKTYDR CPLELVRCIR HILYNEQRLV REANNCSSPA GILVDAMSQK HLQINQTFEE LRLVTQDTEN ELKKLQQTQE YFIIQYQESL RIQAQFAQLA QLSPQERLSR ETALQQKQVS LEAWLQREAQ TLQQYRVELA EKHQKTLQLL RKQQTIILDD ELIQWKRRQQ LAGNGGPPEG SLDVLQSWCE KLAEIIWQNR QQIRRAEHLC QQLPIPGPVE EMLAEVNATI TDIISALVTS TFIIEKQPPQ VLKTQTKFAA TVRLLVGGKL NVHMNPPQVK ATIISEQQAK SLLKNENTRN ECSGEILNNC CVMEYHQATG TLSAHFRNMS LKRIKRADRR GAESVTEEKF TVLFESQFSV GSNELVFQVK TLSLPWVIV HGSQDHNATA TVLWD-NAFAE PGRVPFAVPD KVLWPQLCEA LNMKFKAEVQ SNRGLTKENL VFLAQKLFNN SSSHLEDYSG LSVSWSQFNR ENLPGWNYTF WQWFDGVMEV LKKHHKPHWN DGAILGFVNK QQAHDLLINK PDGT-FLLRFS DSEIGGITIA WKFDSPERNL WNLKPFTTRD FSIRSLADRL GDLSYLIYVF PDRPKDEVFS KYYTPV-LAKA VDGYVKPQIK QWPEFVNAS ADAGGSSATY MDQAPSPAVC PQAPYNMYPQ NPDHVLDQDG EFDL-DETMDV ARHVEELLRR PMDSLDSRLS PPAGLFT-SAR GSLSLDSQ RKLQFYEDRH QLPAPKWAEL ANLINNCMDY EPDFRPSFRA IIRDLNSLFT PDYELL-TEND MLPNMRIGAL GFSGAFEDRD PTQFEERHLK FLQQLGKGNF GSVEMCRYDP LQDNTGEWA VKKLQHSTEE HLRDFEREIE ILKSLQHDNI VKYKGVCYSA GRRNLKLIME YLPYGSLRDY LQKH-KERIDH IKLLQYTSQI CKGMEYLGTK RYIHRDLATR NILVENENRV KIGDFGLTKV LPQDKEYYKV KEPGESPIFW YAPESLTESK FSVASDVWSF GWLY-ELFTY IEKSKSPPAE FMRMIGNDKQ GQMIVFHLIE LLKNNGRLPR PDGCPDEIYM IMTECWNNNV NQRPSFRDLA LRVDQIRDN.

In some embodiments, the mammary cells are immortalized. In some embodiments, the mammary cells comprise one or more nucleic acids encoding human telomerase reverse transcriptase (hTERT) or simian virus 40 (SV40). In some embodiments, the mammary cells comprise a small hairpin RNA (shRNA) to p16 (Inhibitor of Cyclin-Dependent Kinase 4) (p16(INK4)) and Master Regulator of Cell Cycle Entry and Proliferative Metabolism (c-MYC).

In some embodiments, the method comprises introducing into the mammary cell: (a) a polynucleotide encoding a prolactin receptor comprising a modified intracellular signaling domain, optionally wherein the prolactin receptor comprises a truncation wherein position 154 of exon 10 has been spliced to the 3' sequence of exon 11; (b) a polynucleotide encoding a chimeric prolactin receptor that binds to a ligand, which is capable of activating milk synthesis in the absence of prolactin; (c) a polynucleotide encoding a constitutively or conditionally active prolactin receptor protein, optionally wherein the polynucleotide encodes a constitutively active human prolactin receptor protein comprising a deletion of amino acids 9 through 187 (e.g., a deletion of amino acids 9 through 187, wherein the numbering is based on the reference amino acid sequence of a human prolactin receptor identified as SEQ ID NO: 1); (d) a polynucleotide encoding a modified (e.g., recombinant) effector of a prolactin protein comprising (i) a janus kinase-2 (JAK2) tyrosine kinase domain, optionally wherein the JAK2 tyrosine kinase domain is fused to a signal transducer and activator of transcription-5 (STAT5) tyrosine kinase domain (e.g., a polynucleotide encoding a JAK2 tyrosine kinase domain linked to the 3' end of a polynucleotide encoding the STAT5 tyrosine kinase domain); and/or (ii) a prolactin receptor intracellular domain fused to a JAK2 tyrosine kinase domain; (e) a loss of function mutation into a circadian related gene PER2 (period circadian protein homolog 2); and/or (f) a polynucleotide encoding one or more glucose transporter genes GLUT1 and/or GLUT12, thereby increasing the rate of nutrient uptake at the basal surface of the monolayer.

Plasma Cells

Plasma cells are derived from a human donor. In some embodiments, the plasma cells are derived from bone marrow, spleen, and/or a lymph node. a primary mammary tissue sample. In certain embodiments, the plasma cells are derived from mucosal epithelial cells other than mammary cells (e.g., from oronasal, gastrointestinal, or respiratory tissue). In some embodiments, the plasma cells are derived from a plasma cell line. In certain embodiments, the plasma cells are derived from a plasmacyte cell line. In some embodiments, the plasma cells are isolated and sorted from non-plasma cells via fluorescence-activated cell sorting, magnetic-activated cell sorting, and/or microfluidic cell sorting. In some embodiments, plasma cells, plasmablasts, or pre-plasmablasts are sorted and isolated by FACS analysis using markers known in the art (e.g., CD38, CD138 and/or CD19). In certain embodiments, the plasma cells are cultivated with the immortalized mammary epithelial cells on a scaffold, thereby producing a cell construct for producing a cultured milk product with secretory products of the plasma cells and mammary cells (e.g., sIgA). In certain embodiments, the plasma cells are grown on a scaffold below a monolayer of mammary cells. In certain embodiments, the plasma cells are grown as dispersed populations of plasma cells overlayed by a monolayer of mammary cells. In certain embodiments, the plasma cells are stimulated to produce immunoglobins during co-culture with mammary cells. In certain embodiments, the plasma cells produce one or more immunoglobins of a class selected from IgG, IgM and IgA. In certain embodiments the plasma cells produce IgA. In certain embodiments, plasma cells produce IgA, and the IgA is processed by mammary epithelial cells to yield sIgA that is bound to secretory component, and the sIgA is secreted by the apical surface of the mammary cells.

Scaffolds

In some embodiments, the cell construct further comprises a scaffold having a top surface/exterior surface and a bottom surface/interior surface. In some embodiments, the scaffold is a 2-dimensional surface or a 3-dimensional surface (e.g., a 3-dimensional micropatterned surface, and/or as a cylindrical structure that is assembled into bundles). A non-limiting example of a 2-dimensional surface scaffold is a Transwell® filter. In some embodiments, the scaffold is a 3-dimensional surface. Non-limiting examples of a 3-dimensional micropatterned surface include a microstructured bioreactor, a decellularized tissue (e.g., a decellularized mammary gland or decellularized plant tissue), micropatterned scaffolds fabricated through casting or three-dimensional printing with biological or biocompatible materials, textured surface. In some embodiments, the scaffold is produced by electrospinning cellulose nanofibers and/or a cylindrical structure that can be assembled into bundles (e.g., a hollow fiber bioreactor). In some embodiments, the scaffold is porous. In some embodiments, the scaffold is a 3D scaffold. In some embodiments, the 3-dimensional scaffold is any structure which has an enclosed hollow interior/central cavity. In some embodiments, the three dimensional scaffold joins with one or more surfaces to form an enclosed interior chamber/basal compartment. For example, the scaffold can join with one or more walls of a bioreactor to form the interior chamber/basal compartment. In some embodiments, the scaffold is a hollow fiber bioreactor. In some embodiments, the 3D scaffold is a tube in which the central cavity is defined by the interior surface of the scaffold. In some embodiments, the 3D scaffold is a hollow sphere in which the central cavity is defined by the interior surface of the scaffold.

For in vitro culture methods for studies of intestinal absorption, 2-dimensional surface scaffold such as Transwells® have long been used as the standard as they provide both apical and basolateral spaces to simulate the gut-blood-barrier and enable both active and passive transport of drugs and nutrients. However, cells seeded onto flat supports exhibit markedly different phenotypes to cells in vivo, partly due to the poor representation of the 3-D extracellular microenvironments.

A 3-dimensional scaffold allows the cells (e.g., MECs and plasma cells) to grow or interact with their surroundings in all three dimensions. Unlike 2D environments, a 3D cell culture allows cells in vitro to grow in all directions, approximating the in vivo mammary environment. Further, the 3D scaffold allows for a larger surface area for culture of the cells and for metabolite and gas exchange, plus it enables necessary compartmentalization—enabling the cultured milk product to be secreted into one compartment, while the cell culture media is contacted with the mammary cells and plasma cells in another compartment. To date, a confluent monolayer with polarized separation of basal and apical cell surfaces using mammary epithelial cell on a 3D surface has not been achieved (Sharfstein et al. 1992).

In some embodiments, the scaffold is porous. In some embodiments, the scaffold is permeable to the cell media, allowing the cell media to contact the cells of the cell monolayer. In some embodiments, the scaffold is transversed by at least one pore that allows the cell media to contact the basal surface of the cells of the cell monolayer.

In some embodiments, the top surface/exterior surface of the scaffold is coated with a matrix material. In some embodiments, the matrix is made up of one or more extracellular matrix proteins. Non-limiting examples of extracellular matrix proteins include collagen, laminin, entactin, tenascin, and/or fibronectin. In some embodiments, the scaffold comprises a natural polymer, a biocompatible synthetic polymer, a synthetic peptide, and/or a composite derived from any combination thereof. In some embodiments, a natural polymer useful with this invention includes, but is not limited to, collagen, chitosan, cellulose, agarose, alginate, gelatin, elastin, heparan sulfate, chondroitin sulfate, keratan sulfate, and/or hyaluronic acid. In some embodiments, a biocompatible synthetic polymer useful with this invention includes, but is not limited to, cellulose, polysulfone, polyvinylidene fluoride, polyethylene co-vinyl acetate, polyvinyl alcohol, sodium polyacrylate, an acrylate polymer, and/or polyethylene glycol. In some embodiments, the top of the scaffold is coated with laminin and collagen.

In some embodiments, the matrix material is porous. In some embodiments, the matrix material is permeable to the cell media, allowing the cell media to contact the cells of the cell monolayer. In some embodiments, the matrix material is transversed by at least one pore that allows the cell media to contact the basal surface of the cells of the cell monolayer.

In some embodiments, the pore size of the scaffold and/or matrix material is at least about 0.1 µm. In some embodiments, the pore size of the scaffold and/or matrix material is at least about 0.2 µm. In some embodiments, the pore size of the scaffold and/or matrix material is at least about 0.3 µm. In some embodiments, the pore size of the scaffold and/or matrix material is at least about 0.4 µm. In some embodiments, the pore size of the scaffold and/or matrix material is at least about 0.5 µm. In some embodiments, the pore size of the scaffold and/or matrix material is at least about 0.6 µm. In some embodiments, the pore size of the scaffold and/or matrix material is at least about 0.7 µm. In some embodiments, the pore size of the scaffold and/or matrix material is at least about 0.8 µm. In some embodiments, the pore size of the scaffold and/or matrix material is at least about 0.9 µm. In some embodiments, the pore size of the scaffold and/or matrix material is at least about 1.0 µm. In some embodiments, the pore size of the scaffold and/or matrix material is at least about 1.1 µm. In some embodiments, the pore size of the scaffold and/or matrix material is at least about 1.2 µm. In some embodiments, the pore size of the scaffold and/or matrix material is at least about 1.3 µm. In some embodiments, the pore size of the scaffold and/or matrix material is at least about 1.4 µm. In some embodiments, the pore size of the scaffold and/or matrix material is at least about 1.5 µm. In some embodiments, the pore size of the scaffold and/or matrix material is at least about 1.6 µm. In some embodiments, the pore size of the scaffold and/or matrix material is at least about 1.7 µm. In some embodiments, the pore size of the scaffold and/or matrix material is at least about 1.8 µm. In some embodiments, the pore size of the scaffold and/or matrix material is at least about 1.9 µm. In some embodiments, the pore size of the scaffold and/or matrix material is at least about 2.0 µm. In some embodiments, the pore size of the scaffold and/or matrix material is at least about 2.1 µm. In some embodiments, the pore size of the scaffold and/or matrix material is at least about 2.2 µm. In some embodiments, the pore size of the scaffold and/or matrix material is at least about 2.2 µm. In some embodiments, the pore size of the scaffold and/or matrix material is at least about 2.3 µm. In some embodiments, the pore size of the scaffold and/or matrix material is at least about 2.4 µm. In some embodiments, the pore size of the scaffold and/or matrix material is at least about 2.5 µm. In some embodiments, the pore size of the scaffold and/or matrix material is at least about 2.6 µm. In some embodiments, the pore size of the scaffold and/or matrix material is at least about 2.7 µm. In some embodiments, the pore size of the scaffold and/or matrix material is at least about 2.8 µm. In some embodiments, the pore size of the scaffold and/or matrix material is at least about 2.9 µm. In some embodiments, the pore size of the scaffold and/or matrix material is at least about 3.0 µm.

In some embodiments, the cell construct comprises: (a) a three dimensional scaffold having an exterior surface, an interior surface defining an interior cavity/basal chamber, and a plurality of pores extending from the interior surface to the exterior surface; (b) a matrix material disposed on the exterior surface of the three-dimensional scaffold; (c) a culture media disposed within the interior cavity/basal chamber and in fluidic contact with the internal surface; (d) a population of plasma cells (PCs) disposed on the matrix material and (e) a continuous monolayer of mammary cells disposed on the population of plasma cells, the mammary cells selected from the group consisting of: (i) mammary epithelial cells, (ii) mammary myoepithelial cells, and (iii) mammary progenitor cells; wherein the continuous monolayer mammary epithelial cells has an apical surface and a basal surface (e.g., the cells form a polarized and confluent cell monolayer).

Bioreactor

Disclosed herein, in certain embodiments, are bioreactors, comprising: (a) an apical compartment comprising a cultured milk product; and (b) at least one cell construct comprising: (a) a three dimensional scaffold having an exterior surface, an interior surface defining an interior cavity/basal chamber, and a plurality of pores extending from the interior surface to the exterior surface; (b) a matrix material disposed on the exterior surface of the three-dimensional scaffold; (c) a culture media disposed within the interior cavity/basal chamber and in fluidic contact with the internal surface; (d) a population of plasma cells (PCs) disposed on the matrix material and (e) a continuous monolayer of mammary cells disposed on the population of plasma cells, the mammary cells selected from the group consisting of: (i) mammary epithelial cells, (ii) mammary myoepithelial cells, and (iii) mammary progenitor cells. In certain embodiments, the cell construct of the bioreactor comprises at least a 70% confluent monolayer of polarized mammary cells disposed on the matrix material, wherein the mammary cells are selected from the group consisting of: mammary epithelial cells, mammary myoepithelial cells, and mammary progenitor cells; wherein the apical surface of the mammary cells is in fluidic contact with the apical compartment.

In some embodiments, the bioreactor is an enclosed bioreactor. In some embodiments, the apical chamber is substantially isolated from the interior cavity/basal compartment.

A hollow fiber bioreactor is an exemplary bioreactor for use with the methods disclosed here. The hollow fiber bioreactor is a high-density, continuous perfusion culture system that closely approximates the environment in which cells grow in vivo. It consists of thousands of semi-permeable 3D scaffolds (i.e., hollow fibers) in a parallel array within a cartridge shell fitted with inlet and outlet ports. These fiber bundles are potted or sealed at each end so that any liquid entering the ends of the cartridge will necessarily flow through the interior of the fibers. Cells are generally seeded outside the fibers within the cartridge in the extra capillary space (ECS).

Three fundamental characteristics differentiate hollow fiber cell culture from other methods: (1) cells are bound to a porous matrix much as they are in vivo, not a plastic dish, microcarrier or other impermeable support, (2) the molecular weight cut off of the support matrix can be controlled, and (3) extremely high surface area to volume ratio (150 cm$^2$ or more per mL) which provides a large area for metabolite and gas exchange for efficient growth of host cells.

The bioreactor structure provides a fiber matrix that allows permeation of nutrients, gases and other basic media components, as well as cell waste products, but not cells, where the cells can be amplified. Hollow fiber bioreactor technology has been used to obtain high density cell amplification by utilizing hollow fibers to create a semi-permeable barrier between the cell growth chamber and the medium flow. Since the surface area provided by this design is large, using this fiber as a culture substrate allows the production of large numbers of cells. Cells growing in the 3-dimensional environment within the bioreactor are bathed in fresh medium as it perfuses through the hollow fibers.

To replicate the topography of the intestine, Costello et al. developed a 3-D printed bioreactor that can both contain porous villus scaffolds via micromolding (Costello et al. 2017 *Scientific Reports* 7(12515): 1-10). This geometrically complex molded scaffold provided separation of the apical and basolateral spaces in a manner in which fluid flow exposes intestinal epithelial cells to physiologically relevant shear stresses (Costello et al. 2017). Similarly, a long-term culture in vitro culture in a simulated gut-like environment was created by Morada et al. using a hollow fiber bioreactor which allowed for two controlled separate environments (biphasic) to provide host cells with oxygen and nutrients from the basal layer, while allowing a low oxygen nutrient rich environment to be developed on the apical surface (Morada et al. 2016 International Journal for Parasitology 26: 21-29).

In configuring the hollow fiber bioreactor, there are design considerations and parameters that can be varied depending upon the goals associated with expansion of the cells. One such design consideration is the size of the pores in the fiber wall. This is generally designed to allow the passage of nutrients to the cells, carry away waste, provide desired products to the cells (such as growth factors), to remove desired products from the cells, and exclude certain factors that may be present from reaching the cells. Accordingly, the pore size of the fiber walls can be varied to modify which components will pass through the walls. For example, pore size can allow the passage of large proteinaceous molecules, including growth factors, including, but not limited to, epidermal growth factor and platelet-derived growth factor. The person of ordinary skill in the art would understand how to vary the pore size depending upon the components that it is desirable to pass through the fiber walls to reach the cells or to carry material from the cells.

In some embodiments, the pore size is about 0.2 µm. In some embodiments, the pore size is about 0.1. In some embodiments, the pore size is about 0.2 µm. In some embodiments, the pore size is about 0.3 µm. In some embodiments, the pore size is about 0.4 µm. In some embodiments, the pore size is about 0.5 µm. In some embodiments, the pore size is about 0.6 µm. In some embodiments, the pore size is about 0.7 µm. In some embodiments, the pore size is about 0.8 µm. In some embodiments, the pore size is about 0.9 µm. In some embodiments, the pore size is about 1.0 µm. In some embodiments, the pore size is about 1.1 µm. In some embodiments, the pore size is about 1.2 µm. In some embodiments, the pore size is about 1.3 µm. In some embodiments, the pore size is about 1.4 µm. In some embodiments, the pore size is about 1.5 µm. In some embodiments, the pore size is about 1.6 µm. In some embodiments, the pore size is about 1.7 µm. In some embodiments, the pore size is about 1.8 µm. In some embodiments, the pore size is about 1.9 µm. In some embodiments, the pore size is about 2.0 µm. In some embodiments, the pore size is about 2.1 µm. In some embodiments, the pore size is about 2.2 µm. In some embodiments, the pore size is about 2.2 µm. In some embodiments, the pore size is about 2.3 µm. In some embodiments, the pore size is about 2.4 µm. In some embodiments, the pore size is about 2.5 µm. In some embodiments, the pore size is about 2.6 µm. In some embodiments, the pore size is about 2.7 µm. In some embodiments, the pore size is about 2.8 µm. In some embodiments, the pore size is about 2.9 µm. In some embodiments, the pore size is about 3.0 µm.

Methods of Making Cell Constructs

Disclosed herein, in certain embodiments, are methods of making a cell construct for producing a cultured milk product comprising immunoglobulins. In some embodiments, the method comprises (a) depositing (i) isolated mammary epithelial cells, mammary myoepithelial cells and/or mammary progenitor cells, and (ii) isolated plasma cells on the upper surface of a scaffold having an upper surface and lower surface to produce a mixed population of plasma cells and mammary cells (i.e., mammary epithelial cells, mammary myoepithelial cells and/or mammary progenitor cells); (b) cultivating the mixed population of mammary cells and plasma cells of (a) on the scaffold, to produce a monolayer of polarized mammary cells located adjacent to and above the plasma cells, wherein the plasma cells are located adjacent to and above the upper surface of the scaffold, wherein the upper surface is located adjacent to and above the lower surface of the scaffold, and wherein the polarized mammary cells comprise an apical surface and a basal surface, thereby producing a cell construct for producing the cultured milk product. In some embodiments, the mammary cells are primary mammary cells. In some embodiments, the mammary cells are derived from a cell culture. In some embodiments, the mammary epithelial cells, myoepithelial cells and/or mammary progenitor cells are isolated from bone marrow, spleen tissue, lymph node tissue, mammary explants from mammary tissue (e.g., breast, udder, teat tissue), or raw breastmilk. In some embodiments, the mammary cells comprise mammary epithelial cells. In some embodiments, the mammary cells, comprise mammary myoepithelial cells. In some embodiments, the mammary cells, comprise mammary progenitor cells. In some embodiments, the plasma cells are isolated from any suitable human tissue or a cell culture. In some embodiments, the mammary cells and plasma cells are deposited concurrently. In some embodiments, the plasma cells are deposited onto the surface of the scaffold prior to the deposition of the mammary cells.

In some embodiments, the method comprises (a) depositing (i) isolated immortalized mammary epithelial cells, mammary myoepithelial cells and/or mammary progenitor cells, and (ii) isolated plasma cells on the upper surface of a scaffold having an upper surface and lower surface to produce a mixed population of plasma cells and immortalized mammary cells (i.e., immortalized mammary epithelial cells, immortalized mammary myoepithelial cells and/or immortalized mammary progenitor cells); (b) cultivating the mixed population of immortalized mammary cells and plasma cells of (a) on the scaffold, to produce a monolayer of polarized immortalized mammary cells located adjacent to and above the plasma cells, wherein the plasma cells are located adjacent to and above the upper surface of the scaffold, wherein the upper surface is located adjacent to and above the lower surface of the scaffold, and wherein the polarized immortalized mammary cells comprise an apical surface and a basal surface, thereby producing a cell construct for producing the cultured milk product. In some embodiments, the immortalized mammary cells comprise immortalized mammary epithelial cells. In some embodiments, the immortalized mammary cells, comprise immortalized mammary myoepithelial cells. In some embodiments, the immortalized mammary cells, comprise immortalized mammary progenitor cells. In some embodiments, the plasma cells are isolated from any suitable human tissue or a cell culture. In some embodiments, the immortalized mammary cells and plasma cells are deposited concurrently. In some embodiments, the plasma cells are deposited onto the surface of the scaffold prior to the deposition of the immortalized mammary cells. In certain embodiments, plasma cells are added to the culture of immortalized mammary epithelial cells to produce a co-culture of mammary cells and plasma cells. In certain embodiments, the plasma cells are cultivated with the immortalized mammary epithelial cells on the scaffold, thereby producing a cell construct for producing a cultured milk product with secretory products of the immune cells and mammary cells (e.g., sIgA). In certain embodiments, the isolated mammary cells are immortalized prior to co-culture of the cells.

In certain embodiments, the immune cells are stimulated to produce immunoglobins during co-culture. In certain embodiments, the immune cells produce one or more immunoglobins of a class selected from IgG, IgM and IgA. In certain embodiments the immune cells produce secretory IgA. Classes of immunoglobins produced by the immune cells include one or more IgA, IgM, and IgG. In certain embodiments, immune cells are co-cultured with MECs in a bioreactor according to methods described herein. In certain embodiments, the bioreactor is a hollow fiber bioreactor described herein.

In certain embodiments, mammary cells are modified and/or stimulated with prolactin according to the methods described herein to stimulate and optimize milk production. In certain embodiments, the mammary cells are modified to express a constitutively active prolactin receptor protein.

In certain embodiments, mammary cells are identified and isolated from mammary tissue samples. In some embodiments, the mammary cells are isolated and sorted via fluorescence-activated cell sorting, magnetic-activated cell sorting, and/or microfluidic cell sorting. In certain embodiments, the mammary epithelial cell populations are sorted by FACS analysis using markers known in the art for identifying the cell populations. In certain embodiments, myoepithelial mammary cells and luminal epithelial mammary cells are isolated by FACS analysis. In certain embodiments, progenitor myoepithelial mammary cells and/or progenitor luminal epithelial mammary cells are isolated by FACS analysis. Any suitable method known in the art for sorting mammary epithelial cells (e.g., luminal epithelial cells), myoepithelial cells, progenitor cells, and immune cells can be used. For example, mammary cells can be sorted using CD24, EPCAM and/or CD49f, cell surface markers.

In some embodiments, plasma cells are identified and isolated from primary mucosal tissue (e.g., oronasal, gastrointestinal, respiratory or mammary). In some embodiments, plasma cells are identified and isolated from primary mammary tissue samples. In some embodiments, the plasma cells are isolated and sorted via fluorescence-activated cell sorting, magnetic-activated cell sorting, and/or microfluidic cell sorting. In certain embodiments, plasma cells are sorted and isolated by FACS analysis. In certain embodiments plasma cells, plasmablasts, or pre-plasmablasts are sorted and isolated by FACS analysis using markers known in the art (e.g., CD20, CD38, CD138 and/or CD19).

In some embodiments, the culturing and/or cultivating of the mammary cells and plasma cells for the cell construct is carried out at a temperature of about 35° C. to about 39° C. (e.g., a temperature of about 35° C., 35.5° C., 36° C., 36.5° C., 37° C., 37.5° C., 38° C., 38.5° C. or about 39° C., or any value or range therein, e.g., about 35° C. to about 38° C., about 36° C. to about 39° C., about 36.5° C. to about 39° C., about 36.5° C. to about 37.5° C., or about 36.5° C. to about 38° C.). In some embodiments, the culturing and/or cultivating is carried out at a temperature of about 37° C.

In some embodiments, the culturing and/or cultivating of the mammary cells and plasma cells for the cell construct is carried out at an atmospheric concentration of C02 of about 4% to about 6%, e.g., an atmospheric concentration of $CO_2$ of about 4%, 4.25%, 4.5%, 4.75%, 5%, 5.25%, 5.5%, 5.75%, or 6% or any value or range therein, e.g., about 4% to about 5.5%, about 4.5% to about 6%, about 4.5% to about 5.5%, or about 5% to about 6%). In some embodiments, the culturing and/or cultivating is carried out at an atmospheric concentration of C02 of about 5%.

In some embodiments, the culturing and/or cultivating of the mammary cells and the plasma cells for the cell construct comprises culturing and/or cultivating in a culture medium that is exchanged about every day to about every 10 days (e.g., every 1 day, every 2 days, every 3 days, every 4 days, every 5 days, every 6 days, every 7 days, every 8 days, every 9 days, every 10 days, or any value or range therein, e.g., about every day to every 3 days, about every 3 days to every 10 days, about every 2 days to every 5 days). In some embodiments, the culturing and/or cultivating further comprises culturing in a culture medium that is exchanged about every day to about every few hours to about every 10 days, e.g., about every 1, 2, 3, 4, 5, 6, 7, 8, 9, 10, 11, 12, 13, 14, 15, 16, 17, 18, 19, 20, 21, 22, 23, or 24 hours to about every 1, 2, 3, 4, 5, 6, 7, 8, 9, or 10 days or any value or range therein. For example, in some embodiments, the culturing and/or cultivating further comprises culturing and/or cultivating in a culture medium that is exchanged about every 12 hours to about every 10 days, about every 10 hours to about every 5 days, or about every 5 hours to about every 3 days.

In some embodiments, the cell construct is stored in a freezer or in liquid nitrogen. The storage temperature depends on the desired storage length. For example, freezer temperature (e.g., storage at a temperature of about 0° C. to about −80° C. or less, e.g., about 0° C., −10° C., −20° C., −30° C., −40° C., −50° C., −60° C., −70° C., −80° C., −90° C., −100° C. or any value or range therein) may be used if the cells are to be used within 6 months (e.g., within 1, 2, 3, 4, 5, or 6 months). For example, liquid nitrogen may be used (e.g., storage at a temperature of −100° C. or less (e.g., about −100° C., −110° C., −120° C., −130, −140, −150, −160, −170, −180, −190° C., −200° C., or less) for longer term storage (e.g., storage of 6 months or longer, e.g., 6, 7, 8, 9, 10, 11, or 12 months, or 1, 2, 3, 4, 5, 6 or more years).

Cultured Milk Products

The present disclosure relates to cultured milk products that comprise protein, lipid, and oligosaccharide components and component concentrations that mimic human breast milk as produced by a lactating female, which compositions are produced, at least in part, by in vitro and/or ex vivo cultured mammary cells.

In some embodiments, two compositionally defined products can be obtained depending on the cellular inputs and culture conditions: (a) a functional nutrition product representing the biosynthetic output of cultured mammary epithelial cells (immortalized or from primary tissue samples); and (b) a similar product further comprising immunoglobulins, produced when plasma cells (PCs) are co-cultured with mammary epithelial cells. Plasma cells can be derived from a primary mammary tissue sample or, e.g., from a plasma cell line.

Contemplated product compositions of the present disclosure can be defined by total levels of protein, lipid, and carbohydrate (Tables 1A-1C) and/or by a signature of specific macronutrient components (Tables 2A-2C) present in concentrations and proportions consistent with human milk.

TABLE 1A

Macromolecular Composition of Functional Nutrition Products Collected from Human Mammary Epithelial Cells Cultured With or Without Plasma Cells.

| Macromolecular Fraction | Concentration, g/L | % wt | Source |
|---|---|---|---|
| Protein | 3-21[a] | 1-44 | MECs |
| Total Immunoglobulin[b] | 0.4-1.8 | 0.14-3.75 | PCs |
| Lipid | 9-135 | 3.1-95+ | MECs |
| HMO | 3.5-21 | 1.2-44 | MECs |
| Lactose | 32-115 | 11-95+ | MECs |
| Total macromolecular content | 48-293 | | MECs ± PCs |
| Energy (kcal/L) | 375-1725 | | |

HMO, human milk oligosaccharide. MEC, mammary epithelial cell; PC, plasma cell.
[a]Non-immunoglobulin protein content.
[b]Formulations lacking immunoglobulin content can be derived from MEC culture in the absence of plasma cells. Formulations with immunoglobulin content can be obtained by coculture of MECs with plasmacytes.
[c]Long-chain fatty acids linoleic acid and alpha-linoleic acid are not synthesized by mammalian cells and are supplemented in cell culture media.

TABLE 1B

Macromolecular Composition of Functional Nutrition Products Collected from Human Mammary Epithelial Cells Cultured With or Without Plasma Cells.

| Macromolecular Fraction | Concentration, g/L | % wt | Source |
|---|---|---|---|
| Protein | 4.5-17.5[a] | 1.8-24 | MECs |
| Total Immunoglobulin[b] | 0.6-1.5 | 0.25-2.1 | PCs |
| Lipid | 13.5-111 | 5.5-95+ | MECs |
| HMO | 5.25-17.5 | 2.2-24 | MECs |
| Lactose | 48-96 | 20-95+ | MECs |
| Total macromolecular content | 71.9-244 | | MECs ± PCs |
| Energy (kcal/L) | 375-1438 | | |

HMO, human milk oligosaccharide. MEC, mammary epithelial cell; PC, plasma cell.
[a]Non-immunoglobulin protein content.
[b]Formulations lacking immunoglobulin content can be derived from MEC culture in the absence of plasma cells. Formulations with immunoglobulin content can be obtained by co-culture of MECs with plasmacytes.
[c]Long-chain fatty acids linoleic acid and alpha-linoleic acid are not synthesized by mammalian cells and are supplemented in cell culture media.

TABLE 1C

Macromolecular Composition of Functional Nutrition Products Collected from Human Mammary Epithelial Cells Cultured With or Without Plasma Cells.

| Macromolecular Fraction | Concentration, g/L | % wt | % vol | Source |
|---|---|---|---|---|
| Protein | 6-14[a] | 3-15 | 1 | MECs |
| Total Immunoglobulin[b] | 0.8-1.2 | 0.4-1.3 | 0.1 | PCs |
| Lipid | 18-89 | 9-92 | 4 | MECs |
| HMO | 7-14 | 4-15 | 2.4 | MECs |
| Lactose | 64-77 | 33-80 | 4.6 | MECs |
| Total macromolecular content | 95.8-195.2 | | 10-15 | MECs ± PCs |
| Energy (kcal/L) | 500-1150 | | | |

HMO, human milk oligosaccharide. MEC, mammary epithelial cell; PC, plasma cell.
[a]Non-immunoglobulin protein content.
[b]Formulations lacking immunoglobulin content can be derived from MEC culture in the absence of plasma cells. Formulations with immunoglobulin content can be obtained by co-culture of MECs with plasmacytes.
[c]Long-chain fatty acids linoleic acid and alpha-linoleic acid are not synthesized by mammalian cells and are supplemented in cell culture media.

In some embodiments, the concentrations of components indicated in Tables 1A-1C can vary, each individually, for example, by having a concentration that is greater than that indicated by 0.1 fold, or 0.2 fold, or 0.3 fold, or 0.4 fold, or 0.5 fold, or 0.6 fold, or 0.7 fold, or 0.8 fold, or 0.9 fold, or 1, 2, 3, 4, 5, 6, 7, 8, 9, or 10 fold.

In some embodiments, the concentrations of components indicated in Tables 1A-1C can vary, each individually, for example, by having a concentration that is less than that indicated by 0.1 fold, or 0.2 fold, or 0.3 fold, or 0.4 fold, or 0.5 fold, or 0.6 fold, or 0.7 fold, or 0.8 fold, or 0.9 fold.

In some embodiments, milk products are contemplated herein that include a subset of the components (i.e., macromolecular fractions) of Tables 1A-1C. In other embodiments, milk products contemplated herein can exclude one or more of the components (i.e., macromolecular fractions) of Tables 1A-1C.

TABLE 2A

Macromolecular Content and Concentration Ranges of Functional Nutrition Products Derived from Human Mammary Epithelial Cells Cultured With or Without Plasma Cells.

| Macromolecular Fraction | Concentration, g/L |
|---|---|
| Protein | |
| P-Casein | 0.25-1.9 |
| K-Casein | 0.25-0.9 |
| a-Casein | 0.05-0.75 |
| a-Lactalbumin | 1.35-4.9 |
| Lysozyme | 0.2-0.75 |
| Lactoferrin | 0.5-3 |
| Haptocorrin | 0.03-1.1 |
| Butyrophilin | 0.02-0.075 |
| Osteopontin | 0.025-0.3 |
| Mucin MC5 | 0.25-0.9 |
| Mucin BrE3 | 0.25-1.1 |
| Lactadherin | 0.03-1.1 |
| Immunoglobulins | 0.1-3 |
| Secretory IgA | 0.1-1.5 |
| | 0.07-2.4 |
| | 0.02-0.45 |
| Total IgA Total IgG Total IgM | 0.005-0.2 |
| Lipids | 2.5-51 |
| Saturated fatty acids | 2-27 |
| Palmitic acid (C16:0) | 0.35-7.5 |
| Stearic acid (C18:0) | 0.25-7.5 |
| Lauric acid (C12:0) | 3.5-69 |
| Monounsaturated fatty acids | 3.5-68 |
| Oleic acid (C18:1 n-9 Z) | 1-30 |

TABLE 2A-continued

Macromolecular Content and Concentration Ranges of Functional Nutrition Products Derived from Human Mammary Epithelial Cells Cultured With or Without Plasma Cells.

| Macromolecular Fraction | Concentration, g/L |
|---|---|
| Polyunsaturated fatty acids | |
| Linoleic acid, LA (C18:2 n-6 Z) | 1-29 |
| | 0.25-1.1 |
| a-Linolenic acid, ALA (C18:3 n-3) | 0.25-1.1 |
| Eicosadienoic acid (C20:2) | 0.25-1.1 |
| Arachidonic acid, AA (C20:4 n-6) | 0.15-.8 |
| Dihomo-γ-linolenic acid, DGLA (C20:3 n-6) | 0.01-0.6 |
| Docosahexadienoic acid, DHA (C22:6 n-3) Cholesterol | 0.045-0.22 |
| Phospholipids, plasmalogens, sphingolipids | 0.05-0.6 |
| Human Milk Oligosaccharides | 0.8-4.8 |
| Neutral | 0.8-4.8 |
| TF-LNH (trifucosyllacto-N-hexose) | 0.8-4.8 |
| 2'-FL (2'-fucosyllactose) | |
| DF-LNHII (difucosyllacto-N-hexaose) | 0.4-2.4 |
| LNFP I (1 acto-A-fucopentaose I) | 0.16-2.4 |
| LNDFHI (lacto-N-difucosylhexaose I) | 0.23-1.8 |
| LNT (lacto-A-tetraose) | 0.4-1.8 |
| LNnT (lacto-A-neotetraose) | 0.08-1.2 |
| DF-L (Difucosyllactose) 3-FL (3-fucosyllactose) Acidic | 0.16-1.8 |
| 6'-SL (6'-sialyllactose) | 0.16-1.44 |
| DS-LNT (disialyllacto-A-tetraose) | 0.04-1.2 |
| FS-LNnH I (fucosyl-sialyl-lacto-N-neohexaose I) LST c (sialyl-lacto-A-tetraose c) | 0.04-0.84 |
| | 0.04-0.84 |
| 3'-SL (3'-sialyllactose) | 0.08-0.36 |
| Lactose | 34-104 |

TABLE 2B

Macromolecular Content and Concentration Ranges of Functional Nutrition Products Derived from Human Mammary Epithelial Cells Cultured With or Without Plasma Cells.

| Macromolecular Fraction | Concentration, g/L |
|---|---|
| | 0.38-1.9 |
| | 0.38-0.75 |
| Protein P-Casein K-Casein a-Casein | 0.08-0.63 |
| a-Lactalbumin | 2.0-4.13 |
| Lysozyme | 0.15-0.63 |
| Lactoferrin | 0.8-2.5 |
| Haptocorrin | 0.05-0.89 |
| Butyrophilin | 0.02-0.063 |
| Osteopontin | 0.04-0.25 |
| Mucin MC5 | 0.38-0.75 |
| Mucin BrE3 | 0.38-0.89 |
| Lactadherin | 0.045-0.09 |
| Immunoglobulins | 0.15-2.5 |
| Secretory IgA | 0.15-1.25 |
| Total IgA | 0.11-2 |
| Total IgG | 0.02-0.38 |
| Total IgM | 0.0075-0.13 |
| Lipids | |
| Saturated fatty acids | 3.75-43 |
| Palmitic acid (C16:0) | 2.25-23 |
| Stearic acid (C18:0) | 0.53-6.3 |
| Lauric acid (C12:0) | 0.38-6.3 |
| Monounsaturated fatty acids | 5.25-58 |
| Oleic acid (C18:1 n-9 Z) | 5.3-56 |
| Polyunsaturated fatty acids | 1.5-25 |
| Linoleic acid, LA (C18:2 n-6 Z) | 1.5-25 |
| a-Linolenic acid, ALA (C18:3 n-3) | 0.38-0.89 |
| Eicosadienoic acid (C20:2) | 0.38-0.89 |
| Arachidonic acid, AA (C20:4 n-6) | 0.38-0.89 |
| Dihomo-γ-linolenic acid, DGLA (C20:3 n-6) | 0.23-0.63 |
| Docosahexadienoic acid, DHA (C22:6 n-3) | 0.015-0.5 |
| Cholesterol | 0.07-0.19 |

TABLE 2B-continued

Macromolecular Content and Concentration Ranges of Functional Nutrition Products Derived from Human Mammary Epithelial Cells Cultured With or Without Plasma Cells.

| Macromolecular Fraction | Concentration, g/L |
|---|---|
| Phospholipids, plasmalogens, sphingolipids | 0.075-0.5 |
| Human Milk Oligosaccharides Neutral | |
| TF-LNH (trifucosyllacto-N-hexose) | 0.9-4.4 |
| 2'-FL (2'-fucosyllactose) | 0.9-4.4 |
| DF-LNHII (difucosyllacto-N-hexaose) | 0.9-4.4 |
| LNFP I (1 acto-A-fucopentaose I) | 0.45-2.2 |
| LNDFHI (lacto-N-difucosylhexaose I) | 0.18-2.2 |
| LNT (lacto-A-tetraose) | 0.27-1.7 |
| LNnT (lacto-A-neotetraose) | 0.4-1.7 |
| DF-L (Difucosyllactose) | 0.09-1.1 |
| 3-FL (3-fucosyllactose) | 0.18-1.7 |
| Acidic | |
| 6'-SL (6'-sialyllactose) | 0.18-1.3 |
| DS-LNT (disialyllacto-A-tetraose) | 0.04-1.1 |
| FS-LNnH I (fucosyl-sialyl-lacto-N-neohexaose I) | 0.04-0.8 |
| LST c (si alyl-lacto-A-tetraose c) | 0.04-0.8 |
| 3'-SL (3'-sialyllactose) | 0.09-0.33 |
| Lactose | 50-98 |

TABLE 2C

Macromolecular Content and Concentration Ranges of Functional Nutrition Products Derived from Human Mammary Epithelial Cells Cultured With or Without Plasma Cells.

| Macromolecular Fraction | Concentration, g/L |
|---|---|
| Protein | |
| P-Casein | 0.5-1.5 |
| K-Casein | 0.5-0.6 |
| a-Casein | 0.1-0.5 |
| a-Lactalbumin | 2.7-3.3 |
| Lysozyme | 0.2-0.5 |
| Lactoferrin | 1-2 |
| Haptocorrin | 0.07-0.7 |
| Butyrophilin | 0.03-0.05 |
| Osteopontin | 0.05-0.2 |
| Mucin MCS | 0.5-0.6 |
| Mucin BrE3 | 0.5-0.7 |
| Lactadherin | 0.06-0.07 |
| Immunoglobulins | 0.2-2 |
| Secretory IgA | 0.2-1.0 |
| Total IgA | 0.15-1.6 |
| Total IgG | 0.03-0.3 |
| Total IgM | 0.01-0.1 |
| Lipids | |
| Saturated fatty acids | 5-34 |
| Palmitic acid (C16:0) | 3-18 |
| Stearic acid (C18:0) | 0.7-5 |
| Lauric acid (C12:0) | 0.5-5 |
| Monounsaturated fatty acids | 7-46 |
| Oleic acid (C18:1 n-9 Z) | 7-45 |
| Polyunsaturated fatty acids | 2-20 |
| Linoleic acid, LA (C18:2n-6 Z) | 2-19 |
| a-Linolenic acid, ALA (C18:3 n-3) | 0.5-0.7 |
| Eicosadienoic acid (C20:2) | 0.5-0.7 |
| Arachidonic acid, AA (C20:4 n-6) | 0.5-0.7 |
| Dihomo-y-linolenic acid, DGLA (C20:3 n-6) | 0.3-0.5 |
| Docosahexadienoic acid, DHA (C22:6 n-3) | 0.02-0.4 |
| Cholesterol | 0.09-0.15 |
| Phospholipids, plasmalogens, sphingolipids | 0.1-0.4 |
| Human Milk Oligosaccharides Neutral | |
| TF-LNH (trifucosyllacto-N-hexose) | 1-4 |
| 2'-FL (2'-fucosyllactose) | 1-4 |
| DF-LNHII (difucosyllacto-N-hexaose) | 1-4 |
| LNFP I (1 acto-A-fucopentaose I) | 0.5-2 |
| LNDFHI (lacto-N-difucosylhexaose I) | 0.2-2 |
| LNT (lacto-A-tetraose) | 0.3-1.5 |

TABLE 2C-continued

Macromolecular Content and Concentration Ranges of Functional Nutrition Products Derived from Human Mammary Epithelial Cells Cultured With or Without Plasma Cells.

| Macromolecular Fraction | Concentration, g/L |
|---|---|
| LNnT (lacto-A-neotetraose) | 0.5-1.5 |
| DF-L (Difucosyllactose) | 0.1-1 |
| 3-FL (3-fucosyllactose) | 0.2-1.5 |
| Acidic | |
| 6'-SL (6'-sialyllactose) | 0.2-1.2 |
| DS-LNT (disialyllacto-A-tetraose) | 0.05-1 |
| FS-LNnH I (fucosyl-sialyl-lacto-N-neohexaose I) | 0.05-0.7 |
| LST c (sialyl-lacto-A-tetraose c) | 0.05-0.7 |
| 3'-SL (3'-sialyllactose) | 0.1-0.3 |
| Lactose | 67-78 |

In some embodiments, the concentrations of components indicated in Tables 2A-C can vary, each individually, for example, by having a concentration that is greater than that indicated by 0.1 fold, or 0.2 fold, or 0.3 fold, or 0.4 fold, or 0.5 fold, or 0.6 fold, or 0.7 fold, or 0.8 fold, or 0.9 fold, or 1, 2, 3, 4, 5, 6, 7, 8, 9, or 10 fold.

In some embodiments, the concentrations of components indicated in Tables 2A-C can vary, each individually, for example, by having a concentration that is less than that indicated by 0.1 fold, or 0.2 fold, or 0.3 fold, or 0.4 fold, or 0.5 fold, or 0.6 fold, or 0.7 fold, or 0.8 fold, or 0.9 fold.

In some embodiments, milk products are contemplated herein that include a subset of the components (i.e., macromolecular fractions) of Tables 2A-C. In other embodiments, milk products contemplated herein can exclude one or more of the components (i.e., macromolecular fractions) of Tables 2A-C.

In some embodiments, milk products are contemplated herein that further comprise serum albumin. In some embodiments, the serum albumin can have a concentration of about 0.025-3.5 g/L. In some embodiments, the serum albumin can have a concentration of about 0.01-2 g/L. In some embodiments, the serum albumin can have a concentration of about 0.15-1 g/L, and in some embodiments, the serum albumin can have a concentration of about 0.2-0.7 g/L.

One aspect of the present disclosure is directed to a milk product comprising about 6-14 grams per liter (g/L) protein components, about 18-89 g/L lipid components, about 7-14 g/L human milk oligosaccharides (HMOs), and about 64-77 g/L lactose, wherein at least one of the protein components, lipid components, HMOs, and lactose is produced by cultured human mammary epithelial cells.

In some embodiments, the protein component comprises about 55-65% dry weight of the milk product. In some embodiments, the protein component comprises one or more of beta-casein, kappa-casein and alpha-casein, and in some embodiments, the beta-casein can have a concentration of about 0.5-1.5 g/L, the kappa-casein can have a concentration of about 0.5-0.6 g/L and the alpha-casein can have a concentration of about 0.1-0.5 g/L in the milk product. In some embodiments of the milk product, the beta-casein, kappa-casein and alpha-casein together comprise about 35-45% dry weight percent of the protein component. In some embodiments, the beta-casein comprises greater than about 50% of total casein content.

In some embodiments, the protein component further comprises, for example, one or more of alpha-lactalbumin, lysozyme, lactoferrin, haptocorrin, butyrophilin, osteopontin, mucin MC5, mucin BrE3, and lactadherin. Some embodiments further comprise serum albumin. In some embodiments of the milk product, the alpha-lactalbumin can have a concentration of about 2.7-3.3 g/L, and in some embodiments, the lysozyme can have a concentration of about 0.2-0.5 g/L, and in some embodiments, the lactoferrin can have a concentration of about 1.0-2.0 g/L. In some embodiments, the haptocorrin can have a concentration of about 0.07-0.7 g/L, and in some embodiments, the butyrophilin can have a concentration of about 0.03-0.05 g/L. In some embodiments, the osteopontin can have a concentration of about 0.05-0.2 g/L, and in some embodiments, the mucin MC5 can have a concentration of about 0.5-0.6 g/L. In some embodiments, the mucin BrE3 can have a concentration of about 0.5-0.7 g/L, and in some embodiments, the lactadherin can have a concentration of about 0.06-0.07 g/L. In some embodiments serum albumin can have a concentration of about 0.025-3.5 g/L, or about 0.01-2 g/L, or about 0.15-1 g/L, or about 0.2-0.7 g/L In some embodiments of the milk product, the protein components are of human origin.

In some embodiments, the lipid component comprises one or more of saturated fatty acids, monounsaturated fatty acids, polyunsaturated fatty acids, cholesterol, phospholipids, plasmalogens, and sphingolipids. In some embodiments of the milk product, the saturated fatty acids can have a concentration of about 5-34 g/L. The saturated fatty acids can comprise, for example, one or more of palmitic acid, stearic acid and lauric acid and combinations thereof. In some embodiments, the palmitic acid comprises at least about 50% sn-2 form. In some embodiments of the milk product, palmitic acid can have a concentration of about 3-18 g/L, in some embodiments, stearic acid can have a concentration of about 0.7-5 g/L, and in some embodiments, lauric acid can have a concentration of about 0.5-5 g/L.

In some embodiments, monounsaturated fatty acids can have a concentration of about 7-46 g/L of the milk product. The saturated fatty acid component can comprise, for example, oleic acid, in some embodiments, the oleic acid comprises at least about 50% sn-1 form, and in some embodiments, oleic acid can have a concentration of about 7-45 g/L in the milk product.

In some embodiments of the milk product, polyunsaturated fats can have a concentration of about 2-20 g/L. The polyunsaturated fats can comprise, for example, one or more of linoleic acid, alpha-linolenic acid, eicosadienoic acid, arachidonic acid, dihomo-gamma-linolenic acid, and docosahexadienoic acid. In some embodiments, the linoleic acid comprises at least about 50% sn-3 form, and in some embodiments, linoleic acid can have a concentration of about 2-19 g/L, and in some embodiments, alpha-linolenic acid can have a concentration of about 0.5-0.7 g/L. In some embodiments, eicosadienoic acid can have a concentration of about 0.5-0.7 g/L, and in some embodiments arachidonic acid can have a concentration of about 0.50.7 g/L. In some embodiments, dihomo-gamma-linolenic acid can have a concentration of about 0.3-0.5 g/L, and in some embodiments, docosahexadienoic acid can have a concentration of about 0.02-0.4 g/L. Some embodiments of the milk product comprise all of the above polyunsaturated fats, wherein linoleic acid can have a concentration of about 2-19 g/L, alphalinolenic acid can have a concentration of about 0.5-0.7 g/L, eicosadienoic acid can have a concentration of about 0.5-0.7 g/L, arachidonic acid can have a concentration of about 0.5-0.7 g/L, dihomo-gamma-linolenic acid can have a concentration of about 0.3-0.5 g/L, and docosahexadienoic acid can have a concentration of about 0.02-0.4 g/L in the milk product.

In some embodiments, cholesterol can have a concentration of about 0.09-0.15 g/L in milk product, and in some embodiments, phospholipids, plasmalogens, and sphingolipids together can have a concentration of about 0.1-0.4 g/L in the milk product.

In some embodiments, the milk product comprises one or more neutral oligosaccharides, one or more acidic oligosaccharides or one or more each of neutral oligosaccharides and acidic oligosaccharides.

In some embodiments, the one or more neutral oligosaccharides comprise TF-LNH (trifucosyllacto-N-hexose), 2'-FL (2'-fucosyllactose), DF-LNHII (difucosyllacto-N-hexaose), LNFP I (lacto-N-fucopentaose I), LNDFHI (lacto-N-difucosylhexaose I), LNT (lacto-N-tetraose), LNnT (lacto-N-neotetraose), DF-L (Difucosyllactose), and 3-FL (3-fucosyllactose).

In some embodiments, the one or more acidic oligosaccharides comprise 6'-SL (6'-sialyllactose), DS-LNT (disialyllacto-N-tetraose), FS-LNnH I (fucosyl-sialyl-lacto-N-neohexaose I), LST c (sialyl-lacto-N-tetraose c), and 3'-SL (3'-sialyllactose).

In some embodiments, the one or more neutral oligosaccharides comprises TF-LNH (trifucosyllacto-N-hexose), which oligosaccharide can have a concentration of about 1-4 g/L in the milk product. In some embodiments, the one or more neutral oligosaccharides comprises 2'-FL (2'-fucosyllactose), which oligosaccharide can have a concentration of about 1-4 g/L in the milk product, and in some embodiments, the one or more neutral oligosaccharides comprises DF-LNH II (difucosyllacto-N-hexaose), which oligosaccharide can have a concentration of about 1-4 g/L in the milk product. In some embodiments, the one or more neutral oligosaccharides comprises LNFP I (lacto-N-fucopentaose I), which oligosaccharide can have a concentration of about 0.5-2 g/L in the milk product, and in some embodiments, the one or more neutral oligosaccharides comprises LNDFH I (lacto-N-difucosylhexaose I), which oligosaccharide can have a concentration of about 0.2-2 g/L in the milk product. In some embodiments, the one or more neutral oligosaccharides comprises LNT (lacto-N-tetraose), which oligosaccharide can have a concentration of about 0.3-1.5 g/L in the milk product, and in some embodiments, the one or more neutral oligosaccharides comprises LNnT (lacto-N-neotetraose), which oligosaccharide can have a concentration of about 0.5-1.5 g/L in the milk product. In some embodiments, the one or more neutral oligosaccharides comprises DF-L (Difucosyllactose), which oligosaccharide can have a concentration of about 0.1-1 g/L in the milk product, and in some embodiments, the one or more neutral oligosaccharides comprises 3-FL (3-fucosyllactose), which oligosaccharide can have a concentration of about 0.2-1.5 g/L of the milk product.

In some embodiments, the one or more acidic oligosaccharides comprises 6'-SL (6'-sialyllactose), which oligosaccharide can have a concentration of about 0.2-1.2 g/L in the milk product, and in some embodiments, the one or more acidic oligosaccharides comprises DS-LNT (disialyllacto-N-tetraose), which oligosaccharide can have a concentration of about 0.05-1 g/L in the milk product. In some embodiments, the one or more acidic oligosaccharides comprises FS-LNnH I (fucosyl-sialyl-lacto-N-neohexaose I), which oligosaccharide can have a concentration of about 0.05-0.7 g/L in the milk product, and in some embodiments, the one or more acidic oligosaccharides comprises LST c (sialyl-lacto-N-tetraose c), which oligosaccharide can have a concentration of about 0.05-0.7 g/L in the milk product. In some embodiments, the one or more acidic oligosaccharides comprises 3'-SL (3'-sialyllactose), which oligosaccharide can have a concentration of about 0.1-0.3 g/L in the milk product.

In some embodiments of the milk product the one or more neutral oligosaccharides comprise TF-LNH (trifucosyllacto-N-hexose), 2'-FL (2'-fucosyllactose), DF-LNH II (difucosyllacto-N-hexaose), LNFP I (lacto-N-fucopentaose I), LNDFHI (lacto-N-difucosylhexaose I), LNT (lacto-N-tetraose), LNnT (lacto-N-neotetraose), DF-L (Difucosyllactose), and 3-FL (3-fucosyllactose) and the one or more acidic oligosaccharides comprises 6'-SL (6'-sialyllactose), DS-LNT (disialyllacto-N-tetraose), FS-LNnH I (fucosyl-sialyl-lacto-N-neohexaose I), LST c (sialyl-lacto-N-tetraose c), and 3'-SL (3'-sialyllactose).

In some embodiments, the milk product comprises about 1-4 g/L TF-LNH (trifucosyllacto-N-hexose), comprises about 1-4 g/L 2'-FL (2'-fucosyllactose), comprises about 1-4 g/L DF-LNH II (difucosyllacto-N-hexaose), comprises about 0.5-2 g/L LNFP I (lacto-N-fucopentaose I), comprises about 0.2-2 g/L LNDFH I (lacto-N-difucosylhexaose I), comprises about 0.3-1.5 g/L LNT (lacto-N-tetraose), comprises about 0.5-1.5 g/L LNnT (lacto-N-neotetraose), comprises about 0.1-1 g/L DF-L (Difucosyllactose), comprises about 0.2-1.5 g/L 3-FL (3-fucosyllactose), comprises about 0.2-1.2 g/L 6'-SL (6'-sialyllactose), comprises about 0.05-1 g/L DS-LNT (disialyllacto-N-tetraose), comprises about 0.05-0.7 g/L FS-LNnH I (fucosyl-sialyl-lacto-N-neohexaose I), comprises about 0.05-0.7 g/L LST c (sialyl-lacto-N-tetraose c), and comprises about 0.1-0.3 g/L 3'-SL (3'-sialyllactose).

In some embodiments, the neutral oligosaccharides content comprises at least about 2-fold, or about 3-fold, or about 4-fold, or about 5-fold, or about 6-fold, or about 7-fold, or about 8-fold, or about 9-fold, or about 10-fold, or about 11-fold, or about 12-fold, or about 13-fold, or about 14-fold, or about 15-fold more by weight than acidic oligosaccharide content.

In another aspect of the disclosure, a milk product is provided, comprising about 614 grams per liter (g/L) protein components, about 18-89 g/L lipid components, about 7-14 g/L human milk oligosaccharides (HMOs), and about 64-77 g/L lactose, wherein the protein components comprise one or more of beta-casein, kappa-casein, and alpha-casein, alphalactalbumin, lysozyme, lactoferrin, haptocorrin, butyrophilin, osteopontin, mucin MC5, mucin BrE3, and lactadherin, wherein the lipid components comprise one or more of palmitic acid, stearic acid and lauric acid, oleic acid, linoleic acid, alpha-linolenic acid, eicosadienoic acid, arachidonic acid, dihomo-gamma-linolenic acid, docosahexadienoic acid, cholesterol, phospholipids, plasmalogens and sphingolipids, wherein the human milk oligosaccharides comprise one or more of TF-LNH (trifucosyllacto-N-hexose), 2'-FL (2'-fucosyllactose), DF-LNHII (difucosyllacto-N-hexaose), LNFP I (lacto-N-fucopentaose I), LNDFHI (lacto-N-difucosylhexaose I), LNT (lacto-N-tetraose), LNnT (lacto-N-neotetraose), DF-L (Difucosyllactose), and 3-FL (3-fucosyllactose), 6'-SL (6'-sialyllactose), DS-LNT (disialyllacto-N-tetraose), FS-LNnH I (fucosyl-sialyl-lacto-N-neohexaose I), LST c (sialyl-lacto-N-tetraose c), and 3'-SL (3'-sialyllactose), and wherein at least one of the protein components, lipid components, HMOs, and lactose is produced by cultured human mammary epithelial cells. In some embodiments, the milk product further comprises serum albumin.

In some embodiments, the milk product comprises about 0.5-1.5 g/L beta-casein, comprises about 0.5-0.6 g/L kappa-casein, comprises about 0.1-0.5 g/L alpha-casein, comprises about 2.7-3.3 g/L alpha-lactalbumin, comprises about 0.2-0.5 g/L lysozyme, comprises about 1.0-2.0 g/L lactoferrin, comprises about 0.07-0.7 g/L haptocorrin, comprises about 0.03-0.05 g/L butyrophilin, comprises about 0.05-0.2 g/L osteopontin, comprises about 0.5-0.6 g/L mucin MC5, comprises about 0.5-0.7 g/L mucin BrE3, comprises about 0.06-0.07 g/L lactadherin, comprises about 2-19 g/L linoleic acid, comprises about 0.5-0.7 g/L alpha-linolenic acid, comprises about 0.5-0.7 g/L eicosadienoic acid, comprises about 0.5-0.7 g/L arachidonic acid, comprises about 0.3-0.5 g/L dihomo-gamma-linolenic acid, comprises about 0.02-0.4 g/L docosahexadienoic acid, comprises about 0.09-0.15 g/L cholesterol, together comprise about 0.1-0.4 g/L phospholipids, plasmalogens and sphingolipids, comprises about 1-4 g/L TF-LNH (trifucosyllacto-N-hexose), comprises about 1-4 g/L 2'-FL (2'-fucosyllactose), comprises about 1-4 g/L DF-LNH II (difucosyllacto-N-hexaose), comprises about 0.5-2 g/L LNFP I (lacto-N-fucopentaose I), comprises about 0.2-2 g/L LNDFHI (lacto-N-difucosylhexaose I), comprises about 0.3-1.5 g/L LNT (lacto-N-tetraose), comprises about 0.5-1.5 g/L LNnT (lacto-N-neotetraose), comprises about 0.1-1 g/L DF-L (Difucosyllactose), comprises about 0.2-1.5 g/L 3-FL (3-fucosyllactose), comprises about 0.2-1.2 g/L 6'-SL (6'-sialyllactose), comprises about 0.05-1 g/L DS-LNT (disialyllacto-N-tetraose), comprises about 0.05-0.7 g/L FS-LNnH I (fucosyl-sialyl-lacto-N-neohexaose I), comprises about 0.05-0.7 g/L LST c (sialyl-lacto-N-tetraose c), and comprises about 0.1-0.3 g/L 3'-SL (3'-sialyllactose). In some embodiments, the milk product further comprises serum albumin, which serum albumin has a concentration of about 0.025-3.5 g/L, or about 0.01-2 g/L, or about 0.15-1 g/L, or about 0.3-0.7 g/L.

In another aspect of the disclosure, a milk product is provided comprising about 3-15 percent protein by weight, about 9-92 percent lipid by weight, about 4-15 percent by weight human milk oligosaccharides (HMOs), and about 33-80 percent by weight lactose, wherein at least one of the protein, lipid, HMOs, and lactose is produced by cultured human mammary epithelial cells.

In some embodiments of some aspects of the disclosure, the milk product comprises at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% of the overall macromolecular composition of human breast milk.

In some embodiments of the milk product of the disclosure, non-protein nitrogen content is at least about 10%, or at least about 15%, or at least about 20%, or at least about 25%, or at least about 30% of total nitrogen content.

In some embodiments, the milk product comprises about 500-1150 kcal/L available energy content, and in some embodiments, between about 40-55% of the available energy content is from lipids. In some embodiments, the milk product comprises between about 95.8 and 195.2 g/L macromolecular content.

In another aspect of the disclosure, a containerized milk product is provided, comprising the milk product according to some embodiments of the disclosure that is packaged into a container.

In another aspect of the disclosure, a frozen milk product is provided, comprising the milk product according to some embodiments of the disclosure that has been frozen. In some embodiments, the frozen milk product is packaged into a container making a containerized frozen milk product.

In another aspect of the disclosure, a lyophilized milk product is provided, comprising the milk product according to some embodiments of the disclosure that has been lyophilized. In some embodiments, the lyophilized milk product is packaged into a container making a containerized lyophilized milk product.

In another aspect of the disclosure, an extracted milk product is provided, comprising one or more components extracted from the milk product according to some embodiments of the disclosure. Non-limiting examples of components that can be extracted from the milk product include protein, lipid, carbohydrate, vitamin, and/or mineral content. In some embodiments, the one or more components extracted from the collected milk product are lyophilized or concentrated to produce a lyophilized or a concentrated extracted milk product component. In some embodiments, the one or more components extracted from the collected milk product are concentrated by membrane filtration or reverse osmosis, while in other embodiments, the whole, un-extracted milk product is concentrated by membrane filtration or reverse osmosis. In some embodiments, the one or more extracted components from the collected milk product comprise milk protein, lipid, carbohydrate, vitamin, and minerals. In some embodiments, the one or more extracted milk product components are packaged in a container, and in some embodiments, concentrated whole, un-extracted milk product is packaged in a container.

In some embodiments, the container is sterile, vacuum-sealed, or classified as food grade, or any combination thereof. Non-limiting examples of containers comprise a canister, a jar, a bottle, a bag, a box, or a pouch. In some embodiments, the container is a canister, a jar, a bottle, a bag, a box, or a pouch.

Immunoglobulins

In some embodiments, the cultured milk product further comprises one or more immunoglobulins or sIA. In some embodiments, the cultured milk product comprises one or more of IgA, IgG, and IgM. In some embodiments, the cultured milk product comprises IgA2 (secretory) and IgA1 (non-secretory). In some embodiments, the plasma cells of the cell construct produce IgA and the mammary epithelial cells process the IgA to yield sIgA (IgA2). sIgA comprises a secretory component, the extracellular domain of the polymeric Ig receptor, attached to an IgA. Mammary epithelial cells process IgA by cleaving the extracellular domain of a polymeric Ig receptor to generate sIgA. In some embodiments, sIgA is secreted from the apical surface of the mammary epithelial cell.

In certain embodiments, the immunoglobulins bind to an antigen of a microorganism (i.e., bacterium or virus). In certain embodiments, the immunoglobulins bind to viral or bacterial antigens capable of causing an infectious disease in humans. In certain embodiments, the immunoglobulins bind to viral or bacterial antigens that cause infections of respiratory or gastrointestinal epithelium. In certain embodiments, the immunoglobulins bind antigens from microorganisms that cause enterocolitis or sepsis in infants.

In certain embodiments, the milk product comprises about 0.2-1.0 g/L secretory IgA. In certain embodiments, the milk product comprises about 0.2, 0.25, 0.3, 0.35, 0.4, 0.45, 0.5, 0.55, 0.6, 0.65, 0.7, 0.75, 0.8, 0.85, 0.9, 0.95, or 1.0 g/L secretory IgA. In certain embodiments, the milk product comprises about 0.15-1.6 g/L total IgA. In certain embodiments, the milk product comprises about 0.15, 0.2, 0.25, 0.3, 0.35, 0.4, 0.45, 0.5, 0.55, 0.6, 0.65, 0.7, 0.75, 0.8, 0.85, 0.9, 0.95, 1.0, 1, 05, 1.1, 1.15, 1, 2, 1.25, 1.3, 1.35, 1.4, 1.45, 1.5, 1.55, or 1.6 g/L total IgA.

In some embodiments that comprise IgG, the milk product comprises about 0.03-0.3 g/L IgG. In certain embodiments, that comprise IgG, the milk product comprises about 0.03, 0.04, 0.05, 0.06, 0.07, 0.08, 0.09, 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.3 g/L. In some embodiments that comprise IgM, the milk product comprises about 0.01-0.1 g/L IgM. In certain embodiments, the milk product comprises about 0.01, 0.02, 0.03, 0.04, 0.05, 0.06, 0.07, 0.08, 0.09, 0.1, 0.1 g/L IgM. In some embodiments, the milk product comprises about 0.2-2.0 percent by weight total immunoglobulins. In certain embodiments, the milk product comprises 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0 percent by weight total immunoglobulins.

Included herein are immunotherapeutic compositions comprising (a) IgA and sIgA derived from the secreted products of mammary epithelial cells co-cultured with plasma cells, and (b) a pharmaceutically acceptable excipient. In some embodiments, the IgA and sIgA are isolated from the product resulting from co-culturing mammary epithelial cells and plasma cells (e.g., a cultured milk product).

In some embodiments, IgA is produced by the plasma cells in the cell construct. The IgA binds to a receptor (polymeric Ig receptor) on the basal surface of mammary epithelial cells. The IgA and receptor are transported into the mammary epithelial cells. The mammary cells process the IgA. The extracellular domain of the receptor bound to the IgA (secretory component) is cleaved by a proteinase within the mammary epithelial cells and the IgA bound to secretory component is secreted from the apical surface of the mammary epithelial cells to yield sIgA. In some embodiments, the sIgA is secreted as part of the cultured milk product from the apical surface of the mammary cells into the apical compartment. In some embodiments, the sIgA is isolated from the cultured milk product. In some embodiments, the sIgA is not isolated from the cultured milk product.

Basal Culture Media and Lactouenic Media

In some embodiments, the culture medium comprises a carbon source, a chemical buffering system, one or more essential amino acids, one or more vitamins and/or cofactors, and one or more inorganic salts. In some embodiments, the carbon source, chemical buffering system, one or more essential amino acids, one or more vitamins and/or cofactors, and/or one or more inorganic salts are food grade.

In some embodiments, the culture medium is lactogenic culture medium. In some embodiments, the culture medium further comprises prolactin (e.g., mammalian prolactin, e.g., human prolactin), linoleic and alpha-linoleic acid, estrogen and/or progesterone. For example, in some embodiments, the culture medium comprises prolactin (or prolactin is added) in an amount from about 20 ng/mL to about 200 ng/L of culture medium, e.g., about 20, 30, 40, 50, 60, 70, 80, 90, 100, 110, 120, 130, 140, 150, 160, 170, 180, 190, or 200 ng/mL or any value or range therein. In some embodiments, the culture medium comprises prolactin (or prolactin is added) in an amount from about 20 ng/mL to about 195 ng/mL, about 50 ng/mL to about 150 ng/mL, about 25 ng/mL to about 175 ng/mL, about 45 ng/mL to about 200 ng/mL, or about 75 ng/mL to about 190 ng/mL of culture medium. In some embodiments, the culture medium further comprises other factors to improve efficiency, including, but not limited to, insulin, an epidermal growth factor, and/or a hydrocortisone.

In some embodiments, the culture medium comprises a carbon source in an amount from about 1 g/L to about 15 g/L of culture medium (e.g., about 1, 2, 3, 4, 5, 6, 7, 8, 9, 10, 11, 12, 13, 14 or 15 g/L or any value or range therein), or about 1, 2, 3, 4, 5 or 6 g/L to about 7, 8, 9, or 10, 11, 12, 13, 14 or 15 g/L of the culture medium. Non-limiting examples of a carbon source include glucose and/or pyruvate. For example, in some embodiments, the culture medium comprises glucose in an amount from about 1g/L to about 12 g/L of culture medium, e.g., about 1, 2, 3, 4, 5, 6, 7, 8, 9, 10, 11, or 12 g/L or any value or range therein. In some embodiments, the culture medium comprises glucose in an amount from about 1 g/L to about 6 g/L, about 4 g/L to about 12 g/L, about 2.5 g/L to about 10.5 g/L, about 1.5 g/L to about 11.5 g/L, or about 2 g/L to about 10 g/L of culture medium. In some embodiments, the culture medium comprises glucose in an amount from about 1, 2, 3, or 4 g/L to about 5, 6, 7, 8, 9, 10, 11, or 12 g/L or about 1, 2, 3, 4, 5, or 6 g/L to about 7, 8, 9, 10, 11, or 12 g/L. In some embodiments, the culture medium comprises pyruvate in an amount from about 5 g/L to about 15 g/L of culture medium, e.g., about 5, 6, 7, 8, 9, 10, 11, 12, 13, 14, or 15 g/L or any value or range therein. In some embodiments, the culture medium comprises pyruvate in an amount from about 5 g/L to about 14.5 g/L, about 10 g/L to about 15 g/L, about 7.5 g/L to about 10.5 g/L, about 5.5 g/L to about 14.5 g/L, or about 8 g/L to about 10 g/L of culture medium. In some embodiments, the culture medium comprises pyruvate in an amount from about 5, 6, 7, or 8 g/L to about 9, 10, 11, 12, 13, 14 or 15 g/L or about 5, 6, 7, 8, 9, or 10 g/L to about 11, 12, 13, 14 or 15 g/L.

In some embodiments, the culture medium comprises a chemical buffering system in an amount from about 1 g/L to about 4 g/L (e.g., about 1, 1.5, 2, 2.5, 3, 3.5, or 4 g/L or any value or range therein) of culture medium or about 10 mM to about 25 mM (e.g., about 10, 11, 12, 13, 14, 15, 16, 17, 18, 19, 20, 21, 22, 23, 24, or 25 mM or any value or range therein). In some embodiments, the chemical buffering system includes, but is not limited to, sodium bicarbonate and/or 4-(2-hydroxyethyl)-1-piperazineethanesulfonic acid (HEPES). For example, in some embodiments, the culture medium comprises sodium bicarbonate in an amount from about 1 g/L to about 4 g/L of culture medium, e.g., about 1, 1.5, 2, 2.5, 3, 3.5, or 4 g/L or any value or range therein. In some embodiments, the culture medium comprises sodium bicarbonate in an amount from about 1 g/L to about 3.75 g/L, about 1.25 g/L to about 4 g/L, about 2.5 g/L to about 3 g/L, about 1.5 g/L to about 4 g/L, or about 2 g/L to about 3.5 g/L of culture medium. In some embodiments, the culture medium comprises HEPES in an amount from about 10 mM to about 25 mM, e.g., about 10, 11, 12, 13, 14, 15, 16, 17, 18, 19, 20, 21, 22, 23, 24, or 25 mM or any value or range therein. In some embodiments, the culture medium comprises HEPES in an amount from about 11 mM to about 25 mM, about 10 mM to about 20 mM, about 12.5 mM to about 22.5 mM, about 15 mM to about 20.75 mM, or about 10 mM to about 20 mM.

In some embodiments, the culture medium comprises one or more essential amino acids in an amount from about 0.5 mM to about 5 mM (e.g., about 0.5, 1, 1.5, 2, 2.5, 3, 3.5, 4, 4.5, or 5 mM or any value or range therein) or about 0.5, 1, 1.5, 2 mM to about 2.5, 3, 3.5, 4, 4.5, or 5 mM. In some embodiments, the one or more essential amino acids is histidine, isoleucine, leucine, lysine, methionine, phenylalanine, threonine, tryptophan, valine, and/or arginine. For example, in some embodiments, the culture medium comprises arginine in an amount from about 0.5 mM to about 5 mM, e.g., about 0.5, 1, 1.5, 2, 2.5, 3, 3.5, 4, 4.5, or 5 mM or any value or range therein. In some embodiments, the culture medium comprises an essential amino acids in an amount from about 0.5 mM to about 4.75 mM, about 2 mM to about 3.5 mM, about 0.5 mM to about 3.5 mM, about 1 mM to about 5 mM, or about 3.5 mM to about 5 mM.

In some embodiments, the culture medium comprises one or more vitamins and/or cofactors in an amount from about 0.01 µM to about 50 µM (e.g., about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 3, 4, 5, 6, 7, 8, 9, 10, 12.5, 15, 17.5, 20, 25, 30, 35, 40, 45, 46, 47, 48, 49, 49.025, 49.05, 49.075, or 50 µM or any value or range therein) or about 0.01, 0.02, 0.03, 0.04, 0.05, 0.06, 0.07, 0.08, 0.09, 0.1, 0.2, 0.3, 0.4, 0.5, 0.6, 0.7, 0.8, or 0.9 µM to about 1, 1.1, 1.2, 1.3, 1.4, 1.5, 1.6, 1.7, 1.8, 1.9, 2, 2.1, 2.2, 2.3, 2.4, 2.5, 3, 4, 5, 6 µM or about 0.02, 0.025, 0.05, 0.075, 1, 1.5, 2, 3, 4, 5, 6, 7, 8, 9, 10 µM to about 12.5, 15, 17.5, 20, 25, 30, 35, 40, 45, 46, 47, 48, 49, 49.025, 49.05, 49.075, or 50 µM. In some embodiments, one or more vitamins and/or cofactors include, but are not limited to, thiamine and/or riboflavin. For example, in some embodiments, the culture medium comprises thiamine in an amount from about 0.025 µM to about 50 µM, e.g., about 0.025, 0.05, 0.075, 1, 1.5, 2, 3, 4, 5, 6, 7, 8, 9, 10, 12.5, 15, 17.5, 20, 25, 30, 35, 40, 45, 46, 47, 48, 49, 49.025, 49.05, 49.075, or 50 µM or any value or range therein. In some embodiments, the culture medium comprises thiamine in an amount from about 0.025 µM to about 45.075 µM, about 1 µM to about 40 µM, about 5 µM to about 35.075 µM, about 10 µM to about 50 µM, or about 0.05 µM to about 45.5 µM. In some embodiments, the culture medium comprises riboflavin in an amount from about 0.01 µM to about 3 µM, e.g., about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, or 3 µM or any value or range therein. In some embodiments, the culture medium comprises riboflavin in an amount from about 0.01 µM to about 2.05 µM, about 1 µM to about 2.95 µM, about 0.05 µM to about 3 µM, about 0.08 µM to about 1.55 µM, or about 0.05 µM to about 2.9 µM.

In some embodiments, the culture medium comprises one or more inorganic salts in an amount from about 100 mg/L to about 150 mg/L of culture medium (e.g., about 100, 105, 110, 115, 120, 125, 130, 135, 140, 145, or 150 mg/L or any value or range therein) or about 100 mg/L to about 150 mg/L of culture medium (e.g., about 100, 105, 110, 115, 120, 125, 130, 135, 140, 145, or 150 mg/L or any value or range therein). In some embodiments, one or more inorganic salts include, but are not limited to, calcium and/or magnesium. For example, in some embodiments, the culture medium comprises calcium in an amount from about 100 mg/L to about 150 mg/L of culture medium, e.g., about 100, 105, 110, 115, 120, 125, 130, 135, 140, 145, or 150 mg/L or any value or range therein. In some embodiments, the culture medium comprises arginine in an amount from about 100 mg/L to about 125 mg/L, about 105 mg/L to about 150 mg/L, about 120 mg/L to about 130 mg/L, or about 100 mg/L to about 145 mg/L of culture medium. In some embodiments, the culture medium comprises magnesium in an amount from about 0.01 mM to about 1 mM, e.g., about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 0.91, 0.92, 0.93, 0.94, 0.95, 0.96, 0.97, 0.98, 0.99, or 1 mM or any value or range therein. In some embodiments, the culture medium comprises magnesium in an amount from about 0.05 mM to about 1 mM, about 0.01 mM to about 0.78 mM, about 0.5 mM to about 1 mM, about 0.03 mM to about 0.75 mM, or about 0.25 mM to about 0.95 mM.

In some embodiments, the culture medium comprises a carbon source in an amount from about 1 g/L to about 15 g/L of culture medium (e.g., about 1, 2, 3, 4, 5, 6, 7, 8, 9, 10, 11, 12, 13, 14 or 15 g/L or any value or range therein), or about 1, 2, 3, 4, 5 or 6 g/L to about 7, 8, 9, or 10, 11, 12, 13, 14 or 15 g/L of the culture medium. In some embodiments, the carbon source includes, but is not limited to, glucose and/or pyruvate. For example, in some embodiments, the culture medium comprises glucose in an amount from about 1 g/L to about 12 g/L of culture medium, e.g., about 1, 2, 3, 4, 5, 6, 7, 8, 9, 10, 11, or 12 g/L or any value or range therein. In some embodiments, the culture medium comprises glucose in an amount from about 1 g/L to about 6 g/L, about 4 g/L to about 12 g/L, about 2.5 g/L to about 10.5 g/L, about 1.5 g/L to about 11.5 g/L, or about 2 g/L to about 10 g/L of culture medium. In some embodiments, the culture medium comprises pyruvate at an amount of about 5 g/L to about 15 g/L of culture medium, e.g., about 5, 6, 7, 8, 9, 10, 11, 12, 13, 14, or 15 g/L or any value or range therein. In some embodiments, the culture medium comprises pyruvate in an amount from about 5 g/L to about 14.5 g/L, about 10 g/L to about 15 g/L, about 7.5 g/L to about 10.5 g/L, about 5.5 g/L to about 14.5 g/L, or about 8 g/L to about 10 g/L of culture medium.

In some embodiments, the culture medium comprises a chemical buffering system in an amount from about 1 g/L to about 4 g/L (e.g., about 1, 1.5, 2, 2.5, 3, 3.5, or 4 g/L or any value or range therein) of culture medium or about 10 mM to about 25 mM (e.g., about 10, 11, 12, 13, 14, 15, 16, 17, 18, 19, 20, 21, 22, 23, 24, or 25 mM or any value or range therein). In some embodiments, the chemical buffering system includes, but is not limited to, sodium bicarbonate and/or HEPES. For example, in some embodiments, the culture medium comprises sodium bicarbonate in an amount from about 1 g/L to about 4 g/L of culture medium, e.g., about 1, 1.5, 2, 2.5, 3, 3.5, or 4 g/L or any value or range therein. In some embodiments, the culture medium comprises sodium bicarbonate in an amount from about 1 g/L to about 3.75 g/L, about 1.25 g/L to about 4 g/L, about 2.5 g/L to about 3 g/L, about 1.5 g/L to about 4 g/L, or about 2 g/L to about 3.5 g/L of culture medium. In some embodiments, the culture medium comprises HEPES in an amount from about 10 mM to about 25 mM, e.g., about 10, 11, 12, 13, 14, 15, 16, 17, 18, 19, 20, 21, 22, 23, 24, or 25 mM or any value or range therein. In some embodiments, the culture medium comprises HEPES in an amount from about 1 mM to about 25 mM, about 10 mM to about 20 mM, about 12.5 mM to about 22.5 mM, about 15 mM to about 20.75 mM, or about 10 mM to about 20 mM.

In some embodiments, the culture medium comprises one or more essential amino acids in an amount from about 0.5 mM to about 5 mM (e.g., about 0.5, 1, 1.5, 2, 2.5, 3, 3.5, 4, 4.5, or 5 mM or any value or range therein) or about 0.5, 1, 1.5, 2 mM to about 2.5, 3, 3.5, 4, 4.5, or 5 mM. In some embodiments, one or more essential amino acids is arginine and/or cysteine. For example, in some embodiments, the culture medium comprises arginine in an amount from about 0.5 mM to about 5 mM, e.g., about 0.5, 1, 1.5, 2, 2.5, 3, 3.5, 4, 4.5, or 5 mM or any value or range therein. In some embodiments, the culture medium comprises arginine in an amount from about 0.5 mM to about 4.75 mM, about 2 mM to about 3.5 mM, about 0.5 mM to about 3.5 mM, about 1 mM to about 5 mM, or about 3.5 mM to about 5 mM. For example, in some embodiments, the culture medium comprises cysteine in an amount from about 0.5 mM to about 5 mM, e.g., about 0.5, 1, 1.5, 2, 2.5, 3, 3.5, 4, 4.5, or 5 mM or any value or range therein. In some embodiments, the culture medium comprises cysteine in an amount from about 0.5 mM to about 4.75 mM, about 2 mM to about 3.5 mM, about 0.5 mM to about 3.5 mM, about 1 mM to about 5 mM, or about 3.5 mM to about 5 mM.

In some embodiments, the culture medium comprises one or more vitamins and/or cofactors in an amount from about 0.01 µM to about 50 µM (e.g., about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 3, 4, 5, 6, 7, 8, 9, 10, 12.5, 15, 17.5, 20, 25, 30, 35, 40, 45, 46, 47, 48, 49, 49.025, 49.05, 49.075, or 50 µM or any value or range therein) or about 0.01, 0.02, 0.03, 0.04, 0.05, 0.06, 0.07, 0.08, 0.09, 0.1, 0.2, 0.3, 0.4, 0.5, 0.6, 0.7, 0.8, or 0.9 µM to about 1, 1.1, 1.2, 1.3, 1.4, 1.5, 1.6, 1.7, 1.8, 1.9, 2, 2.1, 2.2, 2.3, 2.4, 2.5, 3, 4, 5, 6 µM or about 0.02, 0.025, 0.05, 0.075, 1, 1.5, 2, 3, 4, 5, 6, 7, 8, 9, 10 µM to about 12.5, 15, 17.5, 20, 25, 30, 35, 40, 45, 46, 47, 48, 49, 49.025, 49.05, 49.075, or 50 µM. In some embodiments, one or more vitamins and/or cofactors includes, but is not limited to, thiamine and/or riboflavin. For example, in some embodiments, the culture medium comprises thiamine in an amount from about 0.025 µM to about 50 µM, e.g., 0.025, 0.05, 0.075, 1, 1.5, 2, 3, 4, 5, 6, 7, 8, 9, 10, 12.5, 15, 17.5, 20, 25, 30, 35, 40, 45, 46, 47, 48, 49, 49.025, 49.05, 49.075, or 50 µM or any value or range therein. In some embodiments, the culture medium comprises thiamine in an amount from about 0.025 µM to about 45.075 µM, about 1 µM to about 40 µM, about 5 µM to about 35.075 µM, about 10 µM to about 50 µM, or about 0.05 µM to about 45.5 µM. In some embodiments, the culture medium comprises riboflavin in an amount from about 0.01 µM to about 3 µM, e.g., 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, or 3 µM or any value or range therein. In some embodiments, the culture medium comprises riboflavin in an amount from about 0.01 µM to about 2.05 µM, about 1 µM to about 2.95 µM, about 0.05 µM to about 3 µM, about 0.08 µM to about 1.55 µM, or about 0.05 µM to about 2.9 µM.

In some embodiments, the culture medium comprises one or more inorganic salts in an amount from about 100 mg/L to about 150 mg/L of culture medium (e.g., about 100, 105, 110, 115, 120, 125, 130, 135, 140, 145, or 150 mg/L or any value or range therein) or about 100 mg/L to about 150 mg/L of culture medium (e.g., about 100, 105, 110, 115, 120, 125, 130, 135, 140, 145, or 150 mg/L or any value or range therein). In some embodiments, exemplary one or more inorganic salts is calcium and/or magnesium. For example, in some embodiments, the culture medium comprises calcium in an amount from about 100 mg/L to about 150 mg/L of culture medium, e.g., about 100, 105, 110, 115, 120, 125, 130, 135, 140, 145, or 150 mg/L or any value or range therein. In some embodiments, the culture medium comprises arginine in an amount from about 100 mg/L to about 125 mg/L, about 105 mg/L to about 150 mg/L, about 120 mg/L to about 130 mg/L, or about 100 mg/L to about 145 mg/L of culture medium. In some embodiments, the culture medium comprises magnesium in an amount from about 0.01 mM to about 1 mM, e.g., about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 0.91, 0.92, 0.93, 0.94, 0.95, 0.96, 0.97, 0.98, 0.99, or 1 mM or any value or range therein. In some embodiments, the culture medium comprises magnesium in an amount from about 0.05 mM to about 1 mM, about 0.01 mM to about 0.78 mM, about 0.5 mM to about 1 mM, about 0.03 mM to about 0.75 mM, or about 0.25 mM to about 0.95 mM.

In some embodiments, the carbon source, chemical buffering system, one or more essential amino acids, one or more vitamins and/or cofactors, and/or one or more inorganic salts is food grade.

In some embodiments, the culture medium is lactogenic culture medium, e.g., the culture medium further comprises prolactin (e.g., mammalian prolactin, e.g., human prolactin). For example, in some embodiments, the culture medium comprises prolactin (or prolactin is added) in an amount from about 20 ng/mL to about 200 ng/L of culture medium, e.g., about 20, 30, 40, 50, 60, 70, 80, 90, 100, 110, 120, 130, 140, 150, 160, 170, 180, 190, or 200 ng/mL or any value or range therein. In some embodiments, the culture medium comprises prolactin (or prolactin is added) in an amount from about 20 ng/mL to about 195 ng/mL, about 50 ng/mL to about 150 ng/mL, about 25 ng/mL to about 175 ng/mL, about 45 ng/mL to about 200 ng/mL, or about 75 ng/mL to about 190 ng/mL of culture medium. In some embodiments, the methods further comprise adding prolactin to the culture medium, thereby providing a lactogenic culture medium. In some embodiments, the prolactin is produced by a microbial cell and/or a human cell expressing a recombinant prolactin (e.g., a prolactin comprising a substitution of a serine residue at position 179 of the prolactin gene with aspartate (S179D), e.g., S179D-prolactin). In some embodiments, adding prolactin to the culture medium comprises conditioning culture medium by culturing cells that express and secrete prolactin, and applying the conditioned culture medium comprising prolactin to the basal surface of the monolayer of mammary cells (e.g., mammary epithelial cells, mammary myoepithelial cells and mammary progenitor cells).

In some embodiments, the culture medium further comprises other factors to improve efficiency, including, but not limited to, insulin, an epidermal growth factor, and/or a hydrocortisone. In some embodiments, the methods of the present invention further comprise adding other factors (e.g., insulin, an epidermal growth factor, and/or a hydrocortisone) to the culture medium, e.g., to improve efficiency.

Methods of Manufacturing Cultured Milk Products

Disclosed herein are methods of manufacturing a cultured milk product representing the biosynthetic output of cultured mammary epithelial cells (MECs) and plasma cells.

In some embodiments, the method comprises culturing a cell construct comprising plasma cells and mammary cells disclosed herein in a bioreactor comprising a basal compartment and an apical compartment, wherein the basal compartment comprises a culture media, and the plasma cells and mammary cells secret the cultured milk product comprising immunoglobulins into the apical compartment.

In some embodiments, the method comprises (a) isolating mammary epithelial cells, myoepithelial cells and/or mammary progenitor cells from mammary explants from mammary tissue (e.g., breast, udder, teat tissue), biopsy sample, or raw breastmilk, to produce isolated mammary epithelial cells, myoepithelial cells and/or mammary progenitor cells; (b) isolating plasma cells from mammary tissue, biopsy sample, or raw breastmilk, to produce isolated primary plasma cells; (c) culturing the isolated mammary epithelial cells, myoepithelial cells and/or mammary progenitor cells; (d) culturing the isolated primary plasma cells; (e) depositing the cultured, isolated mammary epithelial cells, myoepithelial cells and/or mammary progenitor cells and isolated primary plasma cells on a scaffold having an upper surface and lower surface to produce a mixed population of primary plasma cells and mammary epithelial cells, mammary myoepithelial cells and mammary progenitor cells wherein the plasma cells are overlayed by the mammary epithelial cells, mammary myoepithelial cells and mammary progenitor cells; (f) cultivating the mixed population of (e) on the scaffold, to produce a monolayer of polarized mammary cells located adjacent to and above the plasma cells, wherein the plasma cells are located adjacent to and above the upper surface of the scaffold, wherein the upper surface is located adjacent to and above the lower surface of the scaffold, and wherein the polarized mammary cells comprise an apical surface and a basal surface, thereby producing a cell construct for producing the cultured milk product comprising immunoglobulins.

In some embodiments, the method comprises: a) isolating mammary epithelial cells, myoepithelial cells, and/or mammary progenitor cells from mammary explants from mammary tissue (e.g., breast, udder, teat tissue), biopsy sample, or raw breastmilk, to produce isolated mammary epithelial cells, myoepithelial cells, and/or mammary progenitor cells; (b) isolating plasma cells from mammary tissue, biopsy sample, or raw breastmilk, to produce isolated primary plasma cells; (c) culturing the isolated mammary epithelial cells, myoepithelial cells, and/or mammary progenitor cells to produce a mixed population of primary mammary epithelial cells, mammary myoepithelial cells and mammary progenitor cells; (d) culturing the isolated primary plasma cells; (e) sorting the mixed population of mammary epithelial cells, myoepithelial cells, and/or mammary progenitor cells (e.g., selecting the primary mammary epithelial cells) to produce a population of primary mammary epithelial cells; and (f) depositing the sorted population of primary mammary epithelial cells, myoepithelial cells and/or mammary progenitor cells and isolated primary plasma cells on a scaffold having an upper surface and lower surface (g) cultivating the sorted population of mammary epithelial and plasma cells on the scaffold, to produce a monolayer of polarized primary mammary epithelial cells located adjacent to and above the plasma cells, wherein the plasma cells are located adjacent to and above the upper surface of the scaffold, wherein the upper surface is located adjacent to and above the lower surface of the scaffold, and wherein the polarized mammary cells comprise an apical surface and a basal surface, and wherein the polarized monolayer comprises an apical surface and a basal surface, thereby producing a cell construct for producing the cultured milk product comprising immunoglobulins.

In some embodiments, the method comprises (a) culturing immortalized mammary epithelial cells to produce increased numbers of immortalized mammary epithelial cells; and (b) culturing plasma cells to produce increased numbers of plasma cells; (c) cultivating the immortalized mammary epithelial cells and plasma cells of (a) and (b) on a scaffold, the scaffold having an upper surface and lower surface, to produce a monolayer of polarized immortalized mammary epithelial cells above the plasma cells on the upper surface of the scaffold, wherein the polarized monolayer comprises an apical surface and a basal surface, thereby producing a cell construct for producing the cultured milk product comprising immunoglobulins.

In certain embodiments, plasma cells are added to the culture of immortalized mammary epithelial cells. In certain embodiments, the plasma cells are cultivated with the immortalized mammary epithelial cells on the scaffold, thereby producing a cultured milk product with secretory products of the immune cells and mammary cells (e.g., sIgA). In certain embodiments, the isolated mammary cells are immortalized prior to co-culture of the cells with the plasma cells.

Plasma cells can be derived from a primary mammary tissue sample or, e.g., from a plasma cell line. In certain embodiments, the plasma cells are stimulated to produce immunoglobins during co-culture. In certain embodiments, the plasma cells produce IgA. In certain embodiments the plasma cells produce secretory IgA. In certain embodiments, the one or more classes of immunoglobulins includes secretory IgA (sIgA). In certain embodiments, the immunoglobulins bind to an antigen of a microorganism (i.e., bacterium or virus). In certain embodiments, the immunoglobulins bind to viral or bacterial antigens capable of causing an infectious disease in humans. In certain embodiments, the immunoglobulins bind to viral or bacterial antigens that cause infections of respiratory or gastrointestinal epithelium. In certain embodiments, the immunoglobulins bind antigens from microorganisms that cause enterocolitis or sepsis in infants. In certain embodiments, plasma cells are co-cultured with MECs in a bioreactor according to methods described herein. In certain embodiments, the bioreactor is a hollow fiber bioreactor described herein.

In certain embodiments, mammary cells are modified and/or stimulated with prolactin according to the methods described herein to stimulate and optimize milk production. In certain embodiments, the mammary cells are modified to express a constitutively active prolactin receptor.

In certain embodiments, mammary epithelial cell populations are identified and isolated from primary mammary tissue samples. In some embodiments, the mammary cells are isolated and sorted via fluorescence-activated cell sorting, magnetic-activated cell sorting, and/or microfluidic cell sorting. In certain embodiments, myoepithelial mammary cells and luminal epithelial mammary cells are isolated by FACS analysis. In certain embodiments, progenitor myoepithelial mammary cells and/or progenitor luminal epithelial mammary cells are isolated by FACS analysis. Any suitable method known in the art for sorting mammary epithelial cells (e.g., luminal epithelial cells), myoepithelial cells, progenitor cells, and immune cells can be used. For example, mammary cells can be sorted using CD24, EPCAM and/or CD49f, cell surface markers.

In some embodiments, the plasma cells are isolated and sorted via fluorescence-activated cell sorting, magnetic-activated cell sorting, and/or microfluidic cell sorting. In certain embodiments, the plasma cells are sorted by FACS analysis using markers known in the art for identifying the plasma cells. In certain embodiment, plasma cells, plasma blasts or pre-plasmablasts are sorted and isolated by FACS analysis using markers known in the art (e.g., CD20, CD38, CD138, and/or CD19).

In some embodiments, the cell construct comprises a scaffold comprising an upper surface and a lower surface and a continuous monolayer of polarized mammary epithelial cells, a continuous monolayer of a polarized, mixed population of mammary epithelial cells, mammary myoepithelial cells and mammary progenitor cells, and/or a continuous monolayer of polarized immortalized mammary epithelial cells, wherein the continuous monolayer is located on the upper surface of scaffold.

In some embodiments, the lower surface of the scaffold is adjacent to the basal compartment. In some embodiments, the apical surface of the continuous monolayer is adjacent to the apical compartment. In some embodiments, the continuous monolayer secretes milk and sIgA or IgA through its apical surface into the apical compartment, thereby producing milk comprising IgA and/or sIgA in culture.

In some embodiments, the monolayer of mammary cells forms a barrier that divides the apical compartment and the basal compartment, wherein the basal surface of the mammary cells are attached to the scaffold and the apical surface is oriented toward the apical compartment.

In some embodiments, the basal compartment is adjacent to the lower surface of the scaffold. In some embodiments, the basal compartment comprises a culture medium in fluidic contact with the basal surface of the monolayer of mammary epithelial cells (e.g., the polarized monolayer of mammary epithelial cells, the polarized the monolayer of the mixed population of mammary cells, or the polarized monolayer of immortalized mammary epithelial cells).

In some embodiments, the culture medium comprises a carbon source, a chemical buffering system, one or more essential amino acids, one or more vitamins and/or cofactors, and one or more inorganic salts.

In some embodiments, the bioreactor comprises an apical compartment that is adjacent to the apical surface of the monolayer. In some embodiments, the apical compartment is adjacent to the upper surface of the scaffold.

In some embodiments, the total cell density of mammary cells in the bioreactor is at least $10^{11}$ mammary cells. In some embodiments, the total cell density of mammary cells in the bioreactor is at least $10^{12}$ mammary cells. In some embodiments, the total cell density of mammary cells in the bioreactor is at least $10^{13}$ mammary cells.

In some embodiments, the total cell density of mammary cells in the bioreactor is about 20 to 55 cells per 100 $\mu m^2$. In some embodiments, the total cell density of mammary cells in the bioreactor is about 20 cells per 100 $\mu m^2$. In some embodiments the total cell density of mammary cells in the bioreactor is 25 cells per 100 $\mu m^2$. In some embodiments, the total cell density of mammary cells in the bioreactor is about 30 cells per 100 $\mu m^2$. In some embodiments, the total cell density of mammary cells in the bioreactor is about 35 cells per 100 $\mu m^2$. In some embodiments, the total cell density of mammary cells in the bioreactor is about 40 cells per 100 $\mu m^2$. In some embodiments, the total cell density of mammary cells in the bioreactor is about 45 cells per 100 $\mu m^2$. In some embodiments, the total cell density of mammary cells in the bioreactor is about 50 cells per 100 $\mu m^2$. In some embodiments, the total cell density of mammary cells in the bioreactor is about 55 cells per 100 $\mu m^2$.

In some embodiments, the total cell density of plasma cells in the bioreactor is about 200 to 500 plasma cells per $mm^2$. In some embodiments, the total cell density of plasma cells in the bioreactor is about 200 plasma cells per $mm^2$. In some embodiments, the total cell density of plasma cells in the bioreactor is about 300 plasma cells per $mm^2$. In some embodiments, the total cell density of plasma cells in the bioreactor is about 400 plasma cells per $mm^2$. In some embodiments, the total cell density of plasma cells in the bioreactor is about 500 plasma cells per $mm^2$.

In some embodiments, the total surface area of mammary cells within the bioreactor is at least about 1.5 $m^2$. In some embodiments, the total surface area of mammary cells within the bioreactor is at least about 2 $m^2$. In some embodiments, the total surface area of mammary cells within the bioreactor is at least about 2.5 $m^2$. In some embodiments, the total surface area of mammary cells within the bioreactor is at least about 3 $m^2$. In some embodiments, the total surface area of mammary cells within the bioreactor is at least about 4 $m^2$. In some embodiments, the total surface area of mammary cells within the bioreactor is at least about 5 $m^2$. In some embodiments, the total surface area of mammary cells within the bioreactor is at least about 10 $m^2$. In some embodiments, the total surface area of mammary cells within the bioreactor is at least about 15 m². In some embodiments, the total surface area of mammary cells within the bioreactor is at least about 20 m². In some embodiments, the total surface area of mammary cells within the bioreactor is at least about 25 m². In some embodiments, the total surface area of mammary cells within the bioreactor is at least about 50 m². In some embodiments, the total surface area of mammary cells within the bioreactor is at least about 100 m². In some embodiments, the total surface area of mammary cells within the bioreactor is at least about 250 m². In some embodiments, the total surface area of mammary cells within the bioreactor is at least about 500 m².

In some embodiments, the bioreactor maintains a temperature of about 27° C. to about 39° C. (e.g., a temperature of about 27° C., 28° C., 29° C., 30° C., 31° C., 32° C., 33° C., 34° C., 35° C., 35° C., 35.5° C., 36° C., 36.5° C., 37° C., 37.5° C., 38° C., 38.5° C. or about 39° C., or any value or range therein, e.g., about 27° C. to about 38° C., about 36° C. to about 39° C., about 36.5° C. to about 39° C., about 36.5° C. to about 37.5° C., or about 36.5° C. to about 38° C.). In some embodiments, the bioreactor maintains a temperature of about 37° C.

In some embodiments, the bioreactor has an atmospheric concentration of $CO_2$ of about 4% to about 6%, e.g., an atmospheric concentration of $CO_2$ of about 4%, 4.25%, 4.5%, 4.75%, 5%, 5.25%, 5.5%, 5.75%, or 6% or any value or range therein, e.g., about 4% to about 5.5%, about 4.5% to about 6%, about 4.5% to about 5.5%, or about 5% to about 6%). In some embodiments, the bioreactor has an atmospheric concentration of $CO_2$ of about 5%.

In some embodiments, the bioreactor has an atmospheric concentration of $CO_2$ of about 4% to about 6%, e.g., an atmospheric concentration of $CO_2$ of about 4%, 4.25%, 4.5%, 4.75%, 5%, 5.25%, 5.5%, 5.75%, or 6% or any value or range therein, e.g., about 4% to about 5.5%, about 4.5% to about 6%, about 4.5% to about 5.5%, or about 5% to about 6%). In some embodiments, the bioreactor has an atmospheric concentration of $CO_2$ of about 5%.

In some embodiments, the method comprises monitoring the concentration of dissolved $O_2$ and $CO_2$. In some embodiments, the concentration of dissolved $O_2$ is maintained between about 10% to about 25% or any value or range therein (e.g., about 10, 11, 12, 13, 14, 15, 16, 17, 18, 19, 20, 21, 22, 23, 24, or 25%). For example, in some embodiments, the concentration of dissolved $O_2$ is maintained between about 12% to about 25%, about 15% to about 22%, about 10% to about 20%, about 15% to about 20%, or about 22%. In some embodiments, the concentration of $CO_2$ is maintained between about 4% to about 6%, e.g., a concentration of $CO_2$ of about 4%, 4.25%, 4.5%, 4.75%, 5%, 5.25%, 5.5%, 5.75%, or 6% or any value or range therein, e.g., about 4% to about 5.5%, about 4.5% to about 6%, about 4.5% to about 5.5%, or about 5% to about 6%). In some embodiments, the concentration of $CO_2$ is maintained at about 5%.

In some embodiments, the culture medium is exchanged about every day to about every 10 days (e.g., every 1 day, every 2 days, every 3 days, every 4 days, every 5 days, every 6 days, every 7 days, every 8 days, every 9 days, every 10 days, or any value or range therein, e.g., about every day to every 3 days, about 3 days to every 10 days, about every 2 days to every 5 days). In some embodiments, the culture medium is exchanged about every day to about every few hours to about every 10 days, e.g., about every 1, 2, 3, 4, 5, 6, 7, 8, 9, 10, 11, 12, 13, 14, 15, 16, 17, 18, 19, 20, 21, 22, 23, or 24 hours to about every 1, 2, 3, 4, 5, 6, 7, 8, 9, or 10 days or any value or range therein. For example, in some embodiments, the culture medium is exchanged about every 12 hours to about every 10 days, about every 10 hours to about every 5 days, or about every 5 hours to about every 3 days.

In some embodiments, the method comprises monitoring the glucose concentration and/or rate of glucose consumption in the culture medium and/or in the lactogenic culture medium. In some embodiments, the prolactin is added when the rate of glucose consumption in the culture medium is steady state.

In some embodiments, the method further comprises applying transepithelial electrical resistance (TEER) to measure the maintenance of the monolayer of epithelial cells. TEER measures a voltage difference between the fluids (e.g., media) in two compartments (e.g., between the apical and basal compartments), wherein if the barrier between the compartments loses integrity, the fluids in the two compartments may mix. When there is fluid mixing, the voltage difference will be reduced or eliminated; a voltage difference indicates that the barrier is intact. In some embodiments, upon detection of a loss of voltage by TEER, a scaffold (e.g., a Transwell® filter, a microstructured bioreactor, a decellularized tissue, a hollow fiber bioreactor, etc.) is reinoculated with additional cells and allowed time to reestablish a barrier (e.g., a monolayer) before resuming production of the cultured milk product (e.g., milk production).

In some embodiments, the method further comprises collecting the cultured milk product from the apical compartment to produce collected cultured milk product. In some embodiments, the collecting is via a port, via gravity, and/or via a vacuum. In some embodiments, a vacuum is attached to a port.

In some embodiments, the method further comprises freezing the collected cultured milk product to produce frozen cultured milk product and/or lyophilizing the collected cultured milk product to produce lyophilized cultured milk product.

In some embodiments, the method further comprises packaging the collected cultured milk product, the frozen cultured milk product and/or the lyophilized cultured milk product into a container.

In some embodiments, the method further comprises extracting one or more components from the collected cultured milk product. Non-limiting examples of components from the collected cultured milk product include milk protein, lipid, carbohydrate, vitamin, and/or mineral contents. In some embodiments, the components from the collected cultured milk product are lyophilized and/or concentrated to produce a lyophilized or a concentrated cultured milk product component product. In some embodiments, the components from the collected cultured milk product are concentrated by, e.g., membrane filtration and/or reverse osmosis. In some embodiments, the lyophilized or concentrated cultured milk product component product is packaged in a container, optionally wherein the container is sterile and/or a food grade container. In some embodiments, the container is vacuum-sealed. In some embodiments, the container is a canister, a jar, a bottle, a bag, a box, or a pouch. In some embodiments, the cultured milk product is a standardized, sterile cultured milk product. In some embodiments, the cultured milk product is for nutritional use.

In some embodiments, the cultured milk product is produced by any method disclosed herein.

Breast milk contains low but measurable concentrations of environmental contaminants, health-harming chemicals from industry and manufacturing products that are widely spread in the environment. Environmental contaminants are partly secreted in breast milk. The contaminant levels in breast milk reflect those in the mother's body and are therefore ideal for monitoring exposure levels. Toxic environmental contaminants can be transferred from mother to infant via breastfeeding. Persistent organic pollutants (POPs) are a family of lipophilic stable chemicals that bioaccumulate in adipose tissue and create a lasting toxic body burden. Breastfeeding provides a significant source of exposure to POPs early in human life, the effects of which are unknown.

In some embodiments, the cultured milk product does not comprise or is substantially free of one or more environmental contaminants. In some embodiments, the cultured milk product does not comprise or is substantially free of persistent organic pollutants (POPs). In some embodiments, the cultured milk product does not comprise or is substantially free of polychlorinated dibenzo-p-dioxins (PCDDs), polychlorinated dibenzofurans (PCDFs), polychlorinated biphenyls (PCBs) and pesticides such as DDT.

Heavy metals such as mercury, lead, arsenic, cadmium, nickel, chromium, cobalt, zinc, and other potentially toxic metals that are dispersed throughout the environment also have bioaccumulative features known to accumulate in human milk and thus are of concern to the nursing infant. Metal in breast milk originates from exogenous sources, i.e., uptake via contaminated air, food, and drinking water, and endogenous release along with essential trace elements. For example, lead and mercury are equally dispersed in the human food chain, and their impact on fetal development is heavily determined by the mother's diet and nutritional status. The exposures to toxic metals have significant public health implication, even at small concentrations and acute exposures, these metals remain toxic to humans. A nursing infant may be exposed to toxic metals in a period of highest susceptibility. Nursing infants may be exposed to heavy metals through breast milk in excess of what they should, and exposure may have health implication for the infants. For infants in particular, these exposures may have adverse effect on the developing central nervous system, leaving a life-long defect on their cognitive abilities.

In some embodiments, the cultured milk product does not comprise or is substantially free of one or more heavy metals, such as arsenic, lead, cadmium, nickel, mercury, chromium, cobalt, and zinc. In some embodiments, the cultured milk product does not comprise or is substantially free of arsenic. In some embodiments, the cultured milk product does not comprise or is substantially free of lead. In some embodiments, the cultured milk product does not comprise or is substantially free of cadmium. In some embodiments, the cultured milk product does not comprise or is substantially free of nickel. In some embodiments, the cultured milk product does not comprise or is substantially free of mercury. In some embodiments, the cultured milk product does not comprise or is substantially free of chromium. In some embodiments, the cultured milk product does not comprise or is substantially free of cobalt. In some embodiments, the cultured milk product does not comprise or is substantially free of zinc. In some embodiments, the cultured milk product does not comprise or is substantially free of arsenic, lead, cadmium, nickel, mercury, chromium, cobalt, and zinc.

Foreign allergenic proteins can be difficult to distinguish from endogenous human milk proteins. Food proteins with allergenic potential that have been detected in human milk include hen's egg and peanut proteins. There are eight major food allergens, known as the big 8, that are responsible for most of the serious food allergy reactions in the U.S. The big 8 list is comprised of milk, egg, fish, crustacean shellfish, tree nuts, peanuts, wheat, and soybean allergens. Proteins known to cause egg allergy include ovomucoid, ovalbumin, and conalbumin. Peanuts proteins include arachin 6, arachin 3, conarachin, main allergen Arah1, and arachin Arah2. As an example of maternal dietary protein transportation to milk, it has been shown that the consumption of one egg per day leads to higher concentrations of the chicken egg allergen ovalbumin (OVA) in human milk compared to egg-avoiding mothers.

In some embodiments, the cultured milk product does not comprise or is substantially free of one or more food allergens. In some embodiments, the cultured milk product does not comprise or is substantially free of egg, fish, crustacean shellfish, tree nuts, peanuts, wheat, and soybean allergens. In some embodiments, the cultured milk product does not comprise or is substantially free of egg allergens. In some embodiments, the cultured milk product does not comprise or is substantially free of fish allergens. In some embodiments, the cultured milk product does not comprise or is substantially free of crustacean allergens. In some embodiments, the cultured milk product does not comprise or is substantially free of tree nut allergens. In some embodiments, the cultured milk product does not comprise or is substantially free of peanut allergens. In some embodiments, the cultured milk product does not comprise or is substantially free of wheat allergens. In some embodiments, the cultured milk product does not comprise or is substantially free of soybean allergens.

In some embodiments, the cultured milk product does not comprise or is substantially free of arachin 6, arachin 3, conarachin, Arah1, and Arah2.

In some embodiments, the cultured milk product does not comprise or is substantially free of ovalbumin (OVA).

Methods of Use

Disclosed herein, in certain embodiments, are methods of treating and/or preventing infection comprising administration of a cultured milk product comprising IgA or sIgA described herein, or and immunotherapeutic composition comprising isolated IgA or sIgA described herein.

In certain embodiments, the immunotherapeutic compositions and cultured milk products comprising IgA and/or sIgA are administered to patients in an effective amount for the treatment or prevention of a microbial infection. In certain embodiments, the microbial infection is a bacterial infection. Non-limiting examples of bacterial infections that can be treated and/or prevented include infections caused by: *Streptococcus pneumoniae, Haemophilus influenzae, Moraxella catarrhalis, Staphylococcus aureus, Streptococcus pyogenes, Salmonella, Shigella, Campylobacter, Staphylococcus aureus* and *Helicobacter pylori*. In certain embodiments, the microbial infection is a viral infection. Non-limiting examples of viral infection that can be treated and/or prevented include infections caused by: influenza virus, parainfluenza virus, respiratory syncytial virus, rhinovirus, and human metapneumovirus.

In certain embodiments, the cultured milk product immune comprising IgA or sIgA, or therapeutic composition comprising IgA or sIgA are administered orally to a subject to treat or prevent a gastrointestinal infection. In certain embodiments, the gastrointestinal infection is bacterial or viral gastroenteritis. In certain embodiments, the subject has an ulcer caused by an infection of *Helicobacter pylori*. In certain embodiments, the subject has an infection caused by norovirus, adenovirus, or rotavirus. In certain embodiments, the immunotherapeutic compositions and/or cultured milk products are administered to an infant for the treatment or prevention of gastrointestinal infection.

In certain embodiments, the immunotherapeutic compositions disclosed herein are administered to a subject as a nasal inhalant to treat or prevent a respiratory infection. In certain embodiments, the subject has pneumonia, bronchitis, and/or lung tissue damage.

In certain embodiments, the subject is immune compromised. The subject can be immune compromised due to a primary immune deficiency disease or disorder (e.g., severe combined immunodeficiency (SCID) or a secondary immune deficiency, such as, but not limited to, chemotherapy treatment, diabetes, aging, malnutrition, and acquired immunodeficiency syndrome. In certain embodiments, the immunotherapeutic compositions and/or cultured milk products are administered to an infant for the treatment or prevention of an infection.

In certain embodiments, the immunotherapeutic compositions and/or cultured milk products are administered in combination with another anti-microbial agent (i.e., antibiotic or anti-viral agent). In certain embodiments, the cultured milk product described herein are administered with an additional nutritional product for treatment and/or prevention of a gastrointestinal infection.

Having described the present disclosure, the same will be explained in greater detail in the following examples, which are included herein for illustration purposes only, and which are not intended to be limiting to the disclosure.

EXAMPLES

The Examples that follow are illustrative of specific embodiments of the disclosure, and various uses thereof. They are set forth for explanatory purposes only and should not be construed as limiting the scope of the disclosure in any way.

Example 1: Production of Milk Components from Human Mammary Epithelium

In this example, human mammary epithelium is recapitulated and milk is produced in vitro. The system and process described is exemplary and can be scaled to produce multiliter volumes of milk components. Mammary epithelial cells are expected to form a polarized monolayer on bioreactor fibers that have been precoated with one or more of laminin and collagen or other extracellular matrix proteins, as well as on uncoated fibers. When confluent, the monolayer forms a barrier that divides the intra- and extracapillary space (ECS), with the basal surface attached to the fibers and the apical surface oriented toward the ECS. Milk component production is stimulated by addition of prolactin to the media. The secreted milk components are collected from the ECS and submitted for downstream analyses of the protein, lipid, and carbohydrate content in comparison to human breast milk produced in vivo.

Materials for use in this Example are shown in Table 3.

| Materials | | |
|---|---|---|
| Item | Supplier | Catalog Number |
| Primary mammary epithelial cells | ATCC | PCS-600-010 |
| Mammary epithelial cell basal medium | ATCC | PCS-600-30 |
| Mammary epithelial cell growth kit | ATCC | PCS-600-040 |

-continued

| Materials | | |
|---|---|---|
| Item | Supplier | Catalog Number |
| Dulbecco's phosphate buffered saline (D-PBS) | ATCC | ATCC 30-2200 |
| Trypsin-EDTA | ATCC | PCS-999-003 |
| Trypsin Neutralizing Solution | ATCC | PCS-999-004 |
| EHS (Laminin-1/111) | Sigma | L2020-1 MG |
| Collagen-IV | Sigma | C5533-5 MG |
| Prolactin | Shenandoah Biotechnology | 100-45-500 ug |

Procedures

Expansion of Primary Human Mammary Epithelia Cells (HMECs)

Human mammary epithelial cells (1 ampoule; $5 \times 10^5$ cells) are expanded into one collagen-IV-coated T300 flask (or two T175 flasks) in mammary epithelial cell medium prepared with supplements provided in the kit listed in Table 3. Once an appropriate cell number is obtained, cells are rinsed with D-PBS and collected from the plates using trypsin-EDTA. Once cells are detached, trypsin activity is halted using Trypsin Neutralizing Solution. Cells are resuspended in medium and seeded into a hollow fiber bioreactor (Fibercell Systems), prepared as described below.

Preparation of Hollow Fiber Bioreactor (C2025D, 20 kD MWCO)

Prior to seeding, a bioreactor cartridge (Fibercell Systems) is prepared by preculturing with PBS for a minimum of 24 hours. The bioreactor cartridge is optionally pre-coated by adding about 50-100 pg of one or more of collagen I, collagen IV, laminin-1 11 (e.g., laminin-111 isolated from Engelbreth-Holm Swarm tumor), alpha-4, alpha-5, fibronectin, and/or entactin in 3.2 mL of PBS and allowing ultrafiltration across the fiber at room temperature overnight. The uncoated or precoated cartridge is exchanged with medium and incubated overnight at room temperature. The medium is then exchanged with the cells collected from the T300 (or T175) flask(s). The reservoir volume is no more than 125 mL. The cartridge is rotated 180 degrees after seeding the cells.

Cell Growth in the Bioreactor and Prolactin Stimulation

After seeding the bioreactor, cells are grown in mammary epithelial cell growth medium supplemented with 10-25 mL DMEM/10% CDM-HD (Dulbecco's Modified Eagle Medium; Chemically Defined Medium for High Density Cell Culture) per 100 mL medium. The proportion of DMEM/CDM-HD can be adjusted based on the rate of glucose consumption.

Before stimulation of milk secretion, the medium in the ECS is flushed and replaced with PBS. To stimulate milk component secretion, medium supplemented with 100 ng/mL prolactin is added. The lactogenic medium can also be supplemented with an elevated concentration of glucose and the essential dietary precursors for milk fatty acids, linoleic acid and a-linolenic acid. The bioreactor is maintained for 10 days with sampling as described below.

Harvesting and Sample Preparation

Samples, comprised of supernatant from the ECS and an equivalent volume of media from the reservoir, are collected once daily for 10 days after addition of prolactin to the media. The samples are spun in a centrifuge to collect any debris and resuspended in an equivalent volume of PBS. The supernatants from the ECS and media samples are divided into 0.5 mL aliquots in microfuge tubes and frozen at −80°

C. The pellet debris is resuspended in a volume of PBS equivalent to the original sample and frozen at −80° C. Samples are processed to determine relative concentrations of milk components produced.

Scaling for Multiliter Production

To scale for multiliter production, the preceding procedure with relative adjustments in reagent volumes for a larger bioreactor (e.g., Fibercell Systems cat. no. C2018) is performed.

Example 2

A cell culture system designed for the collection of milk should support compartmentalized secretion of the product such that the milk is not exposed to the media that provides nutrients to the cells. In the body, milk-producing epithelial cells line the interior surface of the mammary gland as a continuous monolayer. The monolayer is oriented such that the basal surface is attached to an underlying basement membrane, while milk is secreted from the apical surface and stored in the luminal compartment of the gland, or alveolus, until it is removed during milking or feeding. Tight junctions along the lateral surfaces of the cells ensure a barrier between the underlying tissues and the milk located in the alveolar compartment. Therefore, in vivo, the tissue of the mammary gland is arranged such that milk secretion is compartmentalized, with the mammary epithelial cells themselves establishing the interface and maintaining the directional absorption of nutrients and secretion of milk.

The present disclosure describes a cell culture apparatus that recapitulates the compartmentalizing capability of the mammary gland that is used to collect milk from mammary epithelial cells grown outside of the body. Such an apparatus can include a scaffold to support the proliferation of mammary cells at the interface between two compartments, such that the epithelial monolayer provides a physical boundary between the nutrient medium and the secreted milk. In addition to providing a surface for growth, the scaffold provides spatial cues that guide the polarization of the cells and ensures the directionality of absorption and secretion. This invention describes the preparation, cultivation, and stimulation of mammary epithelial cells in a compartmentalizing cell culture apparatus for the production and collection of milk for nutritional use (see e.g., FIG. 1).

Preparation of mammary epithelial cells. Mammary epithelial cells are obtained from surgical explants of dissected mammary tissue (e.g., breast, udder, teat), biopsy sample, or raw breastmilk. Generally, after surgical dissection of the mammary tissue, any fatty or stromal tissue is manually removed under aseptic conditions, and the remaining tissue of the mammary gland is enzymatically digested with collagenase and/or hyaluronidase prepared in a chemically defined nutrient media, which should be composed of ingredients that are "generally recognized as safe" (GRAS). The sample is maintained at 37° C. with gentle agitation. After digestion, a suspension of single cells or organoids is collected, either by centrifugation or by pouring the sample through a sterile nylon cell strainer. The cell suspension is then transferred to a tissue culture plate coated with appropriate extracellular matrix components (e.g., collagen, laminin, fibronectin).

Alternatively, explant specimens can be processed into small pieces, for example by mincing with a sterile scalpel. The tissue pieces are plated onto a suitable surface such as a gelatin sponge or a plastic tissue culture plate coated with appropriate extracellular matrix.

The plated cells are maintained at 37° C. in a humidified incubator with an atmosphere of 5% $CO_2$. During incubation, the media is exchanged about every 1 to 3 days and the cells are sub-cultured until a sufficient viable cell number is achieved for subsequent processing, which includes preparation for storage in liquid nitrogen; development of immortalized cell lines through the stable transfection of genes such as SV40, TERT, or other genes associated with senescence; isolation of mammary epithelial, myoepithelial, and stem/progenitor cell types by, for example, fluorescence-activated cell sorting; and/or introduction into a compartmentalizing tissue culture apparatus for the production and collection of milk for human consumption.

Figure 2:
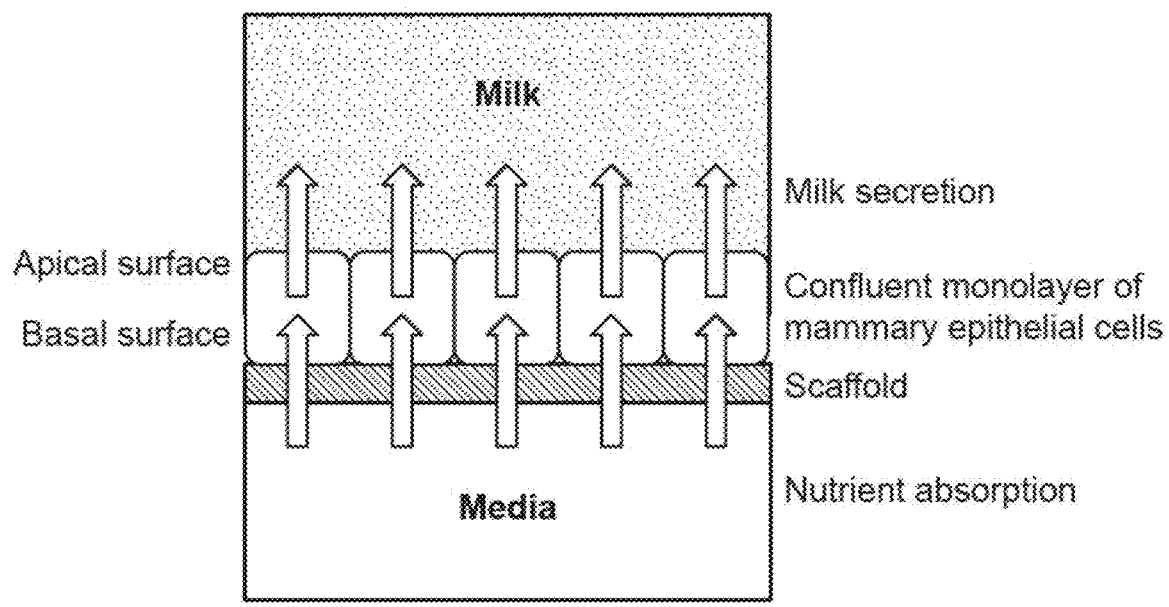
FIG. 2 shows an example of polarized absorption of nutrients and secretion of milk across a confluent monolayer of mammary epithelial cells anchored to a scaffold at the basal surface.

Cultivation of mammary epithelial cells for the production of milk. Milk for nutritional use is produced by mammary epithelial cells isolated as described above and cultured in a format that supports compartmentalized secretion such that separation between the nutrient medium and the product is maintained. The system relies on the ability of mammary epithelial cells to establish a continuous monolayer with appropriate apical-basal polarity when seeded onto an appropriate scaffold positioned at the interface between the apical compartment, into which milk is secreted, and the basal compartment, through which nutrient media is provided (see, e.g., FIG. 2). Transwell® filters placed in tissue culture plates, as well as bioreactors based on hollow fiber or microstructured scaffolds, for example, are used to support these characteristics.

Figure 3:
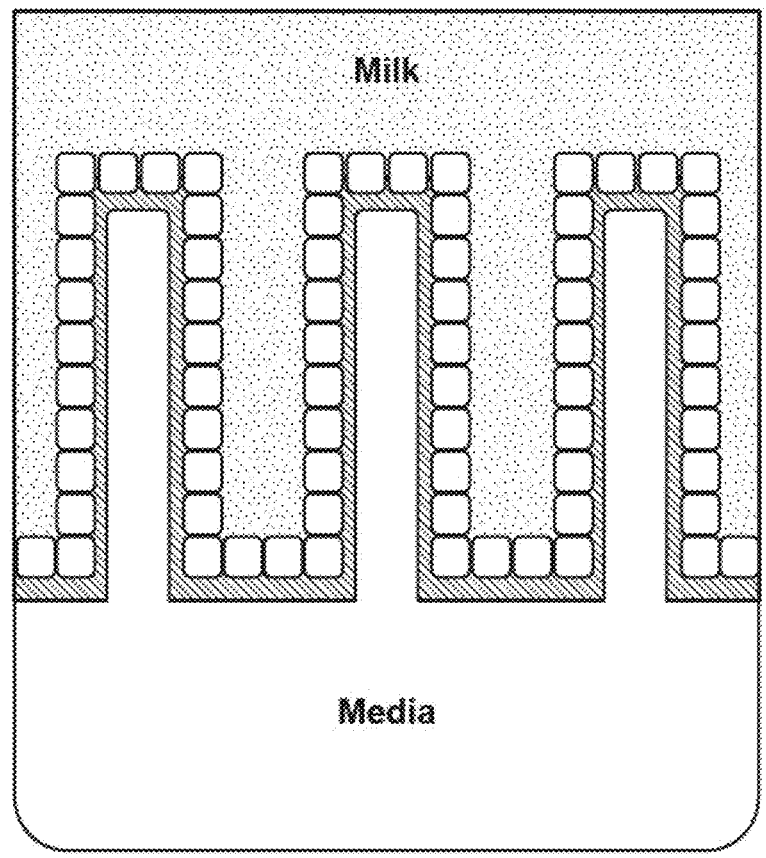
FIG. 3 shows an example micropatterned scaffold that provides increased surface area for the compartmentalized absorption of nutrients and secretion of milk by a confluent monolayer of mammary epithelial cells.
Figure 4:
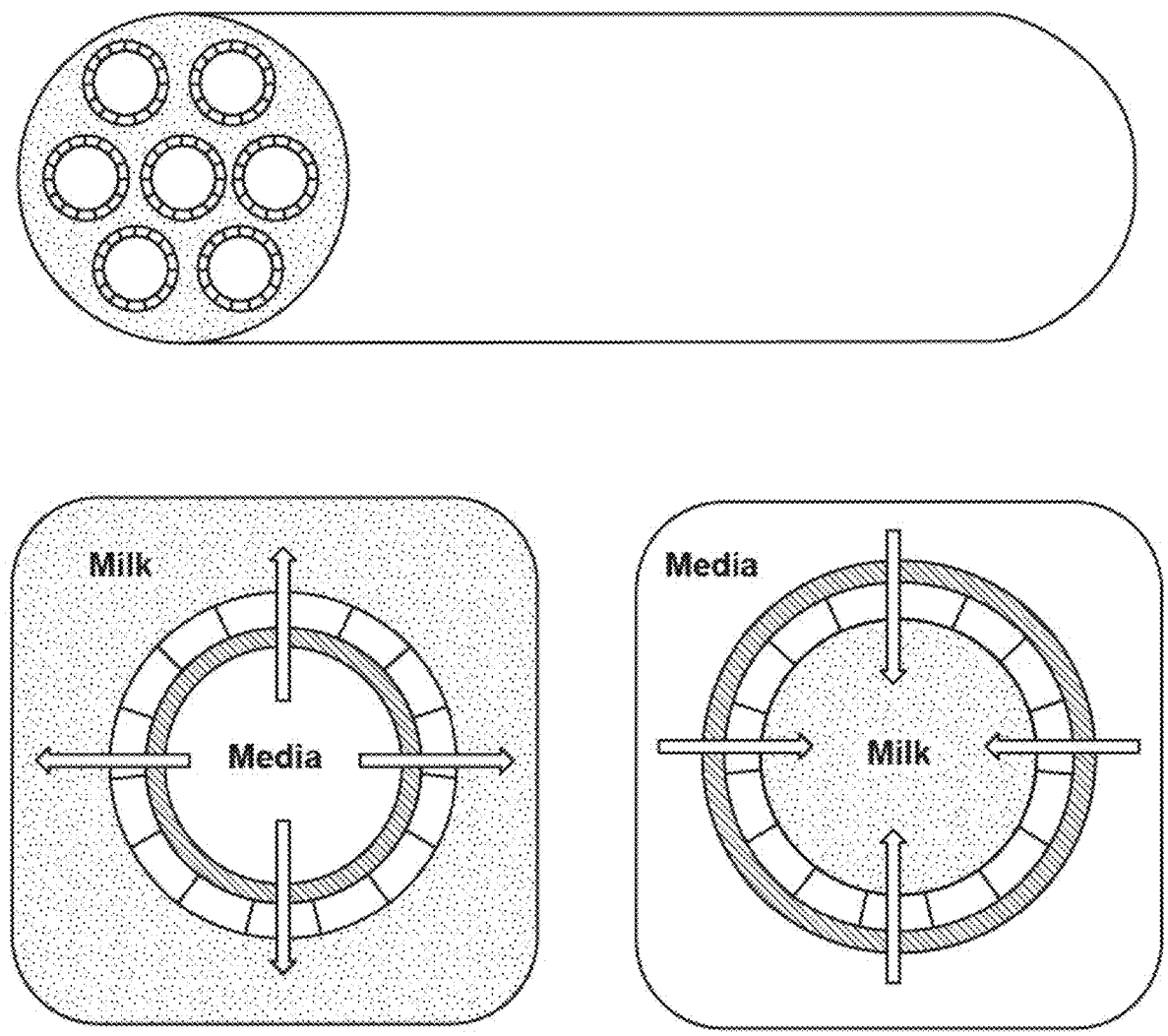
FIG. 4 shows three examples of a hollow fiber bioreactor depicted as a bundle of capillary tubes (top), which can support mammary epithelial cells lining either the external (top and lower left) or internal (lower right) surface of the capillaries, providing directional and compartmentalized absorption of nutrients and secretion of milk.
Figure 5:
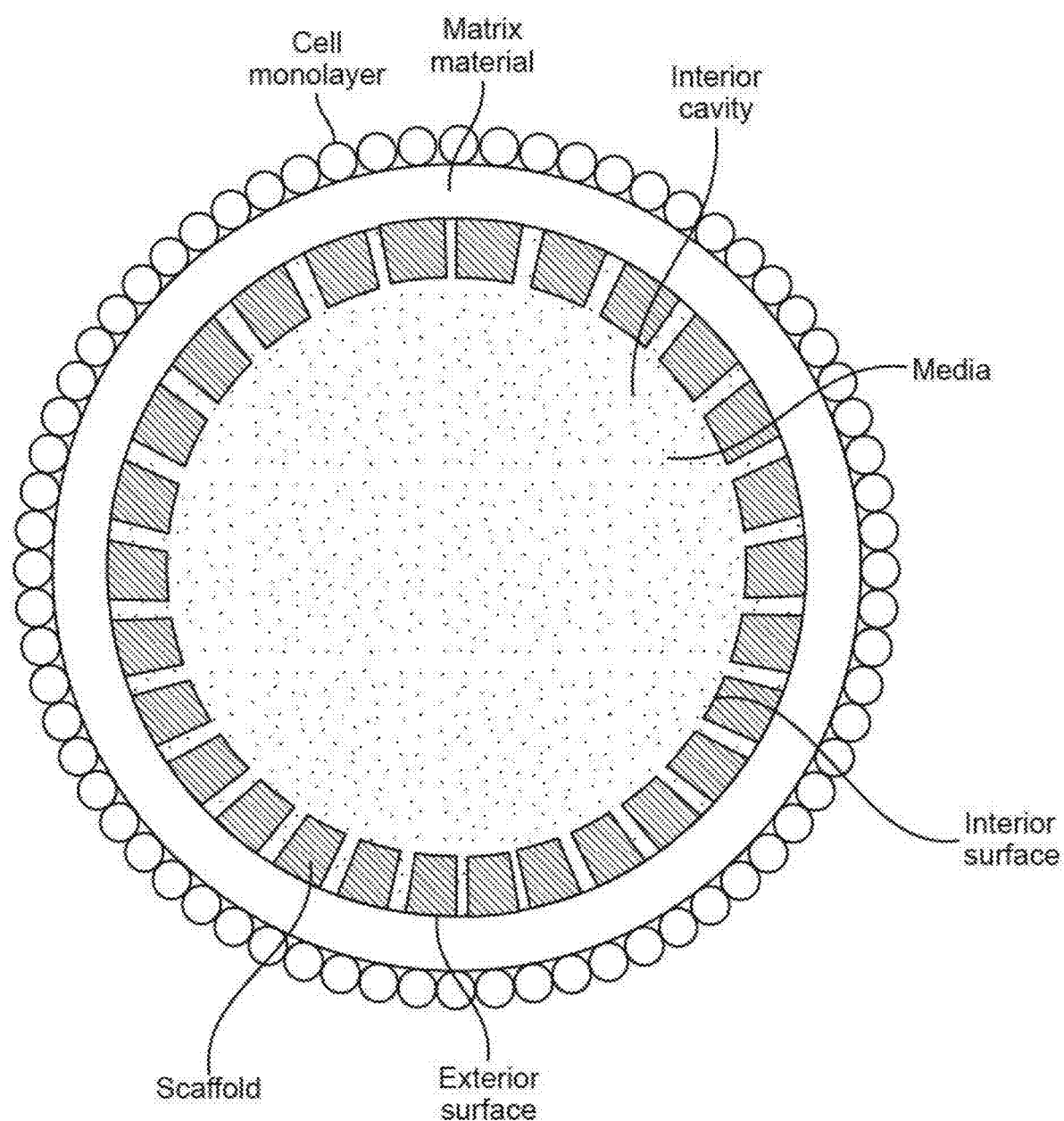
FIG. 5 exemplifies a cross-section of three-dimensional cell construct. The construct is made up of a scaffold having an interior surface defining an interior cavity/basal chamber and an exterior surface. The interior cavity/basal chamber comprises cell culture media. A matrix material sits on top of the exterior surface of the scaffold. Pores transverse the scaffold from the interior surface to the exterior surface, allowing cell media to contact the basal surface of the cells of the cell monolayer disposed on the matrix material.
Figure 6:
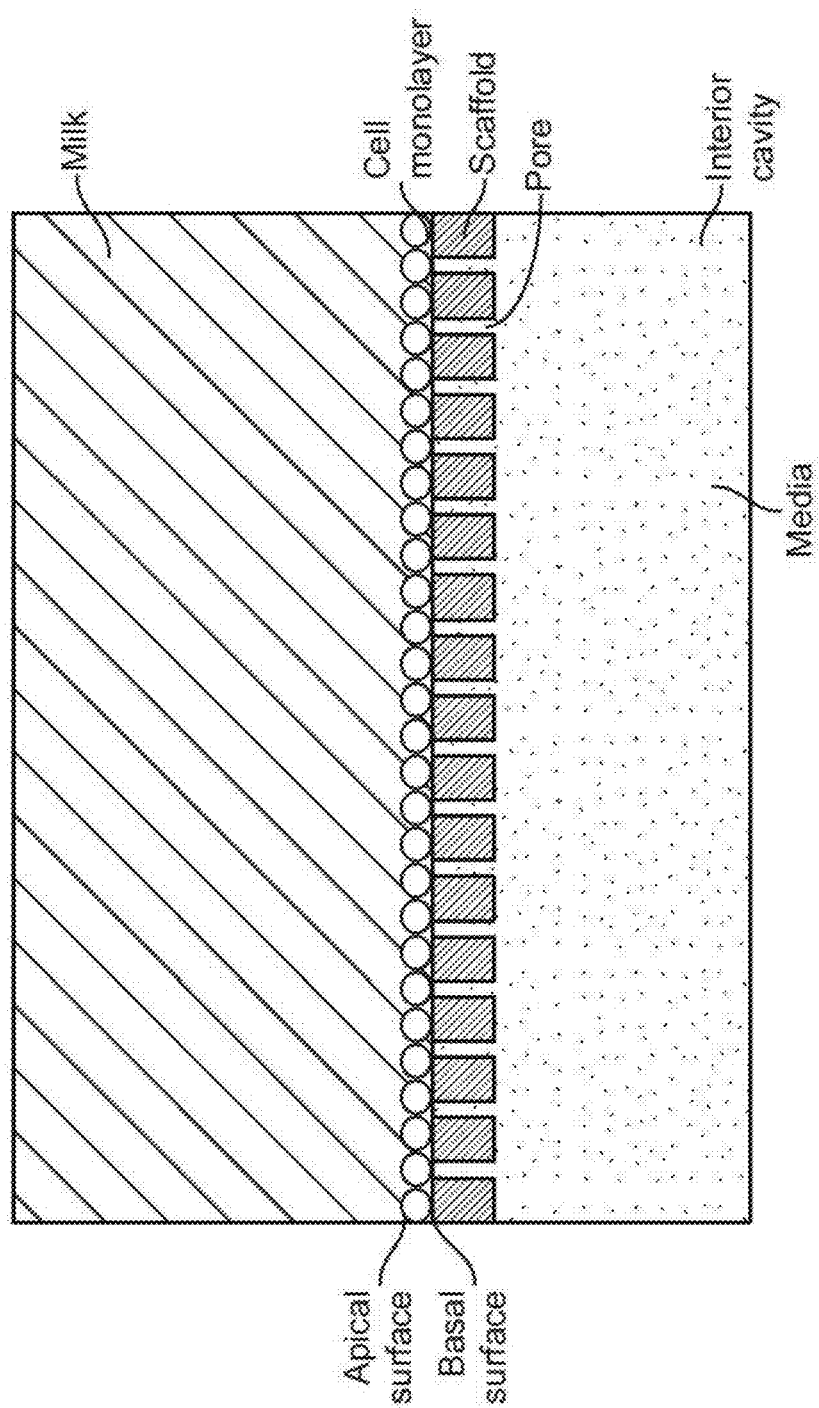
FIG. 6 exemplifies a bioreactor for producing a cultured milk product. The bioreactor is made up of a cell construct and an apical chamber. The cell construct is made up of a scaffold having an interior surface defining an interior cavity/basal chamber and an exterior surface. The cavity comprises cell culture media. A matrix material sits on top of the exterior surface of the scaffold. Pores transverse the scaffold from the interior surface to the exterior surface, allowing cell media to contact the basal surface of the cells of the cell monolayer disposed on the matrix material. The apical surface of the cells of the cell monolayer secrete the milk/cultured milk product into the apical chamber. The apical chamber and the interior cavity/basal chamber are separated by the cell monolayer.
Figure 7:
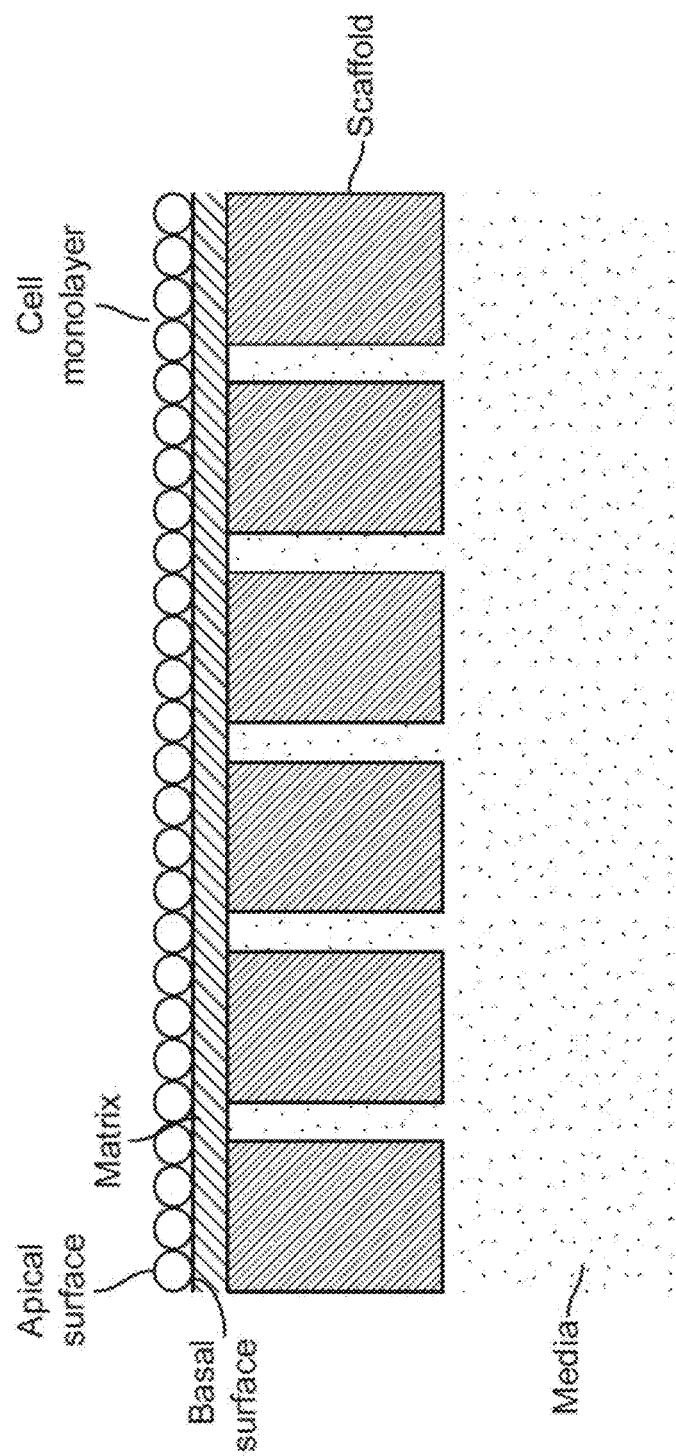
FIG. 7 exemplifies a cell construct. The construct is made up of a scaffold having an interior surface defining an interior cavity/basal chamber and an exterior surface. The interior cavity/basal chamber comprises cell.
Figure 8:
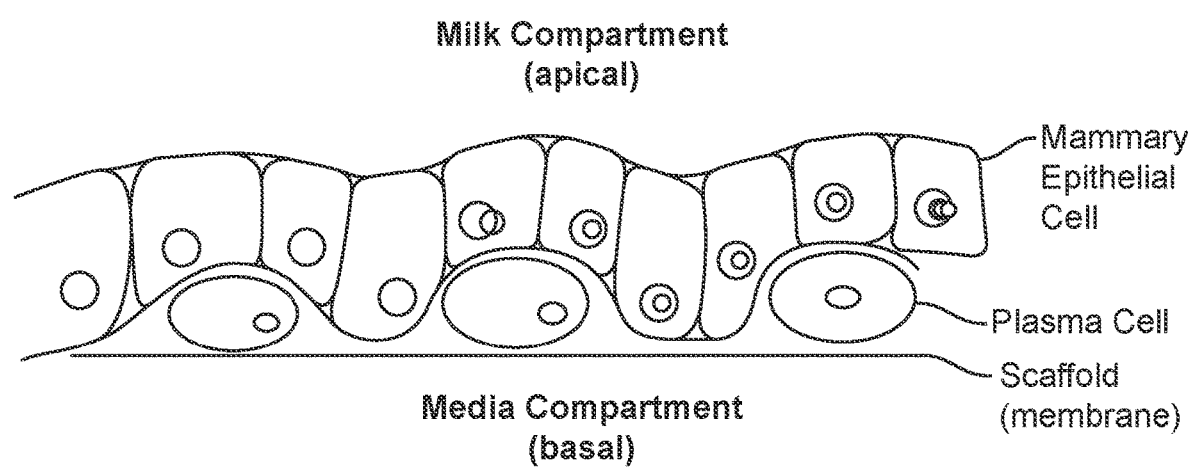
FIG. 8 exemplifies a cell construct having mammary epithelial cells (MECs) and plasma cells. The plasma cells are adjacent to the scaffold. The MECs form a confluent monolayer above (and in some instances, in between) the plasma cells, with the apical side of the MECs facing the apical compartment (or, milk compartment). The plasma cells secrete IgA, which then binds to a receptor on the basolateral surface of the MECs, triggering internalization of the antibody-receptor complex and further processing of the antibody into sIgA as it transits toward the apical surface (not shown).

Following the isolation and expansion of mammary epithelial cells, the cells are suspended in a chemically defined nutrient medium composed of food-grade components and inoculated into a culture apparatus that has been pre-coated with a mixture of extracellular matrix proteins, such as collagen, laminin, and/or fibronectin. The cell culture apparatus is any design that allows for the compartmentalized absorption of nutrients and secretion of product from a polarized, confluent, epithelial monolayer. Examples include hollow fiber and microstructured scaffold bioreactors (see, e.g., FIGS. 3 and 4, respectively). Alternatives include other methods of 3-dimensional tissue culture, such as the preparation of decellularized mammary gland as a scaffold, repopulated with stem cells to produce a functional organ in vitro, or collection of milk from the lumen of mammary epithelial cell organoids or "mammospheres" grown either in a hydrogel matrix or in suspension.

The apparatus includes sealed housing that maintains a temperature of about 37° C. in a humidified atmosphere of about 5% $CO_2$. Glucose uptake is monitored to evaluate the growth of the culture as the cells proliferate within the bioreactor. Stabilization of glucose consumption indicates that the cells have reached a confluent, contact-inhibited state. The integrity of the monolayer is ensured using transepithelial electrical resistance. Sensors monitor concentrations of dissolved 02 and $CO_2$ in the media at multiple locations. A computerized pump circulates media through the bioreactor at a rate that balances the delivery of nutrients with the removal of metabolic waste such as ammonia and lactate. Media can be recycled through the system after removal of waste using Lactate Supplementation and Adaptation technology (Freund et al. 2018 *Int J Mol Sci.* 19(2)) or by passing through a chamber of packed zeolite.

Stimulation of milk production. In vivo and in cultured mammary epithelial cells, the production and secretion of milk is stimulated by prolactin. In culture, prolactin can be supplied exogenously in the nutrient media at concentrations approximating those observed in the body during lactation, e.g., about 20 ng/mL to about 200 ng/mL. Purified prolactin can be obtained commercially; however, alternative methods of providing prolactin or stimulating lactation are employed, including expression and purification of the recombinant protein from microbial or mammalian cell cultures. Alternatively, conditioned media prepared by culturing cells that express and secrete prolactin can be applied to mammary epithelial cell cultures to stimulate lactation. Bioreactors can be set up in series such that media passing through a culture of cells expressing prolactin or other key media supplements is conditioned prior to exposure to mammary cells grown in a compartmentalizing culture apparatus as described.

Other approaches to upregulate milk production and/or spare the use of exogenous prolactin include molecular manipulation of the signaling pathways that are regulated by binding of prolactin to its receptor on the surface of mammary epithelial cells, such as the following: (a) expression of constructs targeting the posttranslational modification of prolactin; (b) expression of alternative isotypes of the prolactin receptor; (c) expression of a chimeric prolactin receptor in which the extracellular domain is exchanged with the binding site for a different ligand; (d) introduction of a gene encoding a constitutively or conditionally active prolactin receptor or modified versions of its downstream effectors such as STAT5 or Akt; (e) knockout or modification of the PER2 circadian gene; and/or (f) molecular approaches aimed at increasing the rate of nutrient uptake at the basal surface of the mammary epithelial monolayer.

Collection of milk. Secreted milk is collected continuously or at intervals through, for example, a port installed in the apical compartment of the culture apparatus. A vacuum is applied to the port to facilitate collection and also contributes to the stimulation of further production. The collected milk is packaged into sterile containers and sealed for distribution, frozen or lyophilized for storage, or processed for the extraction of specific components.

The present invention provides mammary epithelial cell cultures for the production of milk for nutritional use. In addition to human breast milk, this method may be used to produce milk from other mammalian species, for example, for human consumption or veterinary use. Because it has not been previously possible to produce milk outside the body, this technology may result in novel commercial opportunities, in addition to providing an alternative mode of production for existing products. The social and economic effects of the commercial development of this technology are broad and far reaching. Production of human breast milk from cultured cells may provide a means to address infant malnutrition in food-scarce communities, provide essential nutrients to premature infants who are unable to breastfeed, and offer mothers a new option for feeding their babies that provides optimal nutrition with the convenience of infant formula. Production of cow or goat milk provides an opportunity to reduce the environmental, social, and animal welfare effects of animal agriculture. The process described here addresses an important gap in the emerging field of cellular agriculture and introduces an opportunity to dramatically update the human food supply without compromising our biological and cultural attachment to the most fundamental of our nutrition sources.

Example 3: Manufacturing Milk Compositions Comprising Immunoglobins

Primary mammary tissue is collected from a healthy donor. CD20+ immune cells and mammary epithelial cell populations are sorted by FACS analysis using known markers for the myoepithelial and luminal epithelial cell populations. The isolated mammary cells and immune cells are immortalized prior to co-culture of the cells. The immortalized immune cells are co-cultured with immortalized isolated mammary epithelial cells in a hollow fiber bioreactor and grown to confluence. The culture is stimulated with prolactin to stimulate milk production. The secretory cell culture product comprising immunoglobulins, including secretory IgA is then harvested by a non-disruptive withdrawal mechanism.

Example 4: Manufacturing of Immunotherapy Compositions from Co-Cultured Mucosal Epithelial Cells and Immune Cells Primary mammary epithelial cells and CD20+ immune cells are harvested from tissue derived from patients who have recovered from a mucosal infection. Patients are selected that have been tested positive for serum that exhibits viral neutralization activity. The CD20+ immune cells are co-cultured with the mammary epithelial cells in a hollow fiber bioreactor. The immune cells are grown in 2-D culture, followed by inoculation into a hollow fiber bioreactor and grown to maximum density (i.e., superconfluence) within the bioreactor. The co-culture of the mucosal epithelial cells and immune cells are stimulated to produce immunoglobins including secretory IgA. The co-culture is stimulated with one or more of a stimulant selected from, a viral protein, a viral protein fragment, prolactin, TGF-β, and interleukin 10 (IL-10). The products from the co-culture of mucosal epithelial cells and stimulated immune cells are harvested using a standard vacuum method. In certain embodiments, the secreted product is purified. The immunoglobulins are purified from the harvested secreted product. The purified secreted product is formulated as an inhalant for human pulmonary administration and is effective in the treatment of respiratory infection.

Example 5: Treatment Of Respiratory Infection With Immunotherapy Composition From Co-Cultured Mucosal Epithelial Cells And Immune Cells An immunotherapy composition produced as described above in Example 3 is formulated as an inhalant and is administered to a patient harboring a respiratory infection, in an amount effective to treat the infection. The immunotherapy composition is effective at reducing the severity of symptoms of the infection in the patient.

The foregoing examples are illustrative of the present disclosure and are not to be construed as limiting thereof. Although the disclosure has been described in detail with reference to preferred embodiments, variations and modifications exist within the scope and spirit of the disclosure as described and defined in the following claims.

INFORMAL SEQUENCE LISTING

SEQ ID NO: 1: Human Prolactin Receptor (GenBank Accession Number AAD32032.1)
MKENVASATVFTLLLFLNTCLLNGQLPPGK-PEIFKCRSPNKETFTCWWRPGTDGGLPTNYSL TYHREGETLMHECPDYITGGPN-SCHFGKQYTSMWRTYIMMVNATNQMGSSFSDELY-VDVT YIVQPDPPLELAVEVKQPE-DRKPYLWIKWSPPTLIDLKTGWFTLLYEIRLKPEKA AEWEIHFA GQQTEFKILSLHPGQKYLVQVRCKPDHGYW-SAWSPATFIQIPSDFTMNDTTVWISVAVLSA VICLIIV-WAVALKGYSMVTCIFPPVPGPKIKGFDAHLLEKGK-SEELLSALGCQDFPPTSDYED LLVEYLEVDDSEDQHLMSVHSKEHPSQGMKP-TYLDPDTDSGRGSCDSPSLLSEKCEEPQAN PSTFYDPEVIEKPENPETTHTWDPQCISMEGKIPYF-HAGGSKCSTWPLPQPSQHNPRSSYHNI TDVCELAVGPAGAPATLLNEAGKDALKSSQTIKS-REEGKATQQREVESFHSETDQDTPWLL PQEKTPFG-SAKPLDYVEIHKVNKD-GALSLLPKQRENSGKPKKPGTPENNKEYAKVSGVMD NNILVLVPDPHAKNVACFEESAKE-APPSLEQNQAEKALANFTATSSKCRLQLG-GLDYLDPA CFTHSFH SEQ ID NO: 2: Human Period Circadian Protein Homolog 2 (GenBank Accession Number NM 022817)
MNGYAEFPPSPSNPTKEPVEPQP-SQVPLQEDVDMSSGSSGHETNENCST-GRDSQGSDCDDS GKJELGMLVEPPDAR-QSPDTFSLMMAKSEHNPSTSG CSSDQSSKVDTHKEL1KTLKELKVH LPADK-KAKGKASTLATLKYALRSVKQVKANEEYYQLL-MSSEGHPCGADVPSYTVEEMESV TSE-HIVKNADMFAVAVSLVSGKILYISDQVASIFHCKRD AFSDAKFVEFLAPHDVGVFHSFT SPYKLPLWSMCSGADSFTQECMEEKSFFCRVSVRK-SHENEIRYHPFRMTPYLVKVRDQQGA ESQLCCLL-LAERVHSGYEAPRIPPEKRIFTTTHTPNCLFQDVDER-AVPLLGYLPQDLIETPVL VQLHPSDRPLMLAIHKKILQSGGQPFDYSPIRFRA-RNGEYITLDTSWSSFINPWSRKISFIIGRH KVRVG-PLNEDVFAAHPCTEEKALHPSIQELTE-QIHRLLLQPVPHSGSSGYGSLGSNGSHEHL MSQTSSSDSNGHEDSRRRRAEICKNGNKTKNRSHY-SHESGEQKKKSVTEMQTNPPAEKKA VPAMEKD-SLGVSFPEELACKNQPTCSYQQISCLDS-VIRYLESCNEAATLKRKCEFPANVPAL RSSDKRKATVSPGPHAGEAEPPSRVNSRTGVGTHLT-SLALPGKAESVASLTSQCSYSSTIVH VGDKKPQPELEMVEDAASGPESLD-CLAGPALACGLSQEKEPFKKLGLTKEVLAAHTQ-KEEQ SFLQKFKEIRKLSIFQSHCHYYLQERSKGQP-SERTAPGLRNTSGIDSPWKKTGKNRKLKSKR VKPRDSSESTGSGGPVSARPPLVGLNA-TAWSPSDTSQSSCPAVPFPAPVPAAYSLPVFPAPGT VAAPPAP-PHASFTVPAVPVDLQHQFAVQPPPFPAPLAPVMA-FMLPSYSFPSGTPNLPQAFFPS QPQFPSHPTLTSE-MASASQPEFPEGGTGAMGTTGATETAAVGADCKPG TSRDQQPKAPLTR DEPSDTQNSDALST-SSGLLNLLLNEDLCSASGSAASESLGSGSLGC-DASPSGAGSSDTSHTSK YFGSIDSSENNHKAKMNTG-MEESEHFIKCVLQDPIWLLMADADSSVMMTYQLP SRNLEAV LKEDREKLKLLQKLQPRFTESQKQEL-REVHQWMQTGGLPAAIDVAECVYCENKEKGNICIP YEEDIPSLGLSEVSDTKEDENGSPLNHRIEEQT SEQ ID NO: 3: Human Isoform 4 of Prolactin Receptor (GenBank Accession Number AF416619; Trott et al. 2003 J. Mol. Endocrinol 30(1):31-47)
MKENVASATVFTLLLFLNTCLLNGQLPPGK-PEIFKCRSPNKETFTCWWRPGTDGGLPTNYSL TYHREGETLMHECPDYITGGPN-SCHFGKQYTSMWRTYIMMVNATNQMGSSFSDELY-VDVT YIVQPDPPLELAVEVKQPE-DRKPYLWIKWSPPTLIDLKTGWFTLLYEIRLKPEK AAEWEIHFA GQQTEFKILSLHPGQKYLVQVRCK-PDHGYWSAWSPATFIQIPSDFTMNDTTVWISVAVLSA VICLIIVWAVALKGYSMVTCIFPPVPGPKIKGFDAHL-LEKGKSEELLSALGCQDFPPTSDYED LLVEYLEVDD-SEDQHLMSVHSKEHPSQGDPLMLGASHYKNLKSYR-PRKISSQGRLAVFTKA TLTTVQ SEQ ID NO: 4. STA5A Human Signal Transducer and Activator of Transcription 5A Fused at 3' End to Amino Acids 757-1129 of JAK2 Human Tyrosine-Protein Kinase
MAGWIQAQQL QGDALRQMQV LYGQHFPIEV RHYLAQWIES QPWDAIDLDN PQDRAQATQL LEGLVQELQK KAEHQVGEDG FLLKIKLGHY ATQLQKTYDR CPLELVRCIR HILYNEQRLV REANNCSSPA GILVDAMSQK HLQINQTFEE LRLVTQDTEN ELKKLQQTQE YFIIQYQESL RIQAQFAQLA QLSPQERLSR ETALQQKQVS LEAWLQREAQ TLQQYRVELA EKHQKTLQLL RKQQTIILDD ELIQWKRRQQ LAGNGGPPEG SLDVLQSWCE KLAEIIWQNR QQIRRAEHLC QQLPIPGPVE EMLAEVNATI TDIISALVTS TFIIEKQPPQ VLKTQTKFAA TVRLLVGGKL NVHMNPPQVK ATIISEQQAK SLLKNENTRN ECSGEILNNC CVMEYHQATG TLSAHFRNMS LKRIKRADRR GAESVTEEKF TVLFESQFSV GSNELVFQVK TLSLPWVIV HGSQDHNATA TVLWD-NAFAE PGRVPFAVPD KVLWPQLCEA LNMKFKAEVQ SNRGLTKENL VFLAQKLFNN SSSHLEDYSG LSVSWSQFNR ENLPGWNYTF WQWFDGVMEV LKKHHKPHWN DGAILGFVNK QQAHDLLINK PDGT-FLLRFS DSEIGGITIA WKFDSPERNL WNLKPFTTRD FSIRSLADRL GDLSYLIYVF PDRPKDEVFS KYYTPV-LAKA VDGYVKPQIK QWPEFVNAS ADAGGSSATY MDQAPSPAVC PQAPYNMYPQ NPDHVLDQDG EFDL-DETMDV ARHVEELLRR PMDSLDSRLS PPAGLFT-SAR GSLSLDSQ RKLQFYEDRH QLPAPKWAEL ANLINNCMDY EPDFRPSFRA IIRDLNSLFT PDYELL-TEND MLPNMRIGAL GFSGAFEDRD PTQFEERHLK FLQQLGKGNF GSVEMCRYDP LQDNTGEWA VKKLQHSTEE HLRDFEREIE ILKSLQHDNI VKYKGVCYSA GRRNLKLIME YLPYGSLRDY LQKH-KERIDH IKLLQYTSQI CKGMEYLGTK RYIHRDLATR NILVENENRV KIGDFGLTKV LPQDKEYYKV KEPGESPIFW YAPESLTESK FSVASDVWSF GWLY-ELFTY IEKSKSPPAE FMRMIGNDKQ GQMIVFHLIE LLKNNGRLPR PDGCPDEIYM IMTECWNNNV NQRPSFRDLA LRVDQIRDN.

What is claimed is:

1. A method of producing an isolated milk product comprising secretory IgA (sIgA) from cultured mammary cells and plasma cells, the method comprising:
   a. culturing a live cell construct in a bioreactor under conditions which produce the milk product, said cell construct comprising:
      i. a three-dimensional scaffold having an exterior surface, an interior surface defining an interior cavity, and a plurality of pores extending from the interior surface to the exterior surface;
      ii. a matrix material disposed on the exterior surface of the three-dimensional scaffold;
      iii. a culture medium disposed within the interior cavity and in fluidic contact with the interior surface;
      iv. a plurality of live plasma cells disposed on the matrix material; and
      v. a confluent monolayer of polarized mammary cells disposed on the plurality of plasma cells, wherein the mammary cells are selected from the group consisting of: live mammary epithelial cells, and live mammary myoepithelial cells, wherein the polarized mammary cells comprise an apical surface from which the milk product is secreted and a basal surface;
      said bioreactor comprising an apical compartment that is in fluidic contact with the apical surface of the live mammary cells, is substantially isolated from the interior cavity of the live cell construct, and is substantially free of cell culture medium; and
   b. isolating the milk product secreted into the apical compartment from the apical surface of the live mammary cells and the plasma cells.

2. The method of claim 1, wherein the monolayer of polarized mammary cells is at least 70% confluent, at least 80% confluent, at least 90% confluent, at least 95% confluent, at least 99% confluent, or 100% confluent.

3. The method of claim 1, wherein at least 70%, at least 80%, at least 90%, at least 95%, at least 99%, or 100% of the mammary cells are polarized in the same orientation.

4. The method of claim 1, wherein total cell density of mammary cells within the bioreactor is at least $10^{11}$; and alternatively wherein total surface area of mammary cells within the bioreactor is at least 1.5 $m^2$.

5. The method of claim 1, wherein total cell density of plasma cells in the bioreactor is about 200 to 500 plasma cells per $mm^2$.

6. The method of claim 1, wherein the culturing is carried out at a temperature of about 27° C. to about 39° C.

7. The method of claim 1, wherein the culturing is carried out at an atmospheric concentration of $CO_2$ of about 4% to about 6%.

8. A live cell construct, comprising:
   a. a three dimensional scaffold having an exterior surface, an interior surface defining an interior cavity/basal chamber, and a plurality of pores extending from the interior surface to the exterior surface;
   b. a matrix material disposed on the exterior surface of the three-dimensional scaffold;
   c. a plurality of live plasma cells disposed on the matrix material;

d. an at least 70% confluent monolayer of live polarized mammary cells disposed on the plurality of live plasma cells and on the matrix material, wherein the live mammary cells are selected from the group consisting of: live mammary epithelial cells, and live mammary myoepithelial cells, and wherein the live polarized mammary cells comprise an apical surface from which the milk product is secreted and a basal surface; and e. a culture medium disposed within the interior cavity/basal chamber and in fluidic contact with the interior surface, wherein the culture medium is substantially isolated from the apical surface of the live mammary cells.

9. The cell construct of claim 8, wherein the basal surface of the mammary cells is in fluidic contact with the culture medium.

10. The cell construct of claim 8, wherein at least 70%, at least 80%, at least 90%, at least 95%, at least 99%, or 100% of the mammary cells are polarized in the same orientation.

11. The cell construct of claim 8, wherein the monolayer of polarized mammary cells is at least 70% confluent, at least 80% confluent, at least 90% confluent, at least 95% confluent, at least 99% confluent, or 100% confluent.

12. The cell construct of claim 8, wherein the mammary cells comprise a constitutively active prolactin receptor protein.

13. The cell construct of claim 8, wherein the culture medium comprises prolactin.

\* \* \* \* \*

SEQUENCE LISTING

<160> NUMBER OF SEQ ID NOS: 4

<210> SEQ ID NO 1
<211> LENGTH: 622
<212> TYPE: PRT
<213> ORGANISM: Homo sapiens

<400> SEQUENCE: 1

```
Met Lys Glu Asn Val Ala Ser Ala Thr Val Phe Thr Leu Leu Leu Phe
1               5                   10                  15

Leu Asn Thr Cys Leu Leu Asn Gly Gln Leu Pro Pro Gly Lys Pro Glu
            20                  25                  30

Ile Phe Lys Cys Arg Ser Pro Asn Lys Glu Thr Phe Thr Cys Trp Trp
        35                  40                  45

Arg Pro Gly Thr Asp Gly Gly Leu Pro Thr Asn Tyr Ser Leu Thr Tyr
    50                  55                  60

His Arg Glu Gly Glu Thr Leu Met His Glu Cys Pro Asp Tyr Ile Thr
65                  70                  75                  80

Gly Gly Pro Asn Ser Cys His Phe Gly Lys Gln Tyr Thr Ser Met Trp
                85                  90                  95

Arg Thr Tyr Ile Met Met Val Asn Ala Thr Asn Gln Met Gly Ser Ser
                100                 105                 110

Phe Ser Asp Glu Leu Tyr Val Asp Val Thr Tyr Ile Val Gln Pro Asp
            115                 120                 125

Pro Pro Leu Glu Leu Ala Val Glu Val Lys Gln Pro Glu Asp Arg Lys
    130                 135                 140

Pro Tyr Leu Trp Ile Lys Trp Ser Pro Pro Thr Leu Ile Asp Leu Lys
145                 150                 155                 160

Thr Gly Trp Phe Thr Leu Leu Tyr Glu Ile Arg Leu Lys Pro Glu Lys
                165                 170                 175

Ala Ala Glu Trp Glu Ile His Phe Ala Gly Gln Gln Thr Glu Phe Lys
            180                 185                 190

Ile Leu Ser Leu His Pro Gly Gln Lys Tyr Leu Val Gln Val Arg Cys
        195                 200                 205

Lys Pro Asp His Gly Tyr Trp Ser Ala Trp Ser Pro Ala Thr Phe Ile
    210                 215                 220

Gln Ile Pro Ser Asp Phe Thr Met Asn Asp Thr Thr Val Trp Ile Ser
225                 230                 235                 240

Val Ala Val Leu Ser Ala Val Ile Cys Leu Ile Ile Val Trp Ala Val
                245                 250                 255

Ala Leu Lys Gly Tyr Ser Met Val Thr Cys Ile Phe Pro Pro Val Pro
            260                 265                 270

Gly Pro Lys Ile Lys Gly Phe Asp Ala His Leu Leu Glu Lys Gly Lys
        275                 280                 285

Ser Glu Glu Leu Leu Ser Ala Leu Gly Cys Gln Asp Phe Pro Pro Thr
    290                 295                 300

Ser Asp Tyr Glu Asp Leu Leu Val Glu Tyr Leu Glu Val Asp Asp Ser
305                 310                 315                 320

Glu Asp Gln His Leu Met Ser Val His Ser Lys Glu His Pro Ser Gln
                325                 330                 335

Gly Met Lys Pro Thr Tyr Leu Asp Pro Asp Thr Asp Ser Gly Arg Gly
            340                 345                 350

Ser Cys Asp Ser Pro Ser Leu Leu Ser Glu Lys Cys Glu Glu Pro Gln
        355                 360                 365

Ala Asn Pro Ser Thr Phe Tyr Asp Pro Glu Val Ile Glu Lys Pro Glu
    370                 375                 380

Asn Pro Glu Thr Thr His Thr Trp Asp Pro Gln Cys Ile Ser Met Glu
385                 390                 395                 400

Gly Lys Ile Pro Tyr Phe His Ala Gly Gly Ser Lys Cys Ser Thr Trp
                405                 410                 415
```

```
Pro Leu Pro Gln Pro Ser Gln His Asn Pro Arg Ser Ser Tyr His Asn
            420                 425                 430

Ile Thr Asp Val Cys Glu Leu Ala Val Gly Pro Ala Gly Ala Pro Ala
            435                 440                 445

Thr Leu Leu Asn Glu Ala Gly Lys Asp Ala Leu Lys Ser Ser Gln Thr
            450                 455                 460

Ile Lys Ser Arg Glu Glu Gly Lys Ala Thr Gln Gln Arg Glu Val Glu
465                 470                 475                 480

Ser Phe His Ser Glu Thr Asp Gln Asp Thr Pro Trp Leu Leu Pro Gln
                485                 490                 495

Glu Lys Thr Pro Phe Gly Ser Ala Lys Pro Leu Asp Tyr Val Glu Ile
            500                 505                 510

His Lys Val Asn Lys Asp Gly Ala Leu Ser Leu Leu Pro Lys Gln Arg
            515                 520                 525

Glu Asn Ser Gly Lys Pro Lys Lys Pro Gly Thr Pro Glu Asn Asn Lys
            530                 535                 540

Glu Tyr Ala Lys Val Ser Gly Val Met Asp Asn Asn Ile Leu Val Leu
545                 550                 555                 560

Val Pro Asp Pro His Ala Lys Asn Val Ala Cys Phe Glu Glu Ser Ala
                565                 570                 575

Lys Glu Ala Pro Pro Ser Leu Glu Gln Asn Gln Ala Glu Lys Ala Leu
            580                 585                 590

Ala Asn Phe Thr Ala Thr Ser Ser Lys Cys Arg Leu Gln Leu Gly Gly
            595                 600                 605

Leu Asp Tyr Leu Asp Pro Ala Cys Phe Thr His Ser Phe His
            610                 615                 620

<210> SEQ ID NO 2
<211> LENGTH: 1205
<212> TYPE: PRT
<213> ORGANISM: Homo sapiens

<400> SEQUENCE: 2

Met Asn Gly Tyr Ala Glu Phe Pro Pro Ser Pro Ser Asn Pro Thr Lys
1               5                   10                  15

Glu Pro Val Glu Pro Gln Pro Ser Gln Val Pro Leu Gln Glu Asp Val
            20                  25                  30

Asp Met Ser Ser Gly Ser Ser Gly His Glu Thr Asn Glu Asn Cys Ser
        35                  40                  45

Thr Gly Arg Asp Ser Gln Gly Ser Asp Cys Asp Asp Ser Gly Lys Glu
    50                  55                  60

Leu Gly Met Leu Val Glu Pro Pro Asp Ala Arg Gln Ser Pro Asp Thr
65                  70                  75                  80

Phe Ser Leu Met Met Ala Lys Ser Glu His Asn Pro Ser Thr Ser Gly
                85                  90                  95

Cys Ser Ser Asp Gln Ser Ser Lys Val Asp Thr His Lys Glu Leu Ile
            100                 105                 110

Lys Thr Leu Lys Glu Leu Lys Val His Leu Pro Ala Asp Lys Lys Ala
            115                 120                 125

Lys Gly Lys Ala Ser Thr Leu Ala Thr Leu Lys Tyr Ala Leu Arg Ser
            130                 135                 140

Val Lys Gln Val Lys Ala Asn Glu Glu Tyr Tyr Gln Leu Leu Met Ser
145                 150                 155                 160

Ser Glu Gly His Pro Cys Gly Ala Asp Val Pro Ser Tyr Thr Val Glu
```

-continued

```
            165                 170                 175
Glu Met Glu Ser Val Thr Ser Glu His Ile Val Lys Asn Ala Asp Met
            180                 185                 190
Phe Ala Val Ala Val Ser Leu Val Ser Gly Lys Ile Leu Tyr Ile Ser
            195                 200                 205
Asp Gln Val Ala Ser Ile Phe His Cys Lys Arg Asp Ala Phe Ser Asp
            210                 215                 220
Ala Lys Phe Val Glu Phe Leu Ala Pro His Asp Val Gly Val Phe His
225                 230                 235                 240
Ser Phe Thr Ser Pro Tyr Lys Leu Pro Leu Trp Ser Met Cys Ser Gly
                    245                 250                 255
Ala Asp Ser Phe Thr Gln Glu Cys Met Glu Glu Lys Ser Phe Phe Cys
                    260                 265                 270
Arg Val Ser Val Arg Lys Ser His Glu Asn Glu Ile Arg Tyr His Pro
                    275                 280                 285
Phe Arg Met Thr Pro Tyr Leu Val Lys Val Arg Asp Gln Gln Gly Ala
            290                 295                 300
Glu Ser Gln Leu Cys Cys Leu Leu Ala Glu Arg Val His Ser Gly
305                 310                 315                 320
Tyr Glu Ala Pro Arg Ile Pro Pro Glu Lys Arg Ile Phe Thr Thr Thr
                    325                 330                 335
His Thr Pro Asn Cys Leu Phe Gln Asp Val Asp Glu Arg Ala Val Pro
                    340                 345                 350
Leu Leu Gly Tyr Leu Pro Gln Asp Leu Ile Glu Thr Pro Val Leu Val
                    355                 360                 365
Gln Leu His Pro Ser Asp Arg Pro Leu Met Leu Ala Ile His Lys Lys
            370                 375                 380
Ile Leu Gln Ser Gly Gly Gln Pro Phe Asp Tyr Ser Pro Ile Arg Phe
385                 390                 395                 400
Arg Ala Arg Asn Gly Glu Tyr Ile Thr Leu Asp Thr Ser Trp Ser Ser
                    405                 410                 415
Phe Ile Asn Pro Trp Ser Arg Lys Ile Ser Phe Ile Ile Gly Arg His
                    420                 425                 430
Lys Val Arg Val Gly Pro Leu Asn Glu Asp Val Phe Ala Ala His Pro
            435                 440                 445
Cys Thr Glu Glu Lys Ala Leu His Pro Ser Ile Gln Glu Leu Thr Glu
450                 455                 460
Gln Ile His Arg Leu Leu Leu Gln Pro Val Pro His Ser Gly Ser Ser
            465                 470                 475                 480
Gly Tyr Gly Ser Leu Gly Ser Asn Gly Ser His Glu His Leu Met Ser
                    485                 490                 495
Gln Thr Ser Ser Ser Asp Ser Asn Gly His Glu Asp Ser Arg Arg Arg
            500                 505                 510
Arg Ala Glu Ile Cys Lys Asn Gly Asn Lys Thr Lys Asn Arg Ser His
            515                 520                 525
Tyr Ser His Glu Ser Gly Glu Gln Lys Lys Ser Val Thr Glu Met
            530                 535                 540
Gln Thr Asn Pro Pro Ala Glu Lys Lys Ala Val Pro Ala Met Glu Lys
545                 550                 555                 560
Asp Ser Leu Gly Val Ser Phe Pro Glu Glu Leu Ala Cys Lys Asn Gln
                    565                 570                 575
Pro Thr Cys Ser Tyr Gln Gln Ile Ser Cys Leu Asp Ser Val Ile Arg
                    580                 585                 590
```

```
Tyr Leu Glu Ser Cys Asn Glu Ala Ala Thr Leu Lys Arg Lys Cys Glu
        595                 600                 605

Phe Pro Ala Asn Val Pro Ala Leu Arg Ser Ser Asp Lys Arg Lys Ala
        610                 615                 620

Thr Val Ser Pro Gly Pro His Ala Gly Glu Ala Glu Pro Pro Ser Arg
625                 630                 635                 640

Val Asn Ser Arg Thr Gly Val Gly Thr His Leu Thr Ser Leu Ala Leu
                645                 650                 655

Pro Gly Lys Ala Glu Ser Val Ala Ser Leu Thr Ser Gln Cys Ser Tyr
                660                 665                 670

Ser Ser Thr Ile Val His Val Gly Asp Lys Lys Pro Gln Pro Glu Leu
                675                 680                 685

Glu Met Val Glu Asp Ala Ala Ser Gly Pro Glu Ser Leu Asp Cys Leu
        690                 695                 700

Ala Gly Pro Ala Leu Ala Cys Gly Leu Ser Gln Glu Lys Glu Pro Phe
705                 710                 715                 720

Lys Lys Leu Gly Leu Thr Lys Glu Val Leu Ala Ala His Thr Gln Lys
                725                 730                 735

Glu Glu Gln Ser Phe Leu Gln Lys Phe Lys Glu Ile Arg Lys Leu Ser
        740                 745                 750

Ile Phe Gln Ser His Cys His Tyr Tyr Leu Gln Glu Arg Ser Lys Gly
        755                 760                 765

Gln Pro Ser Glu Arg Thr Ala Pro Gly Leu Arg Asn Thr Ser Gly Ile
        770                 775                 780

Asp Ser Pro Trp Lys Lys Thr Gly Lys Asn Arg Lys Leu Lys Ser Lys
785                 790                 795                 800

Arg Val Lys Pro Arg Asp Ser Ser Glu Ser Thr Gly Ser Gly Gly Pro
                805                 810                 815

Val Ser Ala Arg Pro Pro Leu Val Gly Leu Asn Ala Thr Ala Trp Ser
                820                 825                 830

Pro Ser Asp Thr Ser Gln Ser Ser Cys Pro Ala Val Pro Phe Pro Ala
        835                 840                 845

Pro Val Pro Ala Ala Tyr Ser Leu Pro Val Phe Pro Ala Pro Gly Thr
        850                 855                 860

Val Ala Ala Pro Pro Ala Pro Pro His Ala Ser Phe Thr Val Pro Ala
865                 870                 875                 880

Val Pro Val Asp Leu Gln His Gln Phe Ala Val Gln Pro Pro Pro Phe
                885                 890                 895

Pro Ala Pro Leu Ala Pro Val Met Ala Phe Met Leu Pro Ser Tyr Ser
                900                 905                 910

Phe Pro Ser Gly Thr Pro Asn Leu Pro Gln Ala Phe Phe Pro Ser Gln
        915                 920                 925

Pro Gln Phe Pro Ser His Pro Thr Leu Thr Ser Glu Met Ala Ser Ala
        930                 935                 940

Ser Gln Pro Glu Phe Pro Glu Gly Gly Thr Gly Ala Met Gly Thr Thr
945                 950                 955                 960

Gly Ala Thr Glu Thr Ala Ala Val Gly Ala Asp Cys Lys Pro Gly Thr
                965                 970                 975

Ser Arg Asp Gln Gln Pro Lys Ala Pro Leu Thr Arg Asp Glu Pro Ser
                980                 985                 990

Asp Thr Gln Asn Ser Asp Ala Leu Ser Thr Ser Ser Gly Leu Leu Asn
        995                 1000                1005
```

```
Leu Leu Leu Asn Glu Asp Leu Cys Ser Ala Ser Gly Ser Ala Ala
    1010                1015                1020

Ser Glu Ser Leu Gly Ser Gly Ser Leu Gly Cys Asp Ala Ser Pro
    1025                1030                1035

Ser Gly Ala Gly Ser Ser Asp Thr Ser His Thr Ser Lys Tyr Phe
    1040                1045                1050

Gly Ser Ile Asp Ser Ser Glu Asn Asn His Lys Ala Lys Met Asn
    1055                1060                1065

Thr Gly Met Glu Glu Ser Glu His Phe Ile Lys Cys Val Leu Gln
    1070                1075                1080

Asp Pro Ile Trp Leu Leu Met Ala Asp Ala Asp Ser Ser Val Met
    1085                1090                1095

Met Thr Tyr Gln Leu Pro Ser Arg Asn Leu Glu Ala Val Leu Lys
    1100                1105                1110

Glu Asp Arg Glu Lys Leu Lys Leu Leu Gln Lys Leu Gln Pro Arg
    1115                1120                1125

Phe Thr Glu Ser Gln Lys Gln Glu Leu Arg Glu Val His Gln Trp
    1130                1135                1140

Met Gln Thr Gly Gly Leu Pro Ala Ala Ile Asp Val Ala Glu Cys
    1145                1150                1155

Val Tyr Cys Glu Asn Lys Glu Lys Gly Asn Ile Cys Ile Pro Tyr
    1160                1165                1170

Glu Glu Asp Ile Pro Ser Leu Gly Leu Ser Glu Val Ser Asp Thr
    1175                1180                1185

Lys Glu Asp Glu Asn Gly Ser Pro Leu Asn His Arg Ile Glu Glu
    1190                1195                1200

Gln Thr
    1205

<210> SEQ ID NO 3
<211> LENGTH: 376
<212> TYPE: PRT
<213> ORGANISM: Homo sapiens

<400> SEQUENCE: 3

Met Lys Glu Asn Val Ala Ser Ala Thr Val Phe Thr Leu Leu Phe
1               5                   10                  15

Leu Asn Thr Cys Leu Leu Asn Gly Gln Leu Pro Pro Gly Lys Pro Glu
                20                  25                  30

Ile Phe Lys Cys Arg Ser Pro Asn Lys Glu Thr Phe Thr Cys Trp Trp
            35                  40                  45

Arg Pro Gly Thr Asp Gly Gly Leu Pro Thr Asn Tyr Ser Leu Thr Tyr
50                  55                  60

His Arg Glu Gly Glu Thr Leu Met His Glu Cys Pro Asp Tyr Ile Thr
65                  70                  75                  80

Gly Gly Pro Asn Ser Cys His Phe Gly Lys Gln Tyr Thr Ser Met Trp
                85                  90                  95

Arg Thr Tyr Ile Met Met Val Asn Ala Thr Asn Gln Met Gly Ser Ser
            100                 105                 110

Phe Ser Asp Glu Leu Tyr Val Asp Val Thr Tyr Ile Val Gln Pro Asp
        115                 120                 125

Pro Pro Leu Glu Leu Ala Val Glu Val Lys Gln Pro Glu Asp Arg Lys
    130                 135                 140

Pro Tyr Leu Trp Ile Lys Trp Ser Pro Pro Thr Leu Ile Asp Leu Lys
145                 150                 155                 160
```

Thr Gly Trp Phe Thr Leu Leu Tyr Glu Ile Arg Leu Lys Pro Glu Lys
                165                 170                 175

Ala Ala Glu Trp Glu Ile His Phe Ala Gly Gln Gln Thr Glu Phe Lys
            180                 185                 190

Ile Leu Ser Leu His Pro Gly Gln Lys Tyr Leu Val Gln Val Arg Cys
        195                 200                 205

Lys Pro Asp His Gly Tyr Trp Ser Ala Trp Ser Pro Ala Thr Phe Ile
    210                 215                 220

Gln Ile Pro Ser Asp Phe Thr Met Asn Asp Thr Thr Val Trp Ile Ser
225                 230                 235                 240

Val Ala Val Leu Ser Ala Val Ile Cys Leu Ile Ile Val Trp Ala Val
                245                 250                 255

Ala Leu Lys Gly Tyr Ser Met Val Thr Cys Ile Phe Pro Pro Val Pro
            260                 265                 270

Gly Pro Lys Ile Lys Gly Phe Asp Ala His Leu Leu Glu Lys Gly Lys
        275                 280                 285

Ser Glu Glu Leu Leu Ser Ala Leu Gly Cys Gln Asp Phe Pro Pro Thr
    290                 295                 300

Ser Asp Tyr Glu Asp Leu Leu Val Glu Tyr Leu Glu Val Asp Asp Ser
305                 310                 315                 320

Glu Asp Gln His Leu Met Ser Val His Ser Lys Glu His Pro Ser Gln
                325                 330                 335

Gly Asp Pro Leu Met Leu Gly Ala Ser His Tyr Lys Asn Leu Lys Ser
            340                 345                 350

Tyr Arg Pro Arg Lys Ile Ser Ser Gln Gly Arg Leu Ala Val Phe Thr
        355                 360                 365

Lys Ala Thr Leu Thr Thr Val Gln
    370                 375

<210> SEQ ID NO 4
<211> LENGTH: 1163
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Ala Gly Trp Ile Gln Ala Gln Gln Leu Gln Gly Asp Ala Leu Arg
1               5                   10                  15

Gln Met Gln Val Leu Tyr Gly Gln His Phe Pro Ile Glu Val Arg His
            20                  25                  30

Tyr Leu Ala Gln Trp Ile Glu Ser Gln Pro Trp Asp Ala Ile Asp Leu
        35                  40                  45

Asp Asn Pro Gln Asp Arg Ala Gln Ala Thr Gln Leu Leu Glu Gly Leu
    50                  55                  60

Val Gln Glu Leu Gln Lys Lys Ala Glu His Gln Val Gly Glu Asp Gly
65                  70                  75                  80

Phe Leu Leu Lys Ile Lys Leu Gly His Tyr Ala Thr Gln Leu Gln Lys
                85                  90                  95

Thr Tyr Asp Arg Cys Pro Leu Glu Leu Val Arg Cys Ile Arg His Ile
            100                 105                 110

Leu Tyr Asn Glu Gln Arg Leu Val Arg Glu Ala Asn Asn Cys Ser Ser
        115                 120                 125

Pro Ala Gly Ile Leu Val Asp Ala Met Ser Gln Lys His Leu Gln Ile

```
            130                 135                 140
Asn Gln Thr Phe Glu Glu Leu Arg Leu Val Thr Gln Asp Thr Glu Asn
145                 150                 155                 160

Glu Leu Lys Lys Leu Gln Gln Thr Gln Glu Tyr Phe Ile Ile Gln Tyr
                165                 170                 175

Gln Glu Ser Leu Arg Ile Gln Ala Gln Phe Ala Gln Leu Ala Gln Leu
            180                 185                 190

Ser Pro Gln Glu Arg Leu Ser Arg Glu Thr Ala Leu Gln Gln Lys Gln
                195                 200                 205

Val Ser Leu Glu Ala Trp Leu Gln Arg Glu Ala Gln Thr Leu Gln Gln
210                 215                 220

Tyr Arg Val Glu Leu Ala Glu Lys His Gln Lys Thr Leu Gln Leu Leu
225                 230                 235                 240

Arg Lys Gln Gln Thr Ile Ile Leu Asp Asp Glu Leu Ile Gln Trp Lys
                245                 250                 255

Arg Arg Gln Gln Leu Ala Gly Asn Gly Gly Pro Pro Glu Gly Ser Leu
                260                 265                 270

Asp Val Leu Gln Ser Trp Cys Glu Lys Leu Ala Glu Ile Ile Trp Gln
            275                 280                 285

Asn Arg Gln Gln Ile Arg Arg Ala Glu His Leu Cys Gln Gln Leu Pro
290                 295                 300

Ile Pro Gly Pro Val Glu Glu Met Leu Ala Glu Val Asn Ala Thr Ile
305                 310                 315                 320

Thr Asp Ile Ile Ser Ala Leu Val Thr Ser Thr Phe Ile Ile Glu Lys
                325                 330                 335

Gln Pro Pro Gln Val Leu Lys Thr Gln Thr Lys Phe Ala Ala Thr Val
                340                 345                 350

Arg Leu Leu Val Gly Gly Lys Leu Asn Val His Met Asn Pro Pro Gln
            355                 360                 365

Val Lys Ala Thr Ile Ile Ser Glu Gln Gln Ala Lys Ser Leu Leu Lys
            370                 375                 380

Asn Glu Asn Thr Arg Asn Glu Cys Ser Gly Glu Ile Leu Asn Asn Cys
385                 390                 395                 400

Cys Val Met Glu Tyr His Gln Ala Thr Gly Thr Leu Ser Ala His Phe
                405                 410                 415

Arg Asn Met Ser Leu Lys Arg Ile Lys Arg Ala Asp Arg Arg Gly Ala
                420                 425                 430

Glu Ser Val Thr Glu Glu Lys Phe Thr Val Leu Phe Glu Ser Gln Phe
            435                 440                 445

Ser Val Gly Ser Asn Glu Leu Val Phe Gln Val Lys Thr Leu Ser Leu
            450                 455                 460

Pro Trp Val Ile Val His Gly Ser Gln Asp His Asn Ala Thr Ala Thr
465                 470                 475                 480

Val Leu Trp Asp Asn Ala Phe Ala Glu Pro Gly Arg Val Pro Phe Ala
                485                 490                 495

Val Pro Asp Lys Val Leu Trp Pro Gln Leu Cys Glu Ala Leu Asn Met
            500                 505                 510

Lys Phe Lys Ala Glu Val Gln Ser Asn Arg Gly Leu Thr Lys Glu Asn
            515                 520                 525

Leu Val Phe Leu Ala Gln Lys Leu Phe Asn Asn Ser Ser Ser His Leu
530                 535                 540

Glu Asp Tyr Ser Gly Leu Ser Val Ser Trp Ser Gln Phe Asn Arg Glu
545                 550                 555                 560
```

```
Asn Leu Pro Gly Trp Asn Tyr Thr Phe Trp Gln Trp Phe Asp Gly Val
                565                 570                 575
Met Glu Val Leu Lys Lys His His Lys Pro His Trp Asn Asp Gly Ala
            580                 585                 590
Ile Leu Gly Phe Val Asn Lys Gln Gln Ala His Asp Leu Leu Ile Asn
        595                 600                 605
Lys Pro Asp Gly Thr Phe Leu Leu Arg Phe Ser Asp Ser Glu Ile Gly
    610                 615                 620
Gly Ile Thr Ile Ala Trp Lys Phe Asp Ser Pro Glu Arg Asn Leu Trp
625                 630                 635                 640
Asn Leu Lys Pro Phe Thr Thr Arg Asp Phe Ser Ile Arg Ser Leu Ala
                645                 650                 655
Asp Arg Leu Gly Asp Leu Ser Tyr Leu Ile Tyr Val Phe Pro Asp Arg
            660                 665                 670
Pro Lys Asp Glu Val Phe Ser Lys Tyr Tyr Thr Pro Val Leu Ala Lys
        675                 680                 685
Ala Val Asp Gly Tyr Val Lys Pro Gln Ile Lys Gln Trp Pro Glu Phe
    690                 695                 700
Val Asn Ala Ser Ala Asp Ala Gly Gly Ser Ser Ala Thr Tyr Met Asp
705                 710                 715                 720
Gln Ala Pro Ser Pro Ala Val Cys Pro Gln Ala Pro Tyr Asn Met Tyr
                725                 730                 735
Pro Gln Asn Pro Asp His Val Leu Asp Gln Asp Gly Glu Phe Asp Leu
            740                 745                 750
Asp Glu Thr Met Asp Val Ala Arg His Val Glu Leu Leu Arg Arg
        755                 760                 765
Pro Met Asp Ser Leu Asp Ser Arg Leu Ser Pro Pro Ala Gly Leu Phe
    770                 775                 780
Thr Ser Ala Arg Gly Ser Leu Ser Leu Asp Ser Gln Arg Lys Leu Gln
785                 790                 795                 800
Phe Tyr Glu Asp Arg His Gln Leu Pro Ala Pro Lys Trp Ala Glu Leu
                805                 810                 815
Ala Asn Leu Ile Asn Asn Cys Met Asp Tyr Glu Pro Asp Phe Arg Pro
            820                 825                 830
Ser Phe Arg Ala Ile Ile Arg Asp Leu Asn Ser Leu Phe Thr Pro Asp
    835                 840                 845
Tyr Glu Leu Leu Thr Glu Asn Asp Met Leu Pro Asn Met Arg Ile Gly
    850                 855                 860
Ala Leu Gly Phe Ser Gly Ala Phe Glu Asp Arg Asp Pro Thr Gln Phe
865                 870                 875                 880
Glu Glu Arg His Leu Lys Phe Leu Gln Gln Leu Gly Lys Gly Asn Phe
                885                 890                 895
Gly Ser Val Glu Met Cys Arg Tyr Asp Pro Leu Gln Asp Asn Thr Gly
            900                 905                 910
Glu Trp Ala Val Lys Lys Leu Gln His Ser Thr Glu Glu His Leu Arg
        915                 920                 925
Asp Phe Glu Arg Glu Ile Glu Ile Leu Lys Ser Leu Gln His Asp Asn
    930                 935                 940
Ile Val Lys Tyr Lys Gly Val Cys Tyr Ser Ala Gly Arg Arg Asn Leu
945                 950                 955                 960
Lys Leu Ile Met Glu Tyr Leu Pro Tyr Gly Ser Leu Arg Asp Tyr Leu
                965                 970                 975
```

-continued

```
Gln Lys His Lys Glu Arg Ile Asp His Ile Lys Leu Leu Gln Tyr Thr
            980                 985                 990
Ser Gln Ile Cys Lys Gly Met Glu     Tyr Leu Gly Thr Lys Arg Tyr Ile
            995                1000                1005
His Arg Asp Leu Ala Thr Arg     Asn Ile Leu Val Glu Asn Glu Asn
            1010               1015                1020
Arg Val Lys Ile Gly Asp Phe     Gly Leu Thr Lys Val     Leu Pro Gln
            1025               1030                1035
Asp Lys Glu Tyr Tyr Lys Val     Lys Glu Pro Gly Glu     Ser Pro Ile
            1040               1045                1050
Phe Trp Tyr Ala Pro Glu Ser     Leu Thr Glu Ser Lys     Phe Ser Val
            1055               1060                1065
Ala Ser Asp Val Trp Ser Phe     Gly Trp Leu Tyr Glu     Leu Phe Thr
            1070               1075                1080
Tyr Ile Glu Lys Ser Lys Ser     Pro Pro Ala Glu Phe     Met Arg Met
            1085               1090                1095
Ile Gly Asn Asp Lys Gln Gly     Gln Met Ile Val Phe     His Leu Ile
            1100               1105                1110
Glu Leu Leu Lys Asn Asn Gly     Arg Leu Pro Arg Pro     Asp Gly Cys
            1115               1120                1125
Pro Asp Glu Ile Tyr Met Ile     Met Thr Glu Cys Trp     Asn Asn Asn
            1130               1135                1140
Val Asn Gln Arg Pro Ser Phe     Arg Asp Leu Ala Leu     Arg Val Asp
            1145               1150                1155
Gln Ile Arg Asp Asn
            1160
```